(12) United States Patent
Shvartzman et al.

(10) Patent No.: US 11,819,626 B2
(45) Date of Patent: Nov. 21, 2023

(54) COMPUTER-BASED SYSTEM FOR EDUCATING A BABY AND METHODS OF USE THEREOF

(71) Applicant: Nutrits Ltd., Ramat Gan (IL)

(72) Inventors: Yosef Shvartzman, Tel Aviv (IL); Asaf Kehat, Givatayim (IL)

(73) Assignee: Nutrits Ltd., Ramat Gan (IL)

( * ) Notice: Subject to any disclaimer, the term of this patent is extended or adjusted under 35 U.S.C. 154(b) by 0 days.

(21) Appl. No.: 17/947,669

(22) Filed: Sep. 19, 2022

(65) Prior Publication Data

US 2023/0015714 A1 Jan. 19, 2023

Related U.S. Application Data

(63) Continuation of application No. 17/725,293, filed on Apr. 20, 2022, now Pat. No. 11,446,466.
(Continued)

(51) Int. Cl.
*A61M 21/02* (2006.01)
*A61B 5/00* (2006.01)
(Continued)

(52) U.S. Cl.
CPC .......... *A61M 21/02* (2013.01); *A61B 5/0022* (2013.01); *A61B 5/024* (2013.01);
(Continued)

(58) Field of Classification Search
CPC .......... A61M 21/02; A61M 2021/0022; A61M 2021/0027; A61M 2021/005;
(Continued)

(56) References Cited

U.S. PATENT DOCUMENTS 6,688,888 B1 * 2/2004 Ho .......................... G09B 7/02
434/323
9,852,506 B1 12/2017 Starner et al.
(Continued)

FOREIGN PATENT DOCUMENTS

GB 2554344 B 1/2019
GB 2571125 A 8/2019

OTHER PUBLICATIONS

Willard et al., "Integrating Scientific Knowledge with Machine Learning for Engineering and Environmental Systems", 1,1 (Mar. 2020), 35 pgs.

*Primary Examiner* — Sunita Reddy
(74) *Attorney, Agent, or Firm* — Greenberg Traurig, LLP

(57) ABSTRACT

A system includes a memory, an optical subsystem, an audio system, a plurality of sensors outputting sensor data, a communication circuitry, and a processor. The processor is configured to input to a baby-specific educational machine learning model, image data, audio signal data, sensor data, baby personal data associated with a baby, and a visual image and a sound presented to the baby based on a baby-specific educational plan; to receive an output from the baby-specific educational machine learning model where the output includes an indication that the baby understood or did not understand the visual image and the sound associated with the baby-specific educational plan, and a baby-specific educational recommendation based on the indication; and to execute based on the baby-specific educational recommendation, a modification of the baby-specific educational plan, or a continued execution of the baby-specific educational plan.

11 Claims, 47 Drawing Sheets

Related U.S. Application Data

(60) Provisional application No. 63/222,001, filed on Jul. 15, 2021, provisional application No. 63/186,869, filed on May 11, 2021, provisional application No. 63/177,171, filed on Apr. 20, 2021.

(51) Int. Cl.

| | | |
|---|---|---|
| *A61B 5/11* | (2006.01) | |
| *A61B 5/113* | (2006.01) | |
| *A61B 5/08* | (2006.01) | |
| *A61B 5/024* | (2006.01) | |
| *A61B 5/0205* | (2006.01) | |
| *G06V 10/82* | (2022.01) | |
| *A61M 21/00* | (2006.01) | |

(52) U.S. Cl.
CPC ........ *A61B 5/02055* (2013.01); *A61B 5/0816* (2013.01); *A61B 5/113* (2013.01); *A61B 5/1128* (2013.01); *A61B 5/4809* (2013.01); *A61B 5/4815* (2013.01); *A61B 5/7435* (2013.01); *G06V 10/82* (2022.01); *A61M 2021/005* (2013.01); *A61M 2021/0022* (2013.01); *A61M 2021/0027* (2013.01); *A61M 2230/04* (2013.01); *A61M 2230/42* (2013.01); *A61M 2230/50* (2013.01); *A61M 2230/63* (2013.01)

(58) Field of Classification Search
CPC .......... A61M 2230/04; A61M 2230/42; A61M 2230/50; A61M 2230/63; A61M 2205/18; A61M 2205/3313; A61M 2205/3368; A61M 2205/3375; A61M 2205/3553; A61M 2205/3592; A61M 2205/505; A61M 2230/06; A61B 5/0022; A61B 5/02055; A61B 5/024; A61B 5/0816; A61B 5/1128; A61B 5/113; A61B 5/4809; A61B 5/4815; A61B 5/7435; G06V 10/82; G06V 40/23
USPC ...................................................... 600/26–28
See application file for complete search history.

(56) References Cited

U.S. PATENT DOCUMENTS

| | | | |
|---|---|---|---|
| 9,852,507 B2 | 12/2017 | Gunther et al. | |
| 10,105,617 B2 | 10/2018 | Monge et al. | |
| 10,223,497 B2 | 3/2019 | Pradeep et al. | |
| 10,709,354 B2 | 7/2020 | Gunther et al. | |
| 2003/0197003 A1 | 10/2003 | Kneuer | |
| 2004/0249673 A1 | 12/2004 | Smith | |
| 2008/0020672 A1 | 1/2008 | Osborn | |
| 2014/0272847 A1* | 9/2014 | Grimes | G09B 7/08 434/236 |
| 2015/0182406 A1 | 7/2015 | Falk et al. | |
| 2015/0201846 A1 | 7/2015 | Maiershon et al. | |
| 2015/0250978 A1 | 9/2015 | Pelsue et al. | |
| 2015/0288877 A1 | 10/2015 | Glazer | |
| 2016/0174728 A1* | 6/2016 | Karp | A47D 9/02 5/655 |
| 2016/0293042 A1 | 10/2016 | Pradeep et al. | |
| 2017/0072162 A1 | 3/2017 | Kim et al. | |
| 2017/0156923 A1* | 6/2017 | Utturkar | A61B 5/7278 |
| 2017/0278018 A1* | 9/2017 | Mnih | A63F 13/67 |
| 2018/0078871 A1 | 3/2018 | Monge et al. | |
| 2018/0253954 A1 | 9/2018 | Verma | |
| 2019/0130720 A1 | 5/2019 | Lui | |
| 2019/0358428 A1 | 11/2019 | Wang | |
| 2020/0090534 A1* | 3/2020 | Kozloski | G06N 3/006 |
| 2022/0058979 A1 | 2/2022 | Newell | |
| 2022/0309947 A1* | 9/2022 | Loboda | G09B 19/00 |

\* cited by examiner

|  | Feeding | Soothing | Educational |
|---|---|---|---|
| Inputs | | | |
| Video feed | V | V | V |
| Audio feed | V | V | V |
| Temperature | V | V | V |
| Radio Frequency | V | V | V |
| Lidar | V | V | V |
| Outputs | | | |
| Speaker (audio contact, all variance) | X | V | V |
| Projector (video contact) | X | V | V |
| Vibration Unit | X | V | V |
| Light | X | V | V |
| IoT activate (Feeding warmer) | V | X | X |

FIG. 3

Soothing/Educational

| Input Category | Inputs | | Output Category | Output |
|---|---|---|---|---|
| DSP | Breathing Rate(length, average, variance, etc) | | System | Do nothing |
| | Movement Heatmap | | | Stop current action |
| | Movement Power | | | Activate IoT |
| | Heart Rate(average, variance, etc) | | | User Notification |
| | Child audio wave | | | Third party API |
| | Background audio noise frequency | | Audio | Playing a audio file |
| | Background audio noise power | | | Increase/Decrease Beats per minute (BPM) in audio |
| Semantic algorithm | Blanket state(cover, type) | | | Increase/Decrease Volume in audio |
| | Duration from since last visit of caregiver | | | Change the audio stream |
| | Caregiver presence in the room | | | Changing equalizer parameters(Frequency, Gain, etc) |
| | Foreign objects in the crib | | Projection | Playing a video file |
| | Pacifier (presence, duration, duration missing) | | | Increase/Decrease volume in audio on playing video file |
| Info & System | Date(Weekday, Weekend, Holiday) | | | Increase/Decrease Projection brightness |
| | Time of day | | Vibration | Increase/Decrease Vibration |
| | Weather | | | Change Vibration Rhythm |
| | Age child | | | |
| | Gender | | Room | Change Light color |
| | Height | | | Increase/Decrease Light |
| | Weight | | | Increase/Decrease Temperature |
| | Pregnancy length | | | Increase/Decrease Humidity |
| | User Configuration | | | Increase/Decrease Air Pressure |
| | System Reaction | | | Increase/Decrease Smell Power |
| Physics algorithm | Light intensity | | | Change Smell |
| | Color of Light | | | |
| | Background image noise frequency | | | |
| | Background image noise power | | | |
| | Room Temperature | | | |
| | Humidity | | | |
| | Air Pressure | | | |
| | RF SNR Map | | | |
| | Crib Temperature Heat Map | | | |

| Input Category | Inputs | Output Category | Output |
|---|---|---|---|
| Feeding | | | |
| DSP | Breathing Rate/length, average, variance, etc | System | Do nothing |
| | Movement Heatmap | | Stop current action |
| | Movement Power | | Activate IoT |
| | Heart Rate (average, variance, etc) | | User Notification |
| | Child audio wave | | Thirdparty API |
| | Background audio noise frequency | | |
| | Background audio noise power | Vibration | Increase/Decrease Vibration |
| Semantic migration | Pacifier (presence, duration, duration missing) | | Change Vibration Rhythm |
| Info & System | Date (Workday, Weekend, Holiday) | | |
| | Time of day | | |
| | Weather | | |
| | Age child | | |
| | Gender | | |
| | Height | | |
| | Weight | | |
| | Pregnancy length | | |
| | User Configuration | | |
| | System History Reaction | | |
| Physics algorithms | Background image noise frequency | | |
| | Background image noise power | | |
| | Room Temperature | | |
| | Humidity | | |
| | Air Pressure | | |
| | RF SNR Map | | |
| | Crib Temperature Heat Map | | |

Infant condition description vector (ICDV)

| Breathing Waveform 521 | Crying Level 524 | | |
| --- | --- | --- | --- |
| Temperature Map 522 | Heart rate 525 | | |
| Sleep status 523 | More 526 | | |

| IBH | IPH | ICH |
| --- | --- | --- |
| Movement Level 531 | Audio Response history 541 | Audio Response history 551 |
| Communication Level 532 | Projector Response history 542 | Projector Response history 552 |
| More 533 | More 543 | More 553 |

| ROI ID 3445 | Pixel IDs 3435 |

| Super Pixel ID 3215 | Time Series ID 3220 | Measured Pixel Values 3265 | Pixel IDs 3435 |

| Breath Rate 4231 |
| Maximum Inter-Breath Interval 4233 |
| Minimum Inter-Breath Interval 4235 |
| Inter-Breath Interval Statistics 4237 |
| Inter-Breath Interval Histogram 4239 |
| Apnea Event Data 4241 |

| Motion Frequency 4243 |
| Motion Magnitude 4245 |
| Motion Duration 4247 |
| Sleep Length 4249 |
| Sleep Quality 4251 |
| Sleep Intervals 4253 |

4160

| Field-of-View Policy 4261 | Event Time Interval 4263 | Breathing Event 4265 | Large-Scale Motion 4267 |

*FIG. 15D*

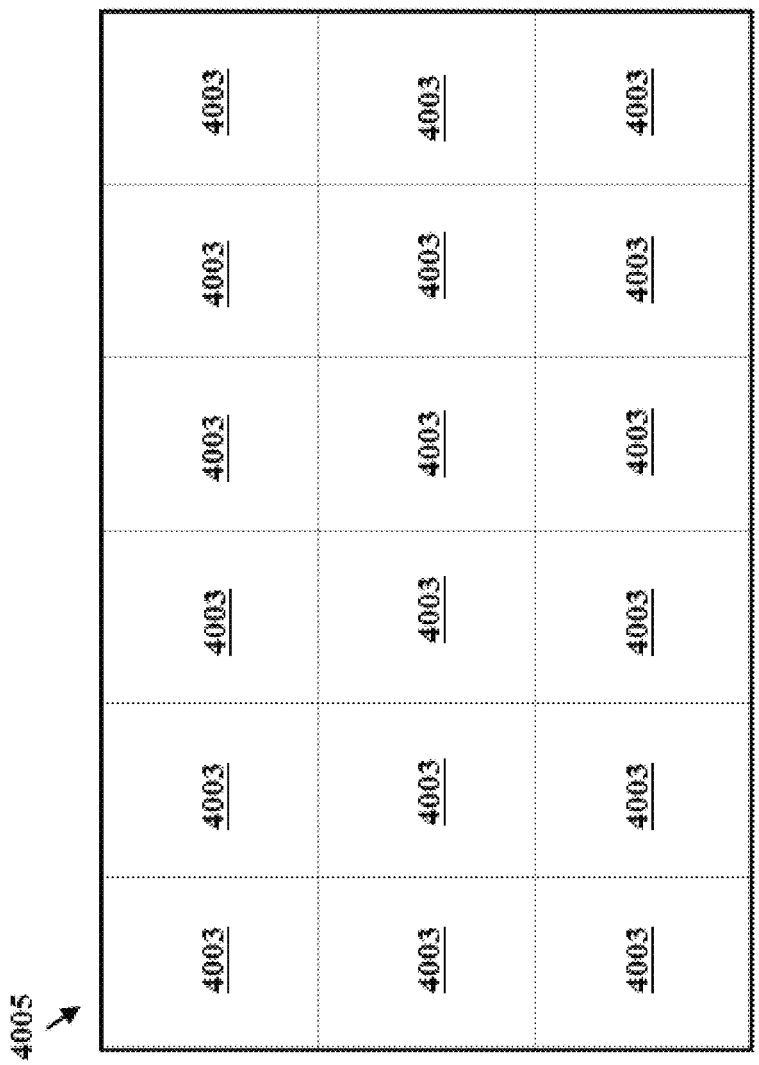

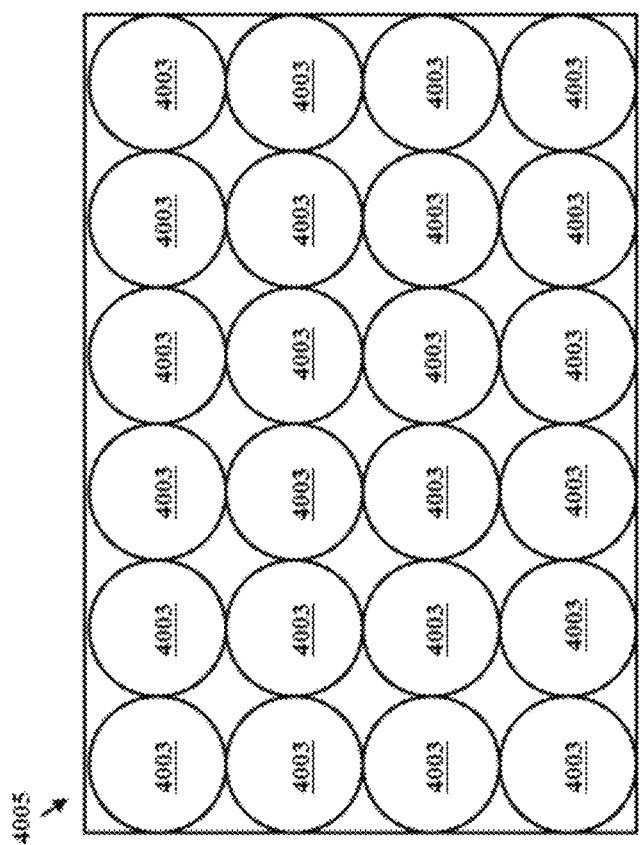

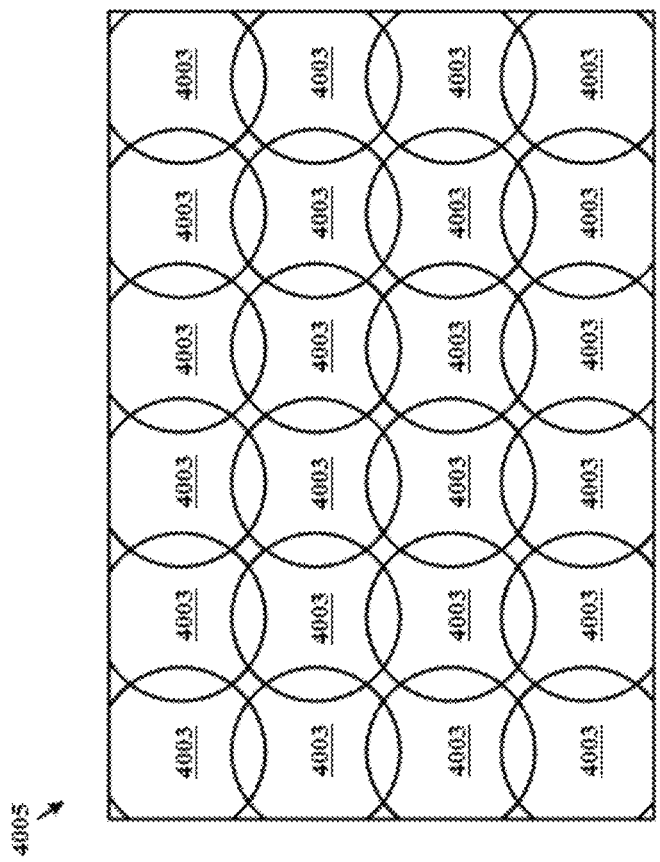

COMPUTER-BASED SYSTEM FOR EDUCATING A BABY AND METHODS OF USE THEREOF

FIELD OF THE DISCLOSURE

The present disclosure relates to a computer-based system for educating a baby and methods of use thereof.

BACKGROUND OF THE DISCLOSURE

Baby monitoring systems have evolved from simple devices such as with sound recording systems only to sophisticated devices which can provide a live video feed of the baby. Baby monitors may be connected to mobile devices, so a caretaker may remotely monitor the baby via a mobile device.

SUMMARY OF THE DISCLOSURE

In some embodiments, the present disclosure provides an exemplary technically improved computer-based system that includes at least the following components of:
- a non-volatile memory;
- at least one electronic resource that may include at least one database;
  - where the at least one database may include:
    - a plurality of baby-specific educational plans for a plurality of babies,
    - (ii) baby-specific stimuli data for a plurality of baby-specific stimuli provided to the plurality of babies based on the plurality of baby-specific educational plans,
    - (iii) baby-specific response data for a plurality of baby-specific responses acquired in response to the plurality of baby-specific stimuli provided to the plurality of babies, and
    - (iv) baby personal data for each baby in the plurality of babies;
- an optical subsystem may include an imaging device, a projection device, or both;
  - where the optical subsystem is configured to perform at least one of:
    - (i) acquire image data from the imaging device of an image of at least one baby from the plurality of babies, or
    - (ii) project by the projection device, at least one visual image to be viewed by the at least one baby;
- an audio system may include a microphone, a speaker, or both;
  - where the audio system is configured to perform at least one of:
    - (i) receive by the microphone, audio signal data from the at least one baby, or
    - (ii) generate by the speaker, at least one sound for the at least one baby;
- a plurality of sensors outputting sensor data;
- a communication circuitry configured to communicate over a communication network with at least one communication device of at least one user associated with the at least one baby; and
- at least one processor configured to execute code stored in the non-volatile memory that causes the at least one processor to:
  - project by the projection device, the at least one visual image to the at least one baby based on at least one baby-specific educational plan from the plurality of baby-specific educational plans for the at least one baby;
  - generate by the audio system, the at least one sound associated with the at least one visual image;
  - receive the image data, the audio signal data, the sensor data, or any combination thereof associated with the at least one baby;
  - determine baby-specific physiological data of the at least one baby based on the image data, the sensor data, and the audio signal data;
  - where the baby-specific physiological data includes:
    - (i) breathing rate signal data of the at least one baby,
    - (ii) spatial body temperature distribution data of the at least one baby,
    - (iii) heartbeat signal data of the at least one baby,
    - (iv) baby motion data of the at least one baby, and
    - (v) baby voice classification data of the at least one baby;
  - input to at least one baby-specific educational machine learning model, the image data, the audio signal data, the sensor data, the at least one visual image, the at least one sound, the baby-specific physiological data, the baby personal data of the at least one baby;
    - where the at least one baby-specific educational machine learning model is trained using datasets based at least in part on the baby-specific stimuli data, the baby-specific response data, the baby personal data, the plurality of baby-specific educational plans, or any combination thereof for each baby in the plurality of babies;
  - receive an output from the at least one baby-specific educational machine learning model; where the output may include:
    - (i) at least one indication that the at least one baby understood or did not understand the at least one visual image and the at least one sound associated with the at least one visual image in accordance with the at least one baby-specific educational plan for the at least one baby;
    - (ii) at least one baby-specific educational recommendation based at least in part on the at least one indication;
  - transmit over the communication network, to the at least one communication device of the at least one user, the at least one indication, the at least one baby-specific educational recommendation, the sensor data, or any combination thereof; and
  - execute, based on the at least one baby-specific educational recommendation, at least one of:
    - (i) a modification of the at least one baby-specific educational plan when the at least one indication indicates that the at least one baby did not understand, or
    - (ii) a continued execution of the at least one baby-specific educational plan for the at least one baby.

BRIEF DESCRIPTION OF THE FIGURES

Various embodiments of the present disclosure can be further explained with reference to the attached drawings, where like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

FIG. 3 is a table of input data sources and output peripheral/IoT devices used by a system to implement the three use cases: a feeding use case, a soothing use case, and an educational use case in accordance with one or more embodiments of the present disclosure;

FIG. 4A is a first exemplary list of input-output data features in a dataset for training a baby-specific behavioral state detection machine learning model and/or a baby-specific educational machine learning model in accordance with one or more embodiments of the present disclosure;

FIG. 4B is a second exemplary list of input-output data features in a dataset for training a baby-specific behavioral state detection machine learning model in accordance with one or more embodiments of the present disclosure;

FIG. 7B illustrates a diagram of the data elements for an infant condition description vector (ICDV) in accordance with one or more embodiments of the present disclosure;

FIG. 11C is a schematic block diagram illustrating ROI data in accordance with one or more embodiments of the present disclosure;

FIG. 11D is a schematic block diagram illustrating super pixel data in accordance with one or more embodiments of the present disclosure;

FIG. 15B is a schematic block diagram of a breathing report in accordance with one or more embodiments of the present disclosure;

FIG. 15C is a schematic block diagram of a motion report in accordance with one or more embodiments of the present disclosure;

FIG. 15D is a schematic block diagram of breathing data in accordance with one or more embodiments of the present disclosure;

FIG. 16A is a schematic diagram illustrating regions in an image frame in accordance with one or more embodiments of the present disclosure;

FIG. 16B is a schematic diagram illustrating regions in an image frame in accordance with one or more embodiments of the present disclosure;

FIG. 16C is a schematic diagram illustrating regions in an image frame in accordance with one or more embodiments of the present disclosure;

DETAILED DESCRIPTION

Figure 1:
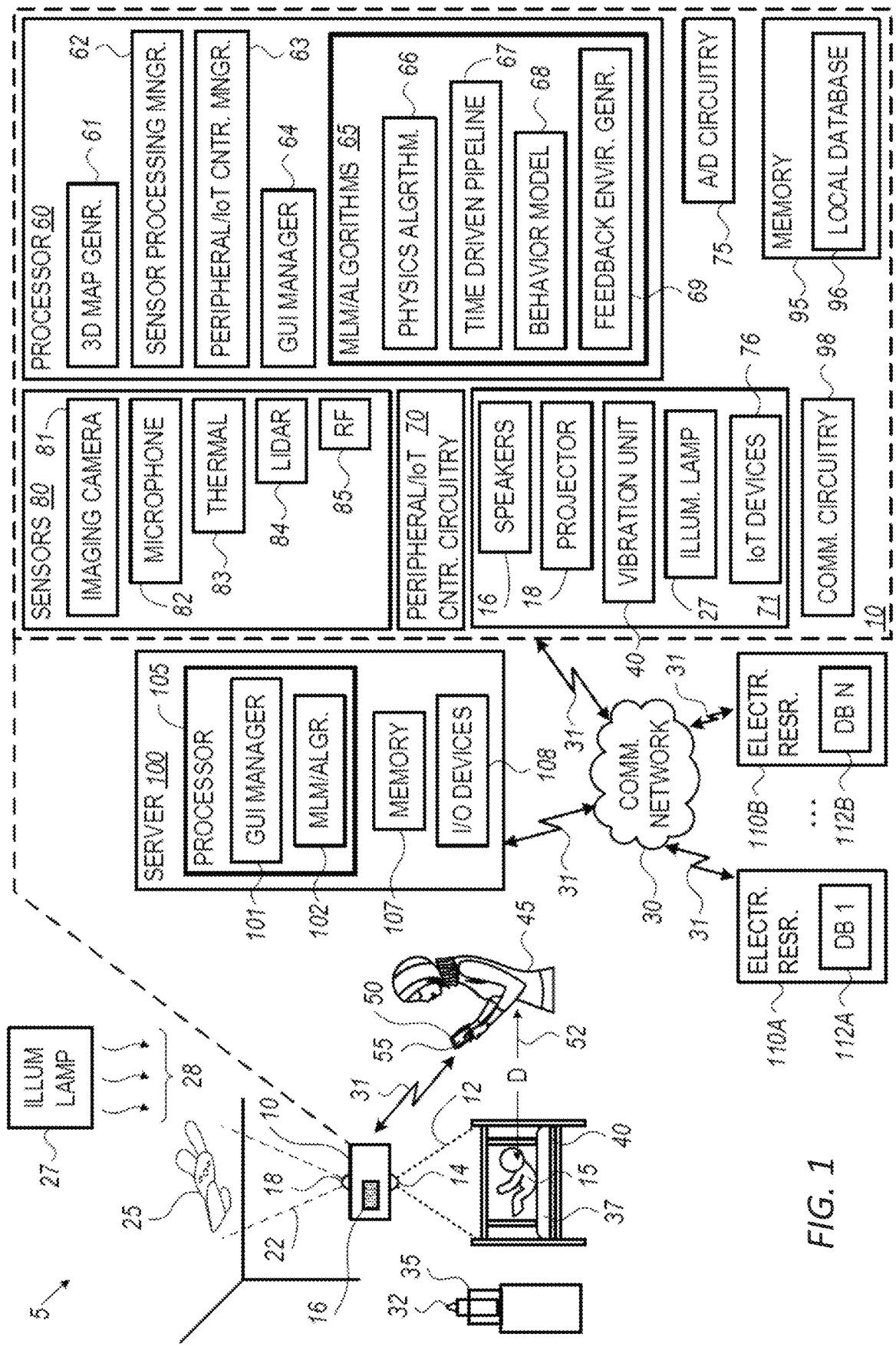
FIG. 1 illustrates a first exemplary embodiment of a computer-based system for monitoring and interacting with a baby in accordance with one or more embodiments of the present disclosure.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

The term 'baby' hereinafter may refer to the subject of the system. The term baby may refer to a newborn, infant or toddler, but the baby may be a child, adult, or elderly person in need of care or stimulation, or it may be an animal, such as a pet that may become noisy when bored or an animal in a veterinary care facility.

The term 'user' hereinafter may refer to a person employing the system to monitor and care for a baby and also to provide stimulation, instruction or development tools for the baby.

Embodiments of the present disclosure herein describe a computer-based system for monitoring and interacting with a baby and methods of use thereof. The system may be implemented with artificial intelligence (e.g., machine learning models) that may collect data and may personalize a full ecosystem of synergies in data collection functionality and feedback, thereby providing a personalized care system. The system may be configured for care of newborns, infants and toddlers. The system may be configured for use with humans and may be configured for use with a member of a group of children, adolescents, adults, the elderly or any combination thereof. In other embodiments, it may be configured for use with animals such as for example, laboratory animals, pets, farm animals, zoo animals, animals under veterinary care, and any combination thereof.

The embodiments disclosed herein solve the technical problem of monitoring and interacting with a baby without the connection of sensing devices to the body of the baby. Using output data from any or all of an imaging device (camera), an audio device (sound transducer such as a microphone), a plurality of sensors, applied to a machine learning model that is trained for a specific use case, the system may determine if the baby is hungry, agitated, or understood images and/or sounds that are projected to the baby according to the use case. The machine learning model is trained to output environmental parameters to change the environment that the baby is in so as to optimize a particular behavior in accordance with the use case. As a result, the baby may be soothed, fed, or presented with images and sound in a particular manner to enhance the education of the baby, all without the physical connection of any sensing devices, transducers, and the like to the baby.

In some embodiments, the system may monitor and interact with a baby for at least three use cases: soothing the baby, feeding the baby, and aiding in the development or education of the baby.

In some embodiments, the user of the system may be a parent or caregiver, a healthcare worker or a childcare worker. The user may be local (e.g., physically close) to the baby or remote from the baby. The system may be used in healthcare facilities, childcare facilities, and other remote use options.

FIG. 1 illustrates a first exemplary embodiment of a computer-based system 5 for monitoring and interacting with a baby in accordance with one or more embodiments of the present disclosure. The system 5 may include a first embodiment of a baby monitor and interaction device (BMID) 10 for monitoring and interacting with a baby 15. The baby 15 may be laying down in a bed or crib on a mattress 37 that may include a vibration unit 40 for applying a vibration stimulus to the baby 15. In other embodiments, the vibration unit 40 may be placed in any suitable location that is operatively coupled to the baby and/or may be placed in a baby's toy such as a teddy bear. The BMID 10 may include sensors 14 configured to monitor the baby 15 located within a sensing region 12. The BMID 10 may include speaker 16 to generate audio signals for the baby 15 to hear. The BMID 10 may include a projection device 18 to project 22 an image 25 for the baby to see.

In some embodiments, the BMID 10 may include a processor, a plurality of sensors 80, an analog-to-digital (A/D) circuitry 75, a memory 95, a communication circuitry 98, peripheral/IoT (internet of things) control circuitry 70, and peripheral/IoT devices 71. The peripheral/IoT devices 71 may include, but are not limited to a speaker 16, a projector 18, the vibration unit 40, an illumination lamp 27, IoT devices 76, and a foodstuff temperature controller 35. Any of the peripheral/IoT devices 71 may be located in the BMID 10, external to the BMID 10 located near to the baby 15 or located remote from the baby 15, but remain communicatively coupled to the BMID 10 via any suitable wired or wireless communication protocol.

In some embodiments, any of the plurality of sensors and/or the peripheral/IoT devices 71 (e.g., the speaker 16, the projector 18, the vibration unit 40, the illumination lamp 27, and/or the IoT devices 76 may be located within the BMID 10 device, or external to the BMID 10, implemented as stand-alone units having any suitable combination of the peripheral/IoT devices 71 but controlled by the peripheral/IoT control circuitry 70.

In some embodiments, the processor 60 may execute software modules that may be stored in the memory 95 that when executed by the processor 60 causes the processor to perform the functions as described herein. The software modules may include a sensor processing manager 62, a three-dimensional (3D) map generator 61, a peripheral/IoT control manager module 63, a GUI manager 64, and/or machine learning model (MLM)/algorithms module 65. The MLM/algorithms module 65 may include any of the following algorithmic blocks that may be based on machine learning: a physics algorithm 66, a time driven pipeline 67, a behavioral model 68, and/or a feedback environmental generator 69.

In some embodiments, the sensor processing manager 62 may be used to process the digital output signal data from the A/D circuitry 75 which may receive analog signal inputs from any of the plurality of sensors 80. In other embodiments, any of the plurality of sensors 80 may include A/D functionality to output digital sensor data directly.

The communication circuitry 98 may be configured to enable the BMID 10 to communicate 31 over a communication network 30 and/or communicate 31 via any suitable wired and/or wireless communication protocol such as Bluetooth and/or Wireless Fidelity (WiFi), for example, with any of the peripheral/IoT devices (e.g., the speaker 16, the projector 18, the vibration unit 40, the illumination lamp 27, and/or the IoT devices 76) and/or with a mobile device 50 associated with a user 45 such as a caretaker and/or parent of the baby 15. For example, the projector 18 may be located in a first unit and the imaging devices of the baby 15 in a second unit separate from the first unit.

In some embodiments, the mobile device 50 may display a graphic user interface (GUI) 55 to the user 45 that may be controlled remotely by the GUI manager 64 and/or to send alerts to the user 40 via the mobile device GUI 55 of the mobile device 50. The BMID 10 may be configured to assess a distance D 52 between the baby 15 and the user 45 for determining whether the user 45 is in a vicinity of the baby 15 or remote from the baby 15 based on the distance D.

In some embodiments, BMID 10 may include any suitable sound transducer such as a microphone 82, and/or an imaging device such as an imaging camera 81 for producing static image data and/or video data (e.g., video data with image frames in a predefined time line) of the baby 15. Other sensors in the plurality of sensors 80 may include a thermal device 83, such as an infrared (IR) camera, a lidar device 84, and/or a radio frequency (RF) device 85. Output data from the imaging camera 81, the thermal imager 83, the lidar device 84, and/or the RF device 85 may be used by the 3D map generation module 61 to generate a time domain three-dimension (3D) map of the baby 15 within the sensing region 12. The time domain three-dimension (3D) map of the baby 15 may be used by the MLM/Algorithms 65 for detecting the position and movements of the baby 15 over any time interval.

The system 5 may include peripheral devices and IoT devices such as the speaker 16, the projector 18, the vibration unit 40, the illumination lamp 27, and/or IoT devices such as the foodstuff temperature controller 35 to maintain a temperature of a baby bottle 32, for example. The peripheral devices and IoT devices may be controlled by the peripheral/IoT control circuitry 70.

The foodstuff temperature controller 35 may be controllable by the BMID 10 to control the temperature of a baby bottle 32 or any suitable baby foodstuff placed in the foodstuff temperature controller 35. For example, if the foodstuff is baby milk, the temperature of the baby milk may be stored at a predefined storage temperature of 4 deg C., for example. When the BMID 10 detects that the baby is hungry, the system 5 may transmit instructions to the foodstuff temperature controller to change the predefined temperature from the predefined storage temperature to a predefined feeding temperature of 37 deg C., for example. In other embodiments, a foodstuff preparation controller (not shown) may be used in any suitable manner to prepare a meal for the baby and is not limited to a foodstuff temperature control. However, the foodstuff preparation controller may include the functionality of the foodstuff temperature controller 35 for warming a bottle, for example.

In some embodiments, the illumination lamp 27 (e.g., the room light) may be controllable by the BMID 10 to illuminate 28 the baby 10 at different light frequencies (e.g., colors), and/or light illumination levels, for example. The BMID 10 may control the illumination lamp 27 which may be dynamically changed to provide different colors and/or illumination levels to the baby 15 over any time interval.

In some embodiments, the system 5 may include a plurality of electronic resources 110 denoted as N electronic resources: ELECTR RESR1 110A . . . ELECTR RESRN 110B, where N is an integer, that may respectively include N databases denoted DB1 112A . . . DBN 112B. The memory 95 may also include a local database 96.

In some embodiments, an optical subsystem may refer to the imaging camera 81, the projector 18, or both. The audio system may refer to the microphone 82, the speaker 16, or both.

In some embodiments, the system 5 may include the server 100 communicating 31 over the communication network 30 with any of the elements shown in FIG. 1. The server 100 may include a processor 105, a communication circuitry 106, a memory 107, and/or input/output (I/O) devices 108 such as a display, keyboard, mouse, and the like. The processor 105 of the server 100 may be configured to perform any or all of the functionality performed by the BMID 10 such as a GUI manager 101 controlling a plurality of mobile devices associated with a plurality of users associated with a plurality of babies, and/or an MLM/Algorithm module 102 for processing data for a plurality of babies. Furthermore, in other embodiments, the server 100 may control a plurality of baby monitor and interaction devices (BMID) for use with different babies from the plurality of babies using the system 5.

In some embodiments, the system 5 may provide a mobile and personalized system that may include a soothing, two-way video communication with the baby 15 via the plurality of sensors 80 and/or the peripheral/IoT devices, an artificial intelligence (AI)-based infant and toddler development system, an AI-based infant and toddler education system, an AI-based infant and toddler entertainment system, or any combination thereof. AI-based refers to the use of machine learning models and algorithms.

In some embodiments, the physics algorithm module 66 may process the output data from the plurality of sensors 80 to implement functionality of a breathing detector, a temperature detector, a heart rate detector, a detector of other vital signs, or any combination thereof. The physics algorithm module 66 may use the breathing monitoring algorithm and a heart rate monitoring algorithm to respectively implement breathing detection and heart rate detection from the output sensor data as will be described hereinbelow.

Figure 2A:
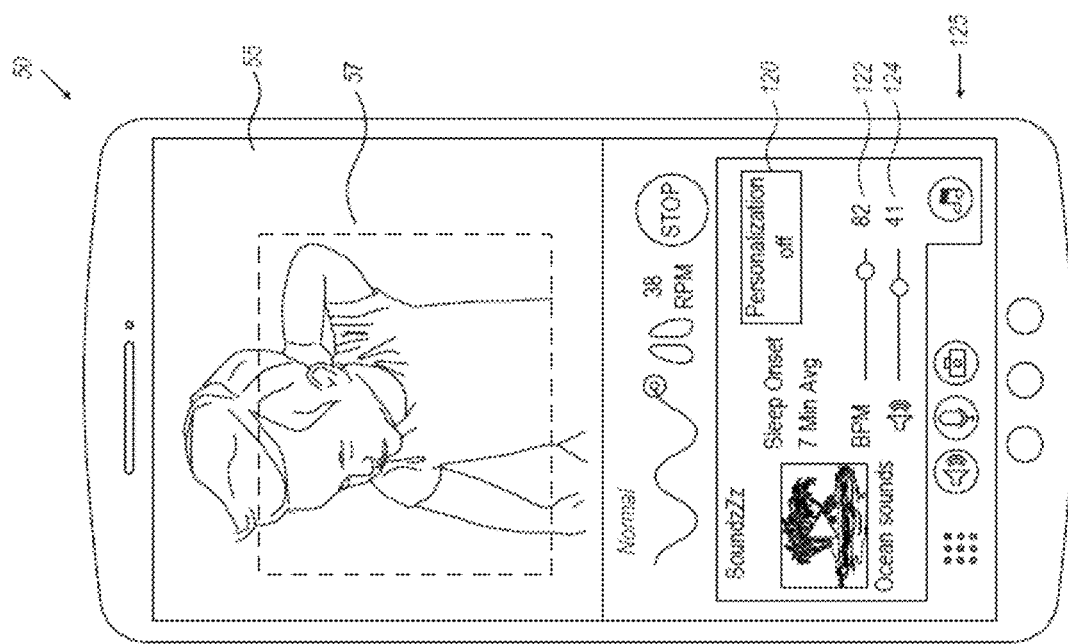
FIG. 2A is a first exemplary screenshot of graphic user interface of a mobile device in a system configured to soothe a baby in accordance with one or more embodiments of the present disclosure.

FIG. 2A is a first exemplary screenshot of the graphic user interface 55 of the mobile device 50 in the system 5 configured to the soothe the baby 15 in accordance with one or more embodiments of the present disclosure. The first exemplary screenshot of the GUI 55 may be used in the soothing use-case. The GUI 55 may include indicia of a sleep state 120 of the baby, a heart rate 122 (in beats per minute—BPM), and a volume level 124 of an audio signal being played via the speakers 16 to the baby 15. The GUI 55 may include graphic objects 125 for the user 45 to activate (e.g., icons to press) for performing different interactive functions with the baby 15. The GUI 55 in a region 57 may display to the user 45 real time images and/or videos of the baby 15.

Figure 2C:
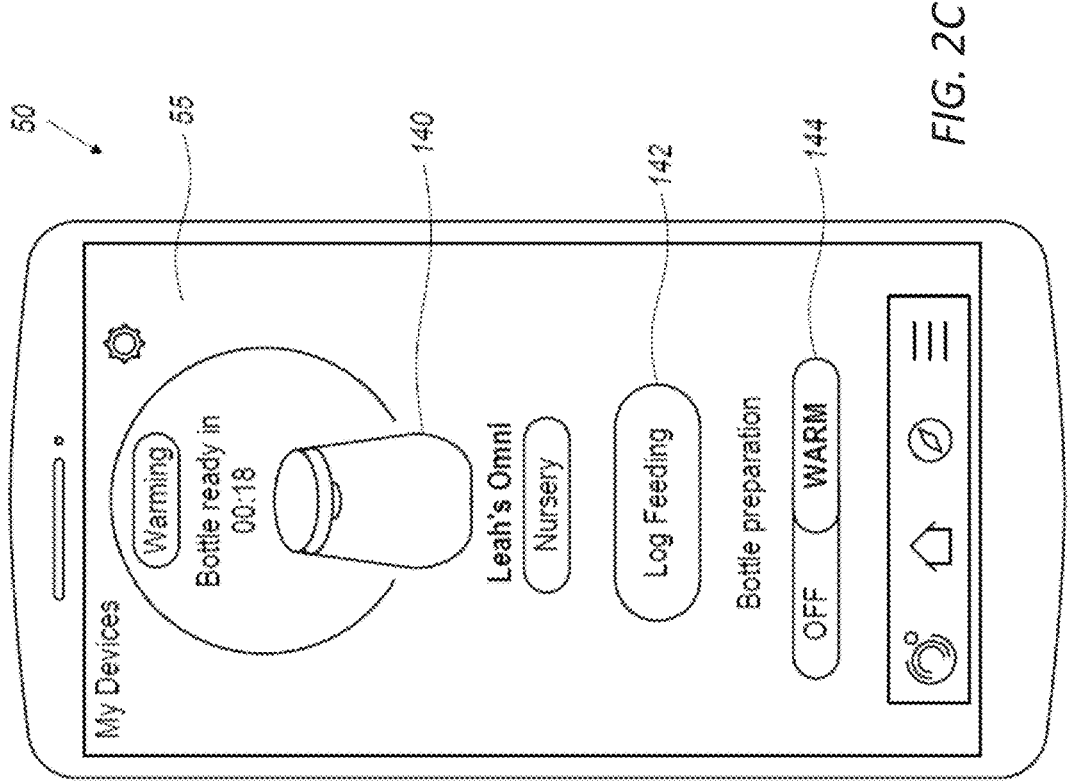
FIG. 2C is a third exemplary screenshot of a graphic user interface of a mobile device to alert a user to feed a baby in accordance with one or more embodiments of the present disclosure.
Figure 2B:
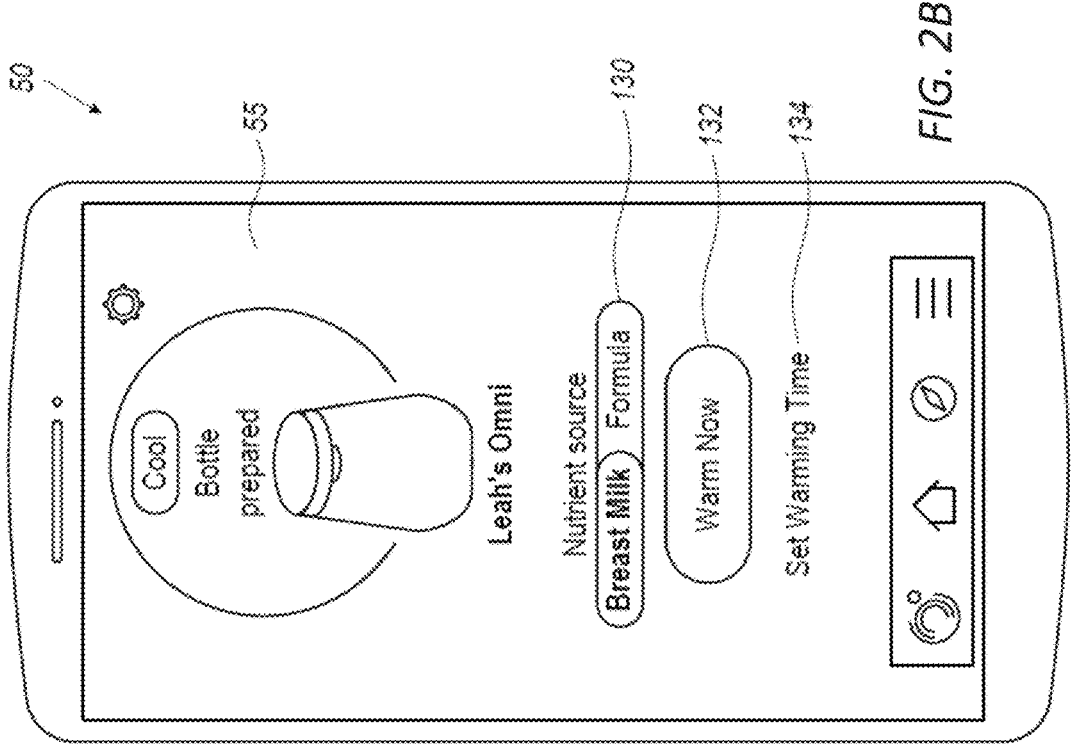
FIG. 2B is a second exemplary screenshot of a graphic user interface of a mobile device in a system configured to prepare foodstuff for feeding a baby in accordance with one or more embodiments of the present disclosure.

FIG. 2B is a second exemplary screenshot of the graphic user interface 55 of the mobile device 50 in the system 5 configured to prepare foodstuff for feeding the baby 15 in accordance with one or more embodiments of the present disclosure. The second exemplary screenshot of the GUI 55 may be used in the feeding use-case. The GUI 55 may include indicia such as the nutrient source 130 of the foodstuff (e.g., breast milk), a set state 132 of the foodstuff temperature controller 35 (e.g., the user may press the graphic object "Warm Now"), and a set state 134 field that may allow the user 45 to enter the warming time.

FIG. 2C is a third exemplary screenshot of the graphic user interface 55 of the mobile device 50 to alert the user 45 to feed the baby 15 in accordance with one or more embodiments of the present disclosure. The third exemplary screenshot of the GUI 55 may be used in the feeding use-case. The GUI may include indicia such as a time 140 when the foodstuff (e.g., breast milk) will be ready to feed to the baby 15, a button to log the feeding 142 after the feeding was completed, and foodstuff preparation state indicator 144 field (e.g., bottle preparation state—OFF/WARM).

Figure 2D:
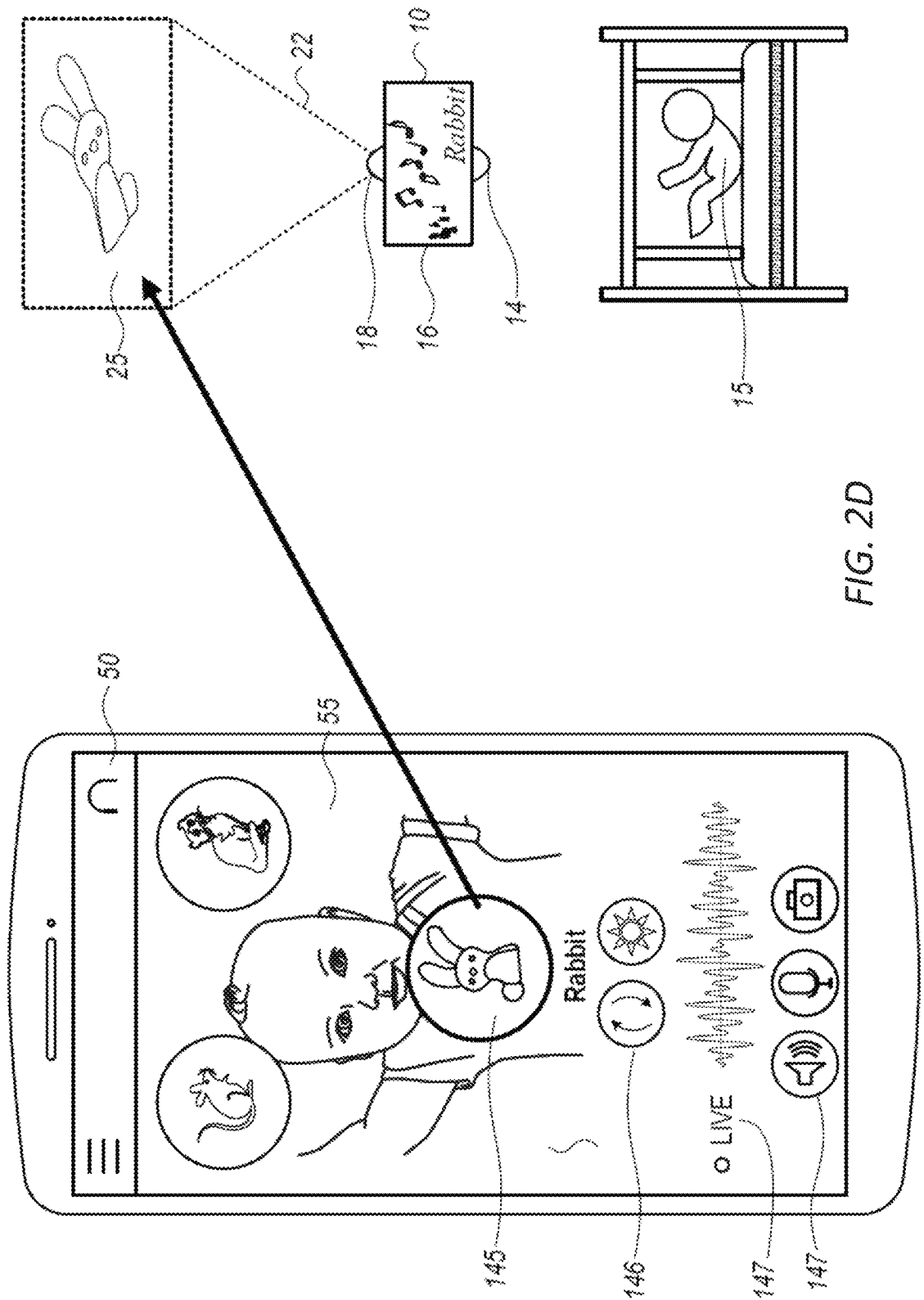
FIG. 2D is a fourth exemplary screenshot of a graphic user interface of a mobile device in a system for educating a baby by projecting an image in accordance with one or more embodiments of the present disclosure.

FIG. 2D is a fourth exemplary screenshot of the graphic user interface 55 of the mobile device 50 in the system 5 for educating the baby 15 by projecting 22 the image 25 in accordance with one or more embodiments of the present disclosure. The fourth exemplary screenshot of the GUI 55 may be used in the education use-case. The GUI 55 may include indicia such as a rabbit icon 145 to notify the user 45 that the BMID 10 is projecting a rabbit to the baby 15, an image advance button 146 to change the image, an audio waveform indicator 147 that the speakers 16 of the BMID 10 is playing an audio signal 18 associated with the image 25 of the rabbit, and other graphic objects 148 for the user 45 to activate (e.g., icons for the user to press). The GUI may also include a live video feed of the baby 15.

FIG. 3 is a table 150 of the input data sources and the output peripheral/IoT devices used by the system 5 to implement the three use cases: feeding use case 152, soothing use case 154, and educational use case 156 in accordance with one or more embodiments of the present disclosure.

In some embodiments, although the system 5 may include the same input data sources from the same plurality of sensors 80, the MLM/Algorithms 65 may be different (e.g., trained differently) for implementing the three different use-cases: the feeding use case 152, the soothing use case 154, and the educational use case 156. In other embodiments, the MLM/Algorithms 65 may be trained for system 5 to implement all of the use cases.

In some embodiments, for the feeding use case 152 and the soothing use case 154, the MLM/Algorithms 65 may include a baby-specific behavioral state detection machine learning model that receives as an input the audio signal data from the microphone 82, the image data generated from the imaging camera 81, and the sensor data from the thermal imager 83, the lidar device 84, and the RF device 85, and baby-specific personal data unique to the baby 15. The sensor data may be algorithmically processed, for example, to breathing waveform signal data of the baby 15, spatial body temperature distribution data of the baby 15, heart rate waveform signal data, and/or any suitable signal data derived from the output data from any of the plurality of sensors 80.

In the feeding use case 152, the baby-specific behavioral state detection machine learning model may be trained to output an indication that the baby is hungry, transmit an alert via the mobile device 50 to the user 45 (see FIGS. 2B and 2C) that the baby is hungry, and to transmit instructions to the foodstuff temperature controller 35 to set the change the predefined temperature of the foodstuff to feed the baby 15.

In the soothing use case 154, the baby-specific behavioral state detection machine learning model may be trained to output an indication that the baby is hungry, transmit an alert via the mobile device 50 to the user 45 (see FIG. 2A) that the baby is agitated, about to wake up, or both, and to transmit instructions to the audio system, the optical subsystem or both to perform actions to reduce the agitation of the baby such as the baby crying. These actions may include but are not limited to: (1) causing the audio system to generate and play for the baby 15, a soothing sound which reduces a level of agitation or irritation of the baby 15, (2) causing the audio system to generate and play for the baby 15, a sleep-enhancing sound which causes the baby 15 to fall asleep and/or to prevent the baby from waking up, and/or (3) causing the optical subsystem to project a relaxing image to the baby which reduces a level of agitation or irritation of the baby 15 when the baby 15 views the relaxing image for the soothing use case.

In some embodiments, for the educational use case 156, the MLM/Algorithms 65 may include a baby-specific educational machine learning model that receives as an input the audio signal data from the microphone 82, the image data generated from the imaging camera 81, and the sensor data from the thermal imager 83, the lidar device 84, and the RF device 85, and baby-specific personal data unique to the baby 15. The sensor data may include, for example, breathing waveform signal data of the baby 15, spatial body temperature distribution data of the baby 15, heart rate waveform signal data, and/or any suitable signal data derived from any of the plurality of sensors 80.

In the educational use case 156, the baby-specific educational machine learning model may be trained to output (1) an indication that the baby understood or did not understand the visual image and audio output associated with the visual image (see FIG. 2D), and (2) a baby-specific educational recommendation based on the understanding indication. In response to the output of the baby-specific educational machine learning model, the processor 60 may then execute, based on the baby-specific educational recommendation(s), at least one of: (1) a modification of the at least one baby-specific educational plan when the at least one indication indicates that the at least one baby did not understand, or (2) a continued execution of the baby-specific educational plan for the at least one baby, for example.

FIG. 4A is a first exemplary list 160 of input-output data features in a dataset for training the baby-specific behavioral state detection machine learning model and/or the baby-specific educational machine learning model in accordance with one or more embodiments of the present disclosure. The input features 163 for the input feature categories 162 and the output features 165 for the output feature categories 164 in the table shown in FIG. 4A are directed to the soothing use case 154 and educational use case 156. Although the first exemplary input-output dataset 160 may illustrate 30 different features, for example, this is merely for conceptual clarity and not by way of limitation of the embodiments disclosed herein. The input-output training sets may include 1000 features, 10,000 features, or 100,000 features.

FIG. 4B is a second exemplary list 170 of input-output data features in a dataset for training the baby-specific behavioral state detection machine learning model in accordance with one or more embodiments of the present disclosure. The input features 174 for the input feature categories 173 and the output features 176 for the output feature categories 175 in the table shown in FIG. 4B are directed to the feeding use case 152. Although the second exemplary list 160 may illustrate 20 different features, for example, this is merely for conceptual clarity and not by way of limitation of the embodiments disclosed herein. The input-output training sets may include 1000 features, 10,000 features, or 100,000 features.

With regard to lists of input (stimuli) feature data and output (response) feature data shown in the tables of FIGS. 4A-4B, the inputs 163 and 174 show examples, without limitation, of the baby-specific stimuli data including but limited to environmental data such as weather, time of day, room light intensity, temperature, humidity, etc; baby-specific physiological data such as but not limited to breathing rate, movement heatmap, pacifier presence etc. These inputs may include baby-specific personal data such as for example without limitation, age, height, weight, pregnancy length, and the like.

In some embodiments, the baby-specific response data or the output features 165 and 176 may include for example, doing nothing, notify user, stop current action, play a video file on the projector 18, increase/decrease light, increase/decrease temperature, change smell, change vibration rhythm, and the like.

In some embodiments, any electronic resource from the plurality of electronic resources 110 may store in any of the N databases 112: (1) a plurality of baby-specific educational plans for a plurality of babies, (2) baby-specific stimuli data for a plurality of baby-specific stimuli provided to the plurality of babies, (3) baby-specific response data for a plurality of baby-specific responses acquired in response to the plurality of baby-specific stimuli provided to the plurality of babies, and (4) baby-specific personal data for each baby in the plurality of babies.

Note that the system 5 may query the electronic resources to retrieve the data from a plurality of babies. The baby-specific stimuli data and the baby-specific response data from the plurality of babies may also be referred to herein as crowdsourcing data, or infant crowdsourced data that may be data associated with other babies using the system 5 via a server 100, from laboratory experiments, or any combination thereof.

In some embodiments, the data from the electronic resources 110 may be used to create datasets for training any of the machine learning models and/or algorithms as discussed herein. Thus, when inputting data associated with a specific baby into each of the machine learning models as discussed herein, the output data from each of the machine learning models incorporated the data (e.g., the learning) from a large population of babies on the order of 100 babies, 1,000 babies, 10,000 babies, or 100,000 babies.

In some embodiments, the baby-specific stimuli data from the plurality of babies may also include the simulated baby-specific physiological data for the plurality of babies. For example, image data from an image camera that images the baby and audio data from a microphone or sound transducer sampling the voice of the baby and/or sounds emitted from the baby may be processed to simulated or compute baby-specific physiological data such as heartbeat data (see algorithms associated for example, with FIGS. 10-14) and/or breathing data (see algorithms associated for example FIGS. 15-19), for example. This simulated data may also be included in the datasets.

In some embodiments, in order to generate the training dataset, the baby-specific stimuli data and the baby-specific response data for each baby from the plurality of babies, the data stored databases in the electronic resources may include the same data as that shown in the exemplary lists of FIGS. 4A-4B, from which the sensor data, image data and/or audio data features may be extracted for each baby to train the machine learning models.

In some embodiments, the breathing rate signal data may be simulated using the algorithms associated with FIGS. 15-19. In short, the image (video) data and/or the audio data of the baby may be used to identify pixels in the image associated with the baby's chest region and to monitor those identified pixels in time for characteristic periodic breathing movements. From this pixel change analysis, the breathing rate may be calculated. If there are no characteristic periodic breathing movements detected, the system 5 may generate a notification such as an alert on the GUI 55 that the baby is not breathing.

In some embodiments, the spatial body temperature distribution data may be acquired from an IR array thermal imaging camera such as for example, MLX90640 IR Array Thermal Imaging Camera, 32×24 Pixels, 110° FOV from Waveshare Electronics World Trade Plaza south side, Fuhong Rd, Futian District, Shenzhen, 518033, China. When the thermal imaging camera is positioned to image the baby and may also capture objects in the baby's immediate environment such as for example, the baby's blanket, the output data from the camera may be a spatial mapping of the baby's external body temperature at different locations on the along the contour of the baby's body and the temperature at certain spatial points along the contours of the objects in the baby's environment.

In some embodiments, the heartbeat signal data may be computed by applying algorithms related to FIGS. 10-14 described hereinbelow to the image (video) data of the baby. The baby heartbeat signal data may be, for example, the computed heartbeat signal $h_r(t)$ 3465 as referenced in FIG. 11E hereinbelow.

In some embodiments, the baby motion data (e.g., the movement heatmap and/or the movement power of the baby's motions) may be derived from the image (video) data and/or the spatial body temperature distribution data. Pixel change algorithms may be applied to the video data, for example, that may be used to track pixels in time to identify the movement power where low power movements are defined as small movement motions of the baby, and high-power movement are defined as large movement motions of the baby such as the baby flipping over, for example. In other embodiments, anatomical movements of the baby (head, shoulders etc) also known as skeleton detection algorithms of the baby may be used detected movements of the baby.

In some embodiments, the baby voice classification data may include the baby's voice rate, voice magnitude, voice type (a cry, a cry when hungry, a cry for attention, mumbling, choking, coughing, swallowing, etc) and voice pitch, for example, that may be determined by applying a classification model and/or a genetic classification to the raw audio data.

Note that the input-output data features in FIGS. 4A and 4B for the baby-specific features and the environmental-specific features for each use case are related to the baby-specific stimuli data and baby-specific response data stored in the databases of the electronic resources. For example, the baby-specific stimuli data (e.g., baby-specific features 225) may include baby-specific personal data, breathing detection data, heart rate detection data, baby voice data, baby temperature data that may be representative of the baby's behavioral state as well as the environmental-specific features 230 at any instant of time that may be inputted to the machine learning models. Thus, the baby-specific response data may be indicative of the baby's response or actions to change the behavioral state of the baby. When this data is used to train the machine learning models, the machine learning models may incorporate the environmental stimuli and the baby's behavioral state in the baby-specific stimuli data for each baby in the plurality of babies so as to output the actions, recommendations, notifications and/or behavioral state indications to change the baby's behavioral state for each baby from the plurality of babies.

In some embodiments, the output data generated from the plurality of sensors 80 may be preprocessed using different pre-processing algorithms to generate the input data features for training the machine learning models. For example, the output data of the image camera 81, the thermal imager 83, the lidar device 84 and/or the RF device 85 may be used in algorithms disclosed hereinbelow that may determine the breathing and heart rate of the baby 15 over time. The processor 60 may use the output data from the plurality of sensors 80 in the 3D map generation module 61 to generate a 3D map of the baby 15 as a function of time so as to generate a movement heatmap and/or movement power. The machine learning models may be trained to output different actions and transmit instructions to the different peripheral/IoT devices. These actions may include but are not limited to playing an audio file with time varying parameters such as the varying volume, frequency of the audio signal and the like (e.g., equalizer), playing a video file and varying projection brightness, for example, to apply a vibration intensity and vibration pattern to the baby 15 via the vibration unit 40, to change the room light 28 (e.g., control the illumination lamp 27 to vary the light color and illumination intensity), and/or to change the room temperature, humidity, air pressure, changes in smell in the sensing region 12 by the BMID 10 varying different IoT device states controlling a thermostat, a humidifier, actuators to open/close windows, activate a fan, the foodstuff temperature controller 35, and/or aromatherapy devices in the baby's room, for example.

In some embodiments, the system 5 may collect data through the plurality of sensors 80 from the baby such as, for example, behavioral data, and may provide stimulation or soothing through the peripheral/IoT devices after processing the behavioral data by the MLM/algorithm module 65. For example, changes in the baby's breathing rate or changes in its crying, the baby's sleeping and waking patterns may be determined. The system may then react to the baby's behavior patterns, providing stimulation when appropriate and soothing (e.g., reducing the baby's level of agitation, or irritability) when appropriate. In some embodiments, the system 5 may detect that the baby is hungry. The system 5 may prepare the foodstuff (e.g., warming up the baby bottle 32 by the temperature controller 35) and then the user 45 may be alerted via a mobile device 50 such that when the user 45 arrives to the baby 15, the foodstuff is ready to feed to the baby 15 (e.g., at the correct predefined temperature).

In some embodiments, if the system 5 detects, based on both video and audio analysis, that the baby is tired or uncomfortable, the system 5 may be configured to soothe the baby using an AI-based soothing system by playing soothing music, providing vibrations, and/or projecting images to the baby. In other embodiments, the system 5 may determine whether the baby's level of discomfort may be reduced by soothing only. In yet other embodiments, the system 5 may determine using the AI-based algorithms to send an alert via the GUI 55 to the user 45 that attention needs to be given to the baby.

In some embodiments, if the system 5 assesses that only soothing is needed, the system 5 may automatically start playing a comforting sound. The comforting sound may be chosen to be optimal for that baby, that is the tune, volume, and/or play duration, for example, may be AI-tailored to the baby. In other embodiments, both the comforting sound and the volume may be adjusted as needed, based on the baby's responses. The sound may be a tune, white noise, a hum, a pre-recorded voice of a parent, grandparent or caregiver, or any combination thereof. In other embodiments, the machine learning model may output the soothing sound to be generated by the speaker to the baby 15.

In some embodiments, system 5 may implement a baby-specific soothing procedure (e.g., tailored to a particular baby) that may include the following steps:

1. Crying may be detected (via audio and/or video).
2. At least one of a sound, video, image or vibration may sent to calm the baby. In some embodiments, the sound, video, image or vibration may continue to be played until the baby is asleep.
3. The baby's behavior may be sampled by the system 5, such as for example in predefined time intervals.
4. If system 5 detects that the baby has not calmed down (or is not asleep), the system 5 may change at least one: a sound played to the baby, a video or image projected for the baby to see, and/or a vibration applied via a vibration unit such as a vibration mat. For example, one or more additional sounds, videos, images and/or vibrations may be added. A volume of the sound may be made to be louder or softer. The type of sound may be changed (change tune, change caregiver recorded voice, change what the caregiver is saying, change to white noise, change to hum, etc.). Similarly, a vibration applied to the baby may be made stronger or weaker, or the type of vibration may be changed. A video or image displayed to the baby may be changed. The display of the video or image may be made brighter, paler, stronger or weaker. A colored image may be recolored.
5. The system may recheck or re-sample the baby's behavior (changes in crying noise/breathing rate, etc.)
6. Repeat steps 4 to 6 until the baby calms down (or falls asleep).

In some embodiments, the system 5 may improve the machine learning models/algorithms 65 by retraining them so as to model the real-time behavior of a particular baby.

Thus, the system 5 may start a future soothing procedure from a known starting point when the baby needs to be soothed again since the retrained model has already captured what kind of actions, such as sound, illumination, projected images, vibration, etc that worked previously to soothe the particular baby.

In some embodiments, the system 5 may query data from at least one electronic resource store 110 baby-specific stimuli data for a plurality of baby-specific stimuli provided to a plurality of babies as well as baby-specific response data for a plurality of baby-specific responses acquired in response to the baby-specific stimuli provided to a plurality of babies. Thus, the system may train the machine learning models using the data from the plurality of babies that may capture, for example, what works better for babies with similar characteristics to a particular baby. The system may be configured to dynamically adapt the solution to each child.

In some embodiments, the system 5 may be configured to predict increases in the baby's stress levels and to automatically execute solutions outputted by the machine learning models to reduce the baby's stress.

In some embodiments, a monitoring subsystem (e.g., may include a two-way audio system) may be detachable from the main system (e.g., the BMID 10) and may be portable so that the soothing system may be used when the baby is not in the presence of the main system such as for example, when the baby is in a stroller or in a vehicle but communicative coupled via wired or wireless communication protocols. In other embodiments, the monitoring subsystem may include a battery or any suitable power storage device. In yet other embodiments, the monitoring subsystem may be docked to the main system for recharging, and/or may be connected to at least one conventional powering system.

In some embodiments, the system 5 may include a two-way video system that may enable the user 45 such as parents, family members and/or caregivers associated with the baby 15 to have two-way communication with the baby 15. The two-way video system may project a video image of the user 45 on any convenient flat surface in the vicinity of the baby. A video image of the baby may be displayed to the user via any convenient screen such as, for example, a computer display (e.g., laptop, desktop, and/or tablet) or the GUI 55 of the mobile phone 50.

In some embodiments, the system 5 may be configured to provide stimulation and education to the baby. Images may be shown, for example, with a voice telling the baby what the image is via the speaker 16. The monitoring systems (e.g., the BMID 10) may be configured to determine, from the baby's reactions such as, for example, its eye movements, body movements, and/or the baby's voice, whether the baby 15 is paying attention to the displayed images or sounds, and whether the baby 15 is understanding what the baby 15 sees. The system 5 may also be configured to determine, for example, by the baby's eye movements and/or body movements, if the baby is getting bored and the BMID 10 may discontinue the baby-specific educational plan for the baby 15 until the baby 15 shows interest again in the projected image 25. In some embodiments, the user 45 may be alerted via the GUI 55 of the mobile device 50, for example, that the baby has learned a new word or new concept. Therefore, the personalized baby-specific educational plan may be provided for the baby 15, based on AI. In other embodiments, the user 45 via the GUI 55 may be able to the change or tailor the personalized baby-specific educational plan in real time.

In some embodiments, the personalized baby-specific educational plan may be used for many years, for example, with the educational and soothing use cases being altered as the child develops. These stages may be in collaborations with, for example, service providers, subscribers, interactive games, users, or any combination thereof.

In some embodiments, the education, development and entertainment systems based on the personalized baby-specific educational plan may be viewed as a "university" for babies. The use of the personalized baby-specific educational plan for the baby 15 may be free or subscription-based. Subscription-based systems may use business-to-business models or business-to-consumer models for the entertainment and mass media markets.

Figure 5A:
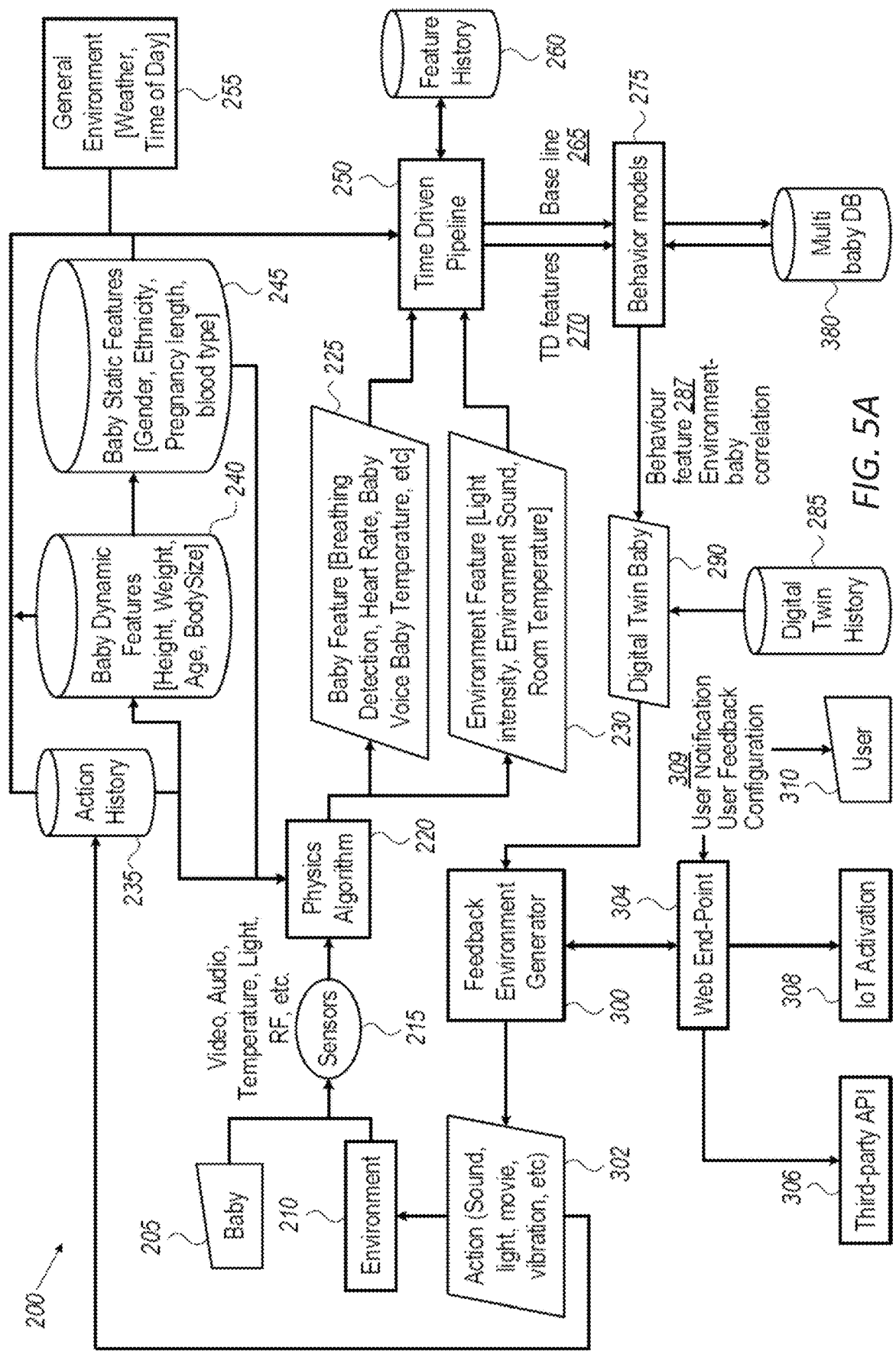
FIG. 5A is an algorithmic flow diagram of a computer-based system for monitoring and interacting with a baby in accordance with one or more embodiments of the present disclosure.

FIG. 5A is an algorithmic flow diagram 200 of the computer-based system for monitoring and interacting with a baby in accordance with one or more embodiments of the present disclosure. The algorithmic flow diagram may be used to generate training datasets for the machine learning models disclosed herein for each use case. The machine learning models may incorporate the functionality of one or more algorithmic blocks in the algorithmic flow diagram 200 into the machine learning models once trained.

In some embodiments, with regard to a physics algorithm 220 data pipeline, the processor 60 may be configured to process raw sensor data 215 (e.g, video, audio, temperature, light, RF etc) related to either a baby 205 and/or an environment 210 in which the baby 205 is present. Note that the physics algorithm module 66 of FIG. 1 is equivalent to the physics algorithm 220 block of FIG. 5A. The sensor data 215 may be inputted into the physics algorithm 220. The physics algorithm 220 is configured to output baby metadata and environment metadata from which features may be extracted that characterize the baby 205 and the environmental conditions 210. The baby-specific features may include, for example, baby-specific physiological data such as a baby heart rate, a baby heart rate variability, baby temperatures at various locations on the baby's body, baby voice classification data such as the baby's voice rate, voice magnitude and voice pitch, baby motion rate, moving parts, etc. The environmental-specific features may include light intensity, sound, room temperature, etc.

In some embodiments, the physics algorithm 220 may preprocess sensor data by applying filtering, decimation and calibration operations, for example, to the sensor data to generate time waveforms and/or images (videos). The signal to noise ratio of the time waveforms and/or images may be improved by filtering relevant frequency bands of babies for each sensor. Differentiating between environmental data and baby data may be implemented using sensor fusion algorithms, for example, cross correlation of sound transducers oriented at various positions. Then generating signal transformations, for example, by applying using a 1D Fourier transform, 2D Spectrograms, wavelets, 2D/3D fast Fourier Transforms for images and videos, hilbert transform (for envelope signal), cepstrums (e.g., autocorrelated signal balancing), and the like.

In some embodiments, feature extraction algorithms may be applied to the relevant vectors for diagnostics to extract features (e.g., baby-specific features 225 and environment features 230) using basic mathematical operations, such as for example, sound and light mean and root mean squares, probability density function, moments of waveforms, etc. Other baby-specific features may also be extracted using advanced algorithms, such as for example, a baby heart rate may be extracted using Euler magnification of the FFT phase to identify repeated changes and to quantify its heart rate using the (smartbeat) heartbeat detection algorithms as disclosed hereinbelow.

In some embodiments, a baby smile rate may be extracted using a pattern recognition algorithm from the video image data from the imaging camera 81 that identifies smiles segmentation for various face sizes and quantifies its rate. Other features may also be extracted using unsupervised deep learning methods, like convolutional autoencoders, that may extract latent features that describe a baby's state at time of the measurement. These autoencoders may be pre-trained on multi-baby baby dataset queried, for example, from one or more databases 112 stored in the one or more electronic resources 110, data from a plurality of babies with specific meta-features that characterize each baby from the plurality of babies.

In some embodiments with regard to a time driven data pipeline 250, the processor 60 may collect features using the features generated by the physics algorithm pipeline, such as the baby-specific 225 and environmental-specific 230 meta-features, and actions related to the environment (e.g., general environment features 255). The time driven data pipeline 250 may generate a time series $X\_(i-n)$, $X\_(i-n+1)$, ..., $X\_(i)$ for each feature $X\_(i)$ where n represent the $n^{th}$ measurement prior to measurement i. (Note that the time driven pipeline module 67 of FIG. 1 is equivalent to the time driven data pipeline 250 block of FIG. 5A.) For the time series for each feature, the time driven pipeline 250 may calculate time dependent (TD) features 270 that characterize feature statistics over time and feature progression. The time-dependent baby-specific features may include the baby-specific features exhibiting a time dependence, such as breathing rate, heart rate, etc. with the exception of the baby static features 245 in FIG. 5A. Similarly, the time-dependent environmental-specific features may include the environmental-specific features exhibiting a time dependence (e.g., time of day, weather, humidity, air pressure, etc). The TD features may be calculated using basic arithmetic operations, like mean, variance, max, min, or percentile (x) of the feature over a window of k recordings. The TD features 270 may be calculated using advanced signal processing functions like calculating probability gradients for n windows in time and taking the maximum (or minimum) gradient. The TD features may also be calculated using sensor fusion algorithms, for example baby motion features relative to environmental-specific features (such as environment sound, light, etc.).

In some embodiments, a baseline 265 may be generated that characterizes a baby state given available information, including actions that were applied to the environment of the baby (e.g., a collection of features 240 and 245, TD features 270, actions 235, and environmental-specific features 255 that reflect a specific window of time). This baseline 265 may be calculated using parametric configuration, such as using k features and TD features 270 for a specific window or the base line 265 be calculated using advanced ML approaches such as deep autoencoder that encode k features and TD features to a specific state for a specific window, or a variational autoencoder that learns the baseline probability density function per specific window. The output of the time driven pipeline 250 may then be relayed to a behavior model pipeline 275 and in addition is being stored in the history bucket (e.g., the feature history 260).

In some embodiments, a behavior model 275 pipeline may collect the output data of the previous data pipelines (features, TD features 270, baseline 265 signature, metadata and actions taken on the environment) to model the behavior of the baby 15. Note that the behavior model 68 module FIG. 1 is equivalent to the Behavior model 275 block of FIG. 5A. The behavior model 275 may generate a model that describes the mental, emotional, and behavioral states of the baby 15 given external conditions (such as environmental states. movie, sound, light, or other external states such as food consumed, time for breastfeeding, etc.).

In some embodiments, the behavioral models may include sub-models such as a stress level model (based on the baby's motion, heart rate (HR), heart rate variability (HRV), cry sound, etc.), a happiness characteristic model (based on smiles patterns, HR, HRV, and sound), sleep characteristic model (total sleep time, time during each sleep mode, number of times of being awakened, etc), and the like. The behavior model 275 may be trained using the input data of the pipeline, and data from a plurality of babies with similar baby-specific characteristics (such as similar age, gender, similar environment characteristics, etc). The behavior model 275 may be built using a supervised approach where the data is trained versus behavior characteristics, or an unsupervised approach where encodes all features to a single state that defines baby behavior.

Figure 5B:
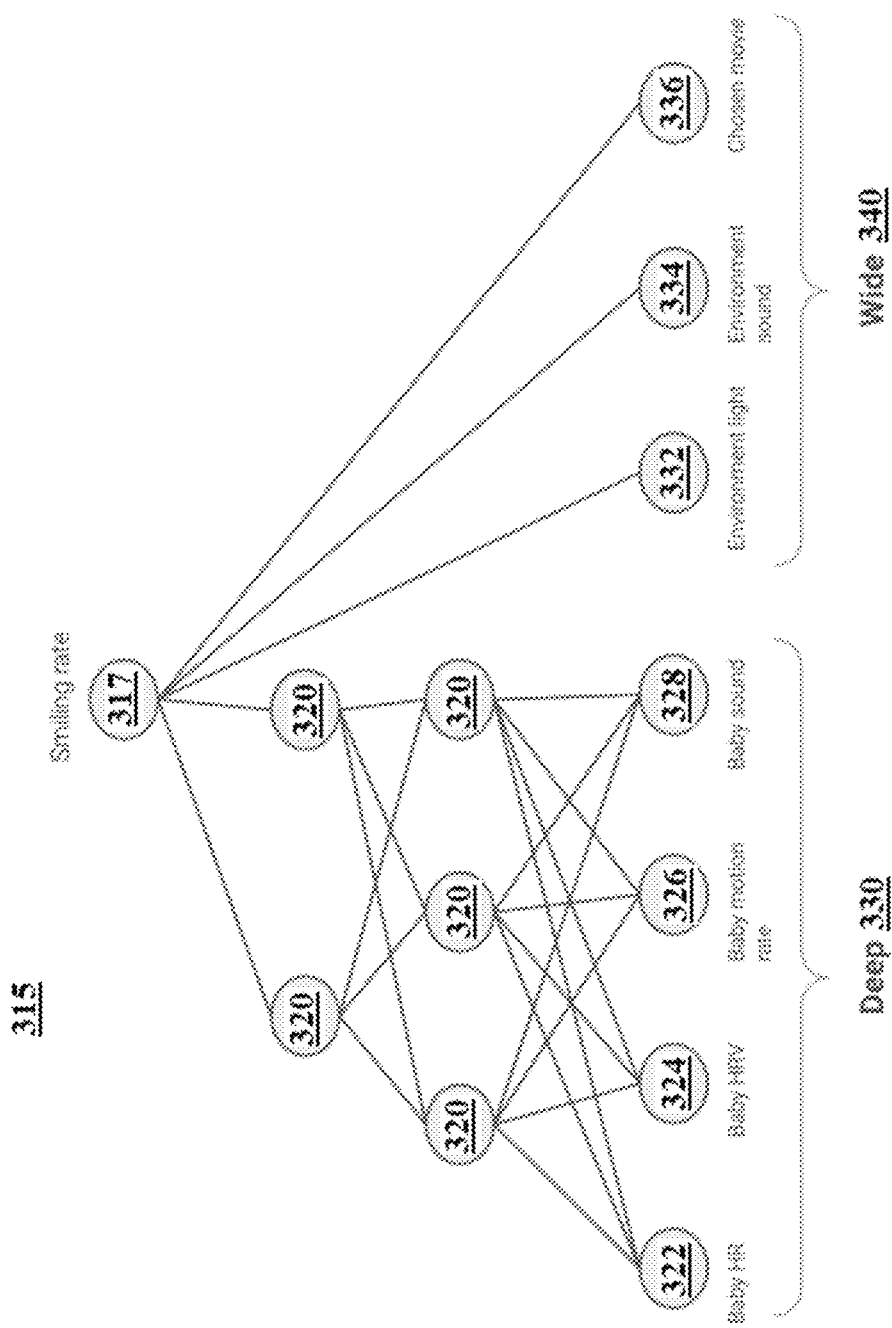
FIG. 5B illustrates an exemplary wide and deep neural network model to model a smiling rate of a baby in accordance with one or more embodiments of the present disclosure.

FIG. 5B illustrates an exemplary wide 340 and deep 330 neural network model 315 to model a smiling rate (node 317) of a baby in accordance with one or more embodiments of the present disclosure. Example of development of such model is taking a wide and deep neural network 315 where the dataset used for training the network is the features, time dependent features, environmental meta features and actions taken, and then training the wide and deep model in a supervised approach against the smiling rate of the baby (with a mean square error (MSE) loss function, for example). In this way, the model may correlate between environmental states (nodes 332, 334, and 336) and happiness characteristics (e.g., the smiling rate of node 317) so later the environmental states may be tuned to improve happiness. Using a wide and deep architecture 315 may capture the importance of environmental parameters on the baby behavioral state. Since the baby 15 is constantly growing and changing, a portion of the training data may include specific baby data and data for similar babies from a plurality of babies which is changing over time to maximize the baby's behavioral and/or emotional state.

In some embodiments with regard to a feedback environment generator 300, the feedback environment generator 300 may compile the user configuration 309 that may be entered via the GUI 55 of the mobile device, for example, by the user 45 (e.g., setting the use case such as soothing, feeding, and/or education) with a digital twin baby 290. The digital twin baby 290 may capture all behavior models 275 and baby-environmental configurations to provide actions based on the baby's environment. The digital twin baby 290 may be a set of parameters representing the baby's different responses to different stimuli when the baby is in different behavioral states taken at different time intervals. The digital twin baby and the user configuration 309 may be inputted to the feedback environment generator 300

In some embodiments, the feedback environment generator 300 may output a notification, an action, a recommendation, or any combination thereof so as to change the behavioral state of the baby over time to a desired behavioral state (predefined behavioral state) based on the use case. The behavioral states may include for example an agitated state, a calm state, a sleep state, a hungry state, a satiated state, a stress state, a playful state, a non-educated state on a particular subject, an educated state on a particular subject etc. For the soothing use case, the baby's behavioral state may be changed from an agitated state to a calm state (the desired behavioral state). For the feeding use case, the baby's behavioral state may be changed from a hungry state to a satiated state (the desired behavioral state) via the user's action in feeding the baby in response to the system automatically preparing the foodstuff (e.g., warming the baby's milk, for example). For the education use case, the baby's behavioral state may be changed from a non-educated state on a particular subject to an educated state on the particular subject (the desired behavioral state).

In some embodiments, examples of actions outputting from the feedback environment generator 300 may be, for example, reducing/increasing the intensity of light, changing light color, playing a sound (like a voice of a mother, a family member, a woman, a man, or a song, or any other source of digital sound), projecting a movie on the ceiling, do nothing, stop the current action, etc. Outputted notifications may include sending a notification such as an alert to the user 45 on GUI 55, for example that the baby is hungry. Outputted recommendations may include to do nothing, stop current action, or change the baby's education curriculum. This may be implemented by using the behavioral model function and optimizing it to a user requested state (e.g., to soothe the baby). The optimization may be done using a minimization of loss function on baby cry features, or baby motion features, or any other behavioral characteristic generated by the behavioral model 275. This process of implementing actions, is repeatedly and iteratively so as to change the state of the baby may be done until the loss function reaches an equilibrium (as defined by the model). The iterative processing may be applied using arithmetic functions, ML model, or reinforcement learning techniques with stochastic parameters added to produce a couple of paths for minimization.

In some embodiments, the algorithmic flow diagram 200 of the computer-based system for monitoring and interacting with a baby may tailored for each of the use cases described herein such as feeding the baby, soothing the baby, or educating the baby based on the training the different models using a training dataset with the input-output data features for each of the use cases as shown, for example, in the exemplary embodiments of FIGS. 4A-4B. The input data features may be the baby-specific features 225 and the environmental-specific features 230 of FIG. 5A that are mapped to the actions 302 and/or IoT Activation 308 based on the output of the feedback environmental generator 302. Examples of the baby-specific features 225 as shown in FIG. 5A may include but are not limited to breathing detection (breathing rate), Heart rate (heartbeat signal data), baby voice (baby voice classification data), baby temperature as shown in inputs 163 and 174 of FIGS. 4A and 4B.

In some embodiments, the baby-specific behavioral state detection machine learning model and/or the baby-specific educational machine learning model may be any suitable machine learning model that may be trained for a specific use case using datasets as shown for example in FIGS. 4A and 4B.

In some embodiments, the baby-specific behavioral state detection machine learning model and/or the baby-specific educational machine learning model may incorporate the functionality of the time driven pipeline 250, the behavioral models 275, and the feedback environment generator 300 such that the baby-specific features 225 and the environmental-specific features 230 are mapped into the actions 302 specific to each use case. Stated differently, for each use case (e.g., soothing, feeding, and education), the blocks shown in the algorithmic flow diagram 200 may be used to generate the use-case specific training datasets for training the baby-specific behavioral state detector machine learning model and/or the baby-specific educational machine learning model.

In some embodiments, the baby-specific behavioral state detector machine learning model and/or the baby-specific educational machine learning model may be implemented using any suitable machine learning model such as a classification neural network model, long-short term memory (LSTM) model, convolutional neural network, and/or a multi-class neural network, for example. They may be trained with the training dataset for the particular use case.

In some embodiments, a baby-specific behavioral state detector machine learning model may be used for the soothing and feeding use case. The baby-specific behavioral state detection machine learning model in the soothing use case may map the baby-specific and environmental-specific features into actions such as for example but not limited to generating by the speaker 16, a soothing sound for the baby when the baby is determined to be agitated, to generate by the speaker 16, a sleep-enhancing sound when the system detects that the baby is about to wake-up (so as cause the baby to fall back asleep), and/or to project via a projection device (e.g., the projector 18), a relaxing image to be viewed by the baby. For the feeding use case, the baby-specific behavioral state detection machine learning model in the feeding use case may map the baby-specific and environmental-specific features into actions, such as for example, but not limited to changing the temperature of the foodstuff temperature controller 35 when detecting that the baby 15 is hungry so as to prepare the foodstuff such as the baby's milk in the bottle 32 for feeding the baby.

In some embodiments, a determination that the baby is hungry may include considering time periods in which the baby eats (e.g., every three hours for example), the last time the baby ate and observing that in a time interval before the baby is fed, the baby may exhibit certain movements. This data may be acquired for example over a plurality of babies and for the baby 15 that may be used in training the AI-models such that when the baby 15 exhibits similar movements in a predefined time after the baby last ate, the actions 176 by the AI-model may be to send an alert 140 (user notification) on the GUI 55 on the mobile device 50 of the user 45, for example, that the baby's food is being prepared (FIGS. 2B and 2C), or simply that the baby is hungry. The determination that the baby is hungry may include considering the movement rate, the breathing rate, time of the day, user configuration (user feedback) (such as the user indicating on GUI 55 that the baby was fed 2 hours ago, or that the baby needs to gain weight), baby age, weight, height, for example.

In some embodiments, an identification by the system 5 that the baby is sleeping and/or may be about to wake up and/or has already awakened may include acquiring image and/or audio data for movement and/or skeleton detection, and/or voice classification for the baby 15 and/or for each baby in the plurality of babies. This data may be used in training the AI-models to identify that the baby is agitated and/or about to wake up.

In some embodiments, the feedback environment generator 69 may be trained using data from the plurality of babies as to which audio stream (tune), audio volume, equalizer parameter succeeded in soothing the baby. Soothing the baby as referred to herein may be the iterative process of playing a soothing sound or an audio stream to the baby and/or relaxing images to project to the baby (e.g., the visual image 25 of the rabbit, for example) that causes the baby to calm down and/or fall back asleep. This may be assessed by the AI model from the movement data detected from the image data of the image camera indicating smaller movements and/or the audio data indicating that there is no crying and/or the baby may be determined to have fallen back to sleep, for example. In other embodiments, in the same vein, a sleep-enhancing sound may be any audio stream determined to cause the baby to fall back asleep when the baby is awake or is about to wake up as predicted by any of the AI-models. The AI-model may be trained to output any projection features shown in the output features 165.

In some embodiments, the AI-model may be trained to output a type of vibration (vibration intensity and/or vibration rhythm) for the vibration unit 40 to apply to the baby so as to soothe the baby as described above.

In some embodiments, the baby-specific educational machine learning model for the educational use case when subjecting the baby to a baby-specific educational plan may map the baby-specific and environmental-specific features into actions such as outputting an indication that the baby understood or did not understand a visual image and a sound associated with the visual image based on the baby-specific educational plan as shown for example for the rabbit image shown in FIG. 2D, or may output a baby-specific educational recommendation such as to modify the baby-specific educational plan if it is too hard for the baby or the baby is bored when the baby may be detected to be bored, for example.

In some embodiments, the actions 302, (e.g., environmental changes experienced by the baby 15 shown in the outputs 165 and 176 in FIGS. 4A and 4B, for example) that are predicted by the baby-specific behavioral state detection machine learning model and/or the baby-specific educational machine learning model after training with the training datasets as generated in the algorithmic flow of FIG. 5A as defined above, may be performed iteratively so as to change the baby's behavioral state in accordance with goals of the specific use-case. For example, for the soothing use case, the baby may experience one or more environmental changes by the system 5 performing any of the actions as shown, for example, in list of outputs 165 in FIG. 4A, within a predefined time interval until the baby's behavioral state changes from an agitated state to a calm state (or falls back asleep).

In some embodiments, the machine learning models may dynamically change parameters in the actions until the until the baby's behavioral state changes from an agitated state to a calm state (or falls back asleep). For example, the parameters of the action (e.g., the soothing sound) such as changing an audio file, changing the BPM in the audio, changing the volume, changing the audio stream, and/or changing the equalizer parameters may occur multiple times in the predefined interval based on the changing output of the baby-specific behavioral state detection machine learning model.

Figure 6A:
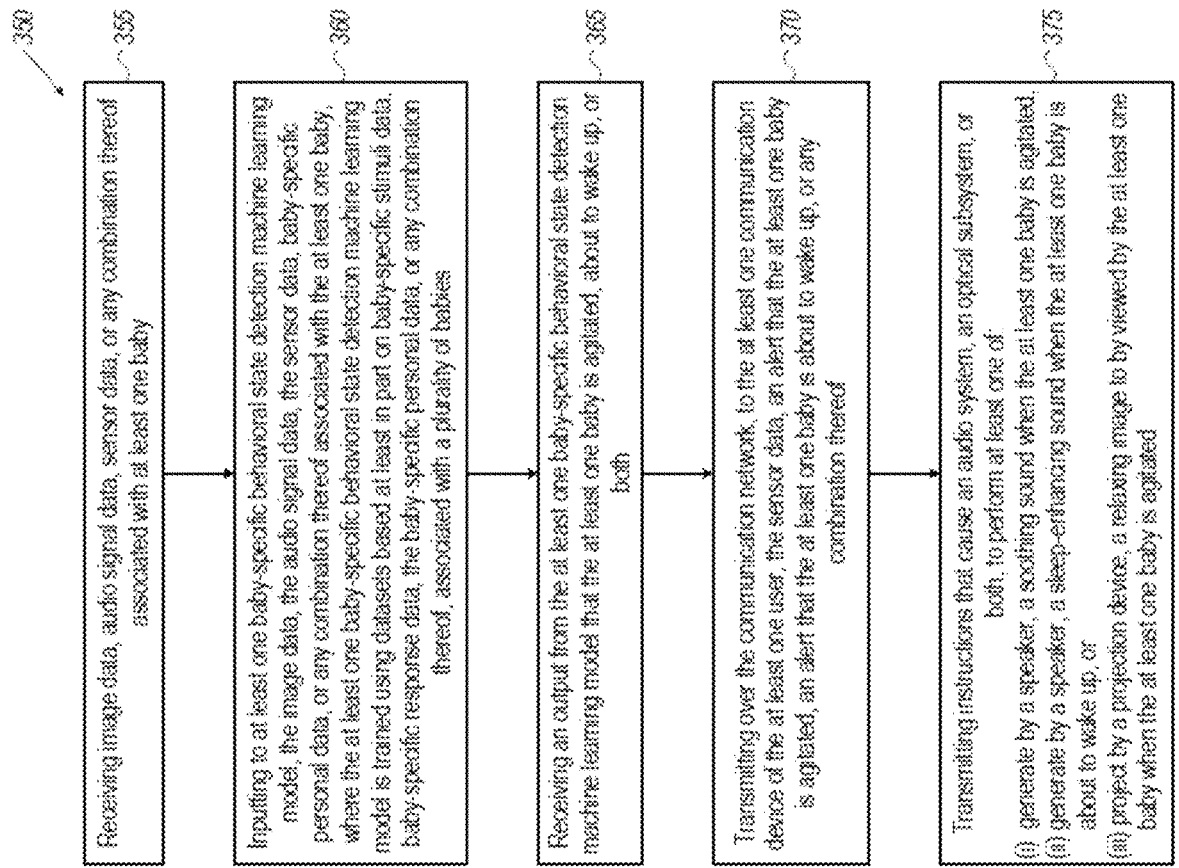
FIG. 6A is a flowchart of a method for soothing a baby in accordance with one or more embodiments of the present disclosure.

FIG. 6A is a flowchart of a method 350 for soothing the baby 15 in accordance with one or more embodiments of the present disclosure. The method 350 may be performed by the processor 60 and the elements of the BMID 10 in the system 5.

The method 350 may include receiving 355 image data, audio signal data, and sensor data associated with at least one baby.

The method 350 may include inputting 360 to at least one baby-specific behavioral state detection machine learning model, the image data, the audio signal data, the sensor data, and baby-specific personal data associated with the at least one baby, where the at least one baby-specific behavioral state detection machine learning model is trained using datasets based at least in part on baby-specific stimuli data, baby-specific response data, baby-specific personal data associated with a plurality of babies.

The method 350 may include receiving 365 an output from the at least one baby-specific behavioral state detection machine learning model that the at least one baby is agitated, about to wake up, or both.

The method 350 may include transmitting 370 over the communication network, to the at least one communication device of the at least one user, the sensor data, an alert that the at least one baby is agitated, an alert that the at least one baby is about to wake up, or any combination thereof.

The method 350 may include transmitting 375 instructions based on the output that cause an audio system, an optical subsystem, or both, to perform at least one of:
 (i) generate by a speaker, a soothing sound when the at least one baby is agitated,
 (ii) generate by a speaker, a sleep-enhancing sound when the at least one baby is about to wake up, or
 (iii) project by a projection device, a relaxing image to by viewed by the at least one baby when the at least one baby is agitated.

Figure 6B:
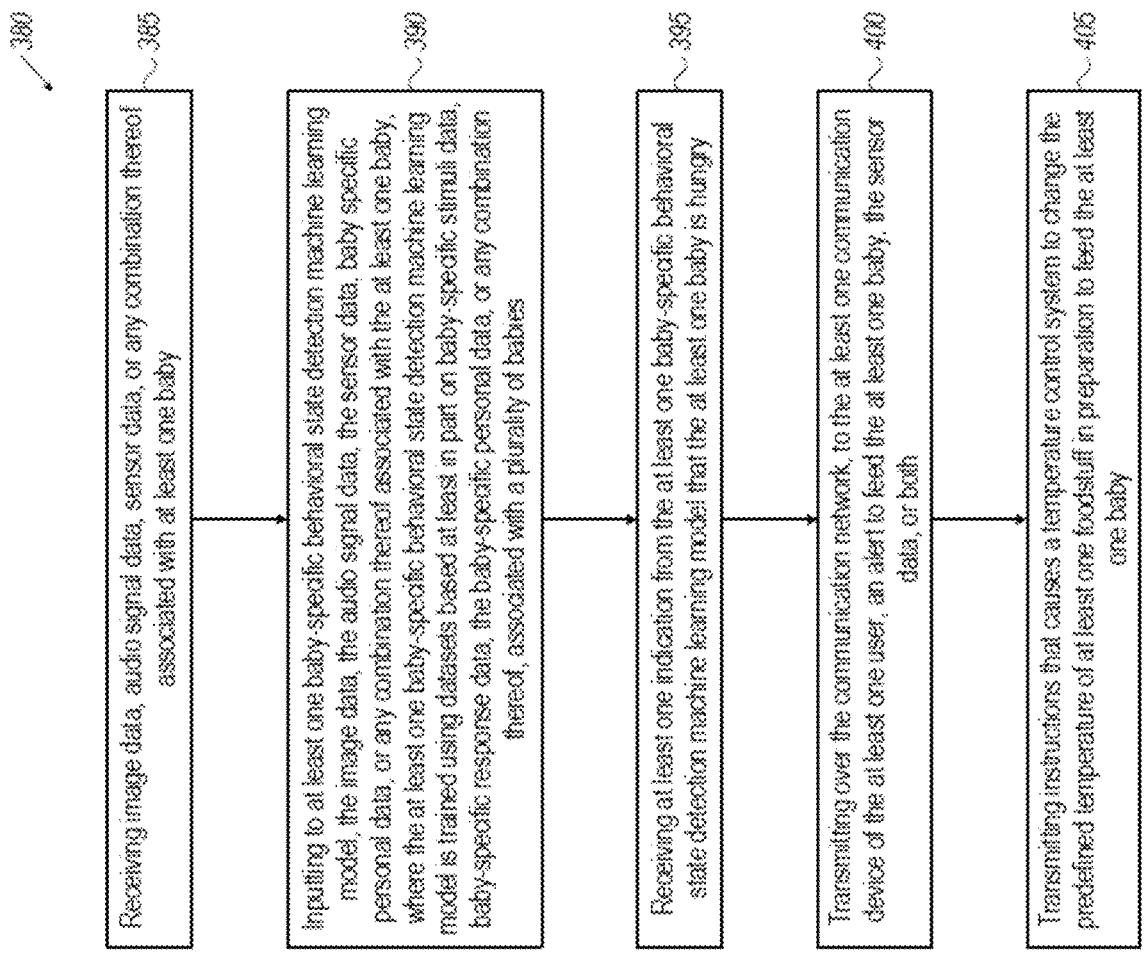
FIG. 6B is a flowchart of a method for feeding a baby in accordance with one or more embodiments of the present disclosure.

FIG. 6B is a flowchart of a method 380 for feeding the baby 15 in accordance with one or more embodiments of the present disclosure. The method 380 may be performed by the processor 60 and the elements of the BMID 10 in the system 5.

The method 380 may include receiving 385 image data, audio signal data, and sensor data associated with at least one baby.

The method 380 may include inputting 390 to at least one baby-specific behavioral state detection machine learning model, the image data, the audio signal data, the sensor data, and baby specific personal data associated with the at least one baby, where the at least one baby-specific behavioral state detection machine learning model is trained using datasets based at least in part on baby-specific stimuli data, baby-specific response data, baby-specific personal data associated with a plurality of babies.

The method 380 may include receiving 395 at least one indication from the at least one baby-specific behavioral state detection machine learning model that the at least one baby is hungry.

The method 380 may include transmitting 400 over the communication network 30, to the at least one communication device 50 (e.g., the mobile communication device 50) of the at least one user, an alert to feed the at least one baby, the sensor data, or both.

The method 380 may include transmitting 405 instructions that causes a temperature control system 35 to change the predefined temperature of at least one foodstuff in preparation to feed the at least one baby.

Figure 6C:
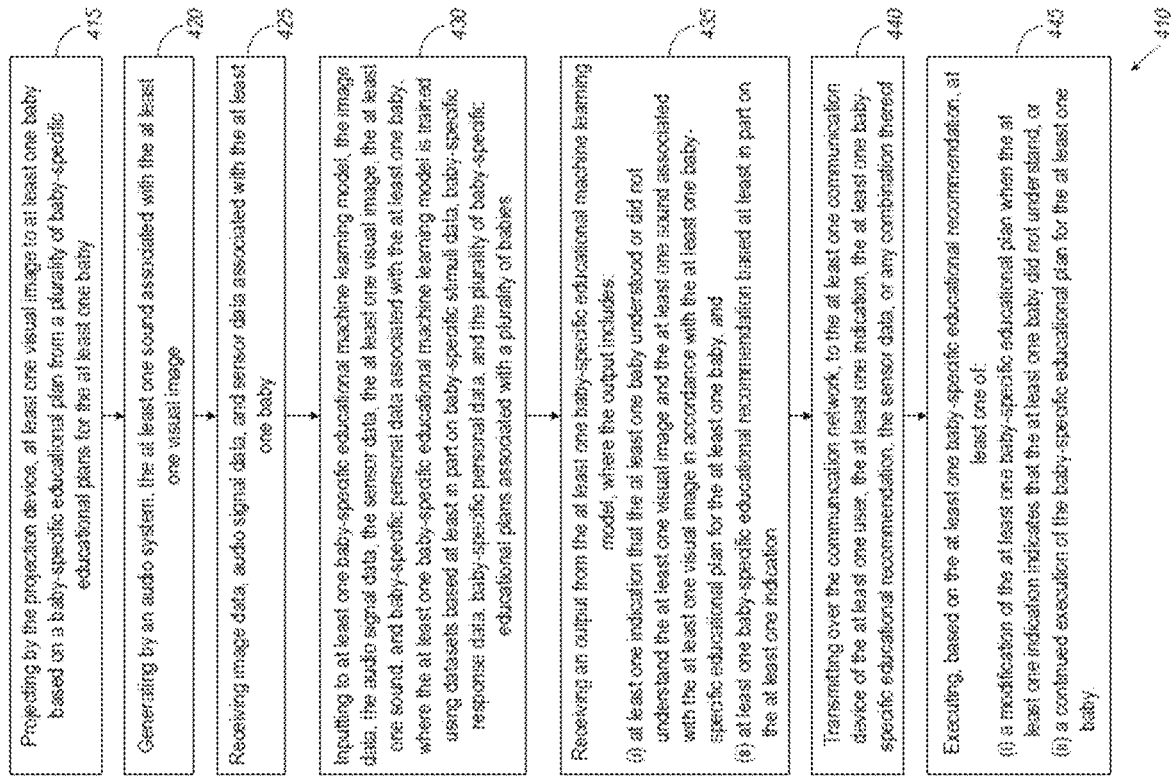
FIG. 6C is a flowchart of a method for educating a baby in accordance with one or more embodiments of the present disclosure.

FIG. 6C is a flowchart of a method 410 for educating the baby 15 in accordance with one or more embodiments of the present disclosure. The method 410 may be performed by the processor 60 and the elements of the BMID 10 in the system 5.

The method 410 may include projecting 415 by the projection device, at least one visual image to at least one baby based on a baby-specific educational plan from a plurality of baby-specific educational plans for the at least one baby.

The method 410 may include generating 420 by an audio system, the at least one sound associated with the at least one visual image.

The method 410 may include receiving 425 image data, audio signal data, and sensor data associated with the at least one baby.

The method 410 may include inputting 430 to at least one baby-specific educational machine learning model, the image data, the audio signal data, the sensor data, the at least one visual image, the at least one sound, and baby-specific personal data associated with the at least one baby, where the at least one baby-specific educational machine learning model is trained using datasets based at least in part on baby-specific stimuli data, baby-specific response data, baby-specific personal data, the plurality of baby-specific educational plans associated with a plurality of babies. The at least one sound generated by the speakers may be the soothing sound, the sleep enhancing sound, or the sounds associated with the projected visual image such as a cat's meow for the visual image of a cat, the voice of a person saying the word "cat".

The method 410 may include receiving 435 an output from the at least one baby-specific educational machine learning model, where the output includes:
(i) at least one indication that the at least one baby understood or did not understand the at least one visual image and the at least one sound associated with the at least one visual image in accordance with the at least one baby-specific educational plan for the at least one baby, and
(ii) at least one baby-specific educational recommendation based at least in part on the at least one indication.

The method 410 may include transmitting 440 over the communication network, to the at least one communication device of the at least one user, the at least one indication, the at least one baby-specific educational recommendation, the sensor data, or any combination thereof.

The method 410 may include executing, based on the at least one baby-specific educational recommendation, at least one of:
(i) a modification of the at least one baby-specific educational plan when the at least one indication indicates that the at least one baby did not understand, or
(ii) a continued execution of the baby-specific educational plan for the at least one baby.

Figure 7A:
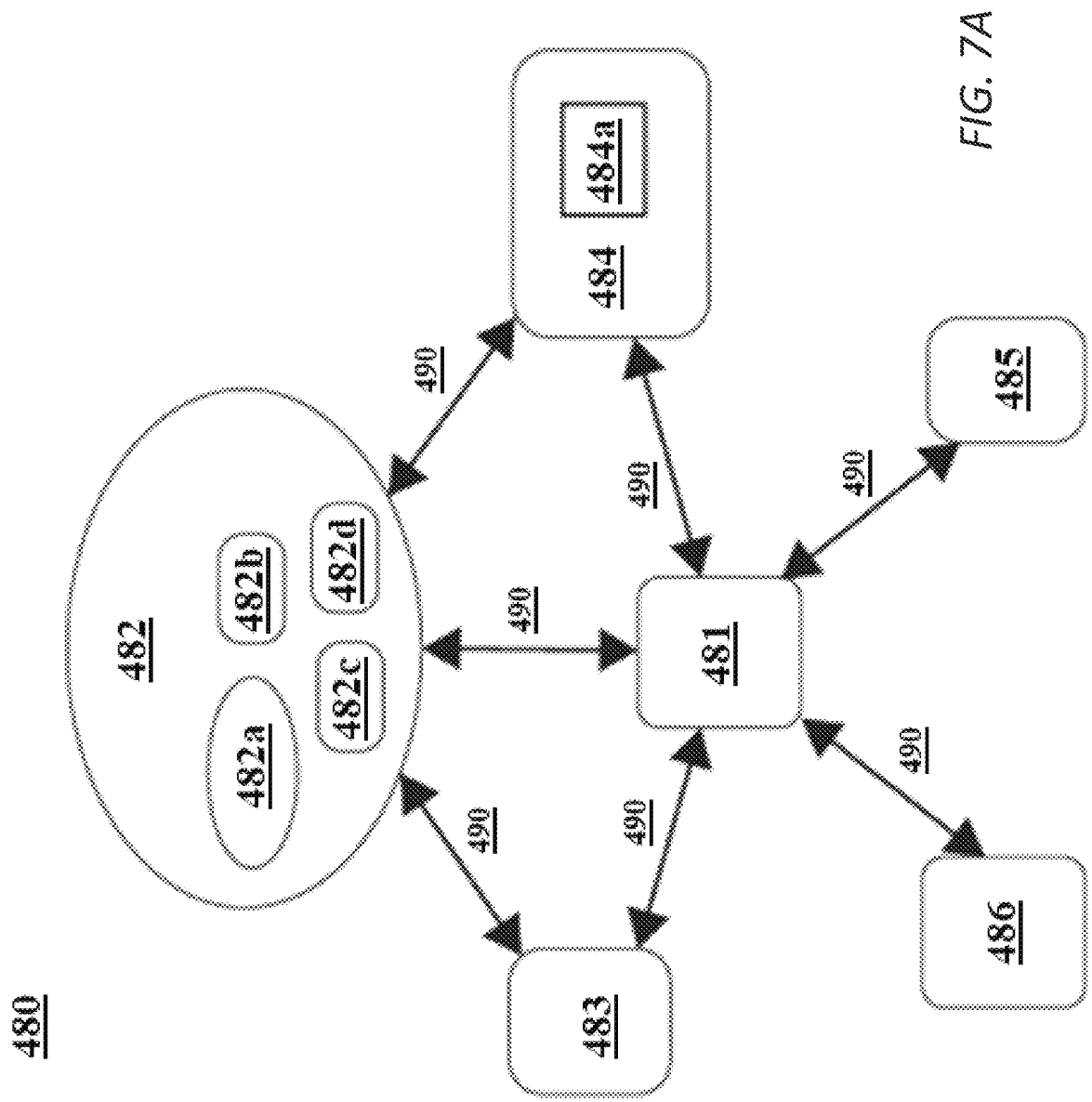
FIG. 7A illustrates a second exemplary embodiment of a computer-based system for monitoring and interacting with a baby in accordance with one or more embodiments of the present disclosure.

FIG. 7A illustrates a second exemplary embodiment of a computer-based system 480 for monitoring and interacting with a baby in accordance with one or more embodiments of the present disclosure. The system 480 may include a monitor 482, a processing unit 481, a mobile application (user interface) 486 and a temperature control subsystem 485. The monitor 482 may be mounted on a wall or ceiling, or it may be mounted to a piece of furniture such as a crib, for example. Note that elements from system 480 may be used interchangeably with the elements of system 5 of FIG. 2

In some embodiments, the monitor 482 may include a base station inlet for connection (490, double headed arrows) to accessories. In other embodiments, there may not be a base station inlet. Typically, the monitor unit includes a processing unit. Communication connectivity may be wired or wireless.

In some embodiments, the monitor 482 may be connected to devices such as an optical subsystem 482a, a two-way audio system 484, a projector 483, a microphone and acoustic/audio detector 484a, a breathing detector 482d, a temperature detector 482b, a heart rate detector 482c, a user interface 486, a temperature controller 485, a processing unit 481, a weighing scale (not shown), a lidar sensor (not shown), or any combination thereof.

In some embodiments, the processing unit 481 may be located within the monitor 482, in a unit separate from the monitor 482, in the cloud, or any combination thereof. The processing unit may include software, hardware, or any combination thereof configured to store data, convert sensor signals to sensor signal data, extract visual data from visual patterns, extract audio data from audible patterns, execute machine learning models using the visual and/or audio data as input, or any combination thereof.

FIG. 7B illustrates a diagram of the data elements for an infant condition description vector (ICDV) in accordance with one or more embodiments of the present disclosure. The ICDV may be an output of the behavioral model 275 as shown in FIG. 5A.

In some embodiments, the AI-based system may generate an infant condition description vector (ICDV). The ICDV may include a historic and current representation of the baby's emotional status. The ICDV may include current sensor data and a history of the Infant (IH). Current sensor data may include data from many sensors, may be processed or raw data, may be a continuation of immediate history data, or any combination thereof. Typically, the sensor data may be processed into different signals of interest, such as for example a heartbeat signal. The new data may be concatenated to the previous data, thus forming a continuation of immediate history data.

The infant history (IH) may include 3 parts:
a. Bio history (IBH) data that may include baby-specific personal data such as the baby's age, physical characteristics (such as for example height, weight, head size, etc.) and developmental stage (such as for example movement capability, communication level, sleep ability, melatonin state estimation, etc.)
b. Infant personal history data (IPH) may include baby-specific historic responses to the reaction loop, generated from historic data specific to this baby.
c. Infant crowdsourcing historic data (ICH) may include a historic weighted average of the responses of other babies (e.g., data from a plurality of babies), taking into consideration the IBH and IPH of the other infants. The infant crowdsourced data can be from other babies using the system, from laboratory experiments, and any combination thereof.

In some embodiments, the ICH may include baby-response data for a plurality of baby-specific responses acquired in response to a plurality of baby-specific stimuli provided to a plurality of babies. The ICH may include baby-specific stimuli data for the plurality of baby-specific stimuli provided to a plurality of babies. The ICH may include baby-specific personal data for each baby in the plurality of babies.

FIG. 7B illustrates an exemplary embodiment of an ICDV where the current sensor data may be algorithmically processed to generate a breathing waveform 521, a temperature map 522, a sleep status 523 (e.g., asleep, awake, drowsy, waking, etc.), a crying level 524 (not crying, whimper, continuous crying, intermittent crying, loud crying, soft crying, etc.), a heart rate 525 and other baby-specific historic responses 526 as disclosed herein.

In some embodiments, the IBH may include a movement level 531, a communication level 532 and more 533 baby-specific data of the baby 15.

In some embodiments, the IPH may include an audio response history 541, a projector response history 542 may include the baby's responses to projected images and/or sound, and more 543 baby-specific data of the baby 15.

In some embodiments, the ICH may include the same type of data as the IPH, namely an audio response history 551, a projector response history 552 that may include the baby's responses to projected images and/or sound, and more 553 baby-specific data of each baby in the plurality of babies, e.g., crowdsourced baby-specific data.

Figure 7C:
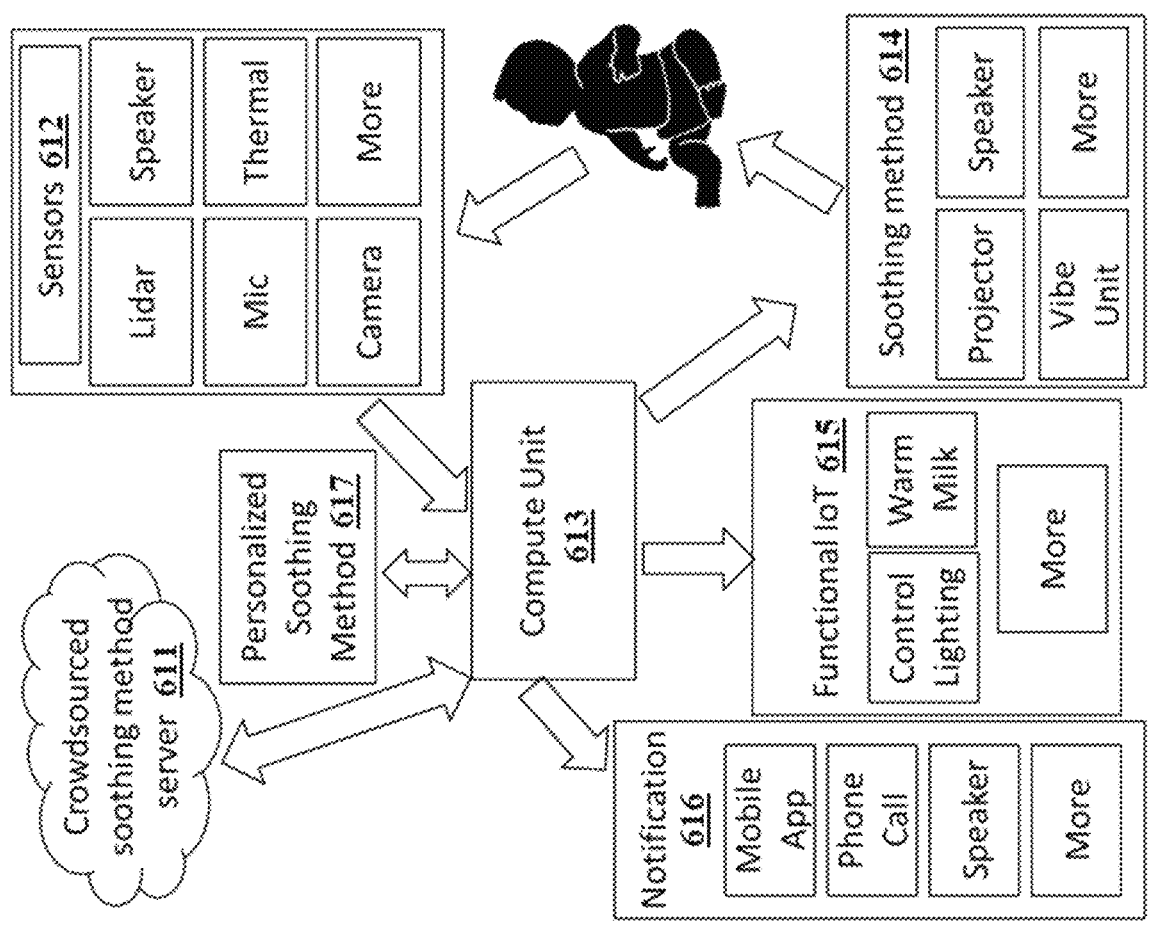
FIGS. 7C and 7D illustrate exemplary embodiments of a detection reaction loop for soothing a baby in accordance with one or more embodiments of the present disclosure.
Figure 7D:
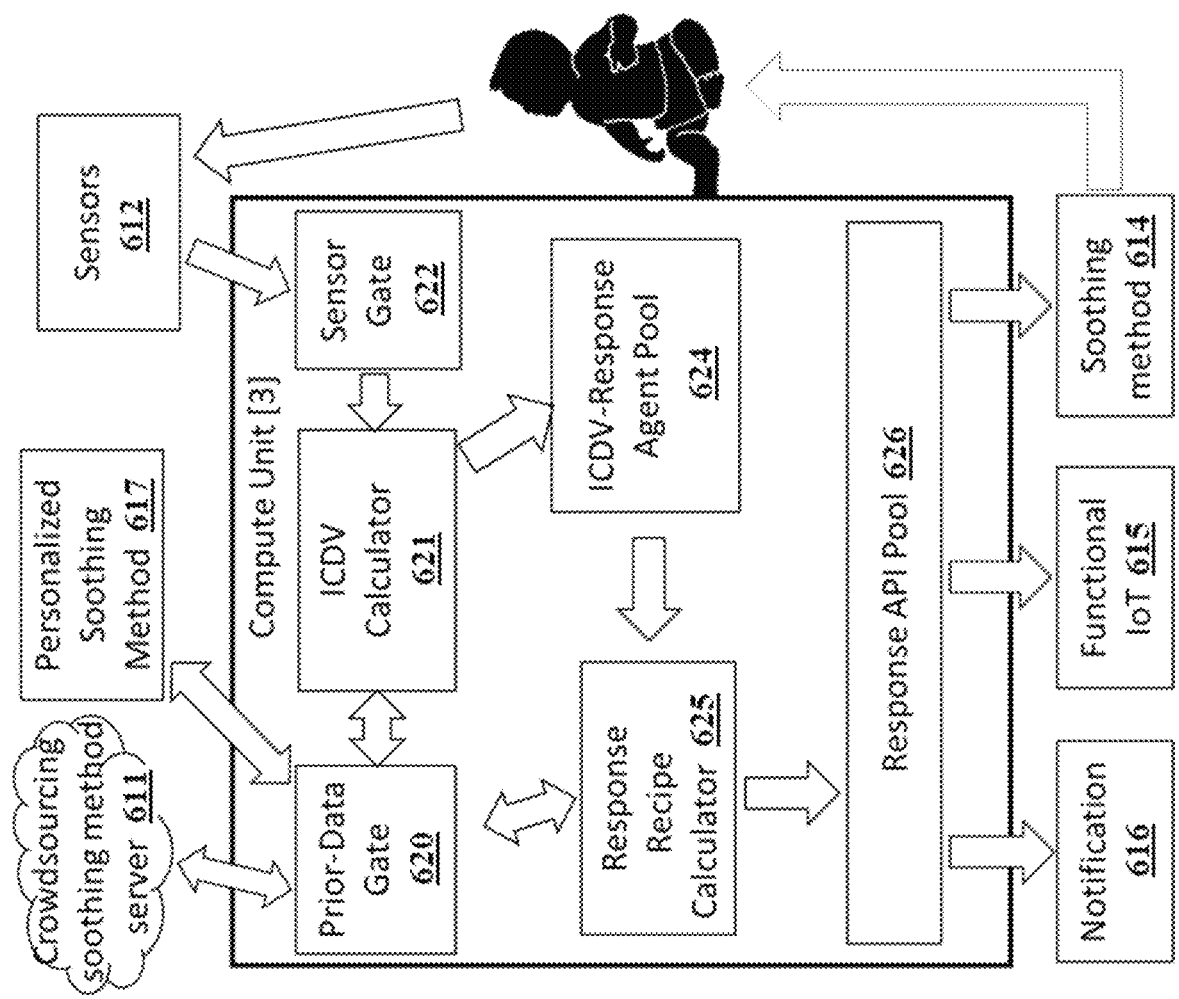

FIGS. 7C and 7D illustrate exemplary embodiments of a detection reaction loop for soothing a baby in accordance with one or more embodiments of the present disclosure. The detection reaction loop may be performed by the system 480 or the BMID 10.

The detection reaction loop for soothing a baby may include the steps of:

I Detection
  A. Set up an embodiment of the system 480 that includes a soothing method decision-making component (AI/machine learning). The soothing method decision-making component may be preloaded into the system and used only locally or may include at least one parameter from a crowdsourcing soothing method server 611. Stated differently, the system 480 may use at least one machine learning model such as in the algorithmic flow diagram 200 of FIG. 5A that has been trained for the soothing use case.
  B. Collect data from multiple sensors 612 such as for example, an optical subsystem, a microphone, an acoustic/audio detector, a temperature detector, a user interface, a temperature controller, and/or a lidar. Note that breathing detection and the heart rate detection may be determined from the sensor data from the image camera, RF sensor, and/or thermal sensor to use algorithms to assess if the baby is breathing and/or to detect heart rate of the baby. The breathing and heart rate algorithms will be discussed hereinbelow.
  C. Transfer data to the Computation Unit 613, which may be part of the camera computation processor, can be part of a separate processor, and any combination thereof, to analyze the data and to determine if the baby is not soothed or is about to wake up.
  D. The Computation Unit then may perform the following steps (see FIG. 7D):
  i. Receive historic data from the Prior-Data Gate 620.
  ii. Receive the sensor data from the Sensor Data Gate 622 and analyze the raw data.
  iii. In the ICDV Calculator 621, generate from the analyzed data, inputs for all of the response systems (audio, video, alert, etc)
  iv. Transmit the result to the ICDV-Response Agent Pool 624. The ICDV-Response Agent Pool 624 may include a computation agent, which can be one agent per response system, one agent for many response systems, many agents for at least one response system, or any combination thereof. The ICDV-Response Agent Pool 624 may generate, from the analyzed sensor data, several ICDV values, which may be weighted using predefined or AI-generated weights to determine the relative importance of the generated ICDV values.
  v. The results from each agent may be relayed to the Response Recipe Calculator 625 to generate an action list for each response system and to transmit it through the Response API Pool 626, as well as to update the actions, the IPH and the ICH through the Prior-Data Gate 620.

II Reaction/soothing
  E. Activate at least one of the following functions:
  a. Activate a soothing method 614
    i. Soothing by sound from the speaker such as for example, music, white/pink noise, a user's voice, or any combination thereof. The voice may be recorded, live or both although, typically, a recorded voice message may be used. The volume, type of sound and length of time the sound is emitted may be varied, depending on the baby's reaction.
    ii. Activate the projector and display a soothing video.
    iii. Activate a vibration unit.
  b. Activate a functional IoT device 615
    i. Activate a foodstuff temperature controller 35 to warm-up, for example, a foodstuff, typically a bottle of milk.
    ii. Control an ambient light (e.g., the illumination lamp 27) such as for example, turning a light on or off, adjusting a lighting level, and/or change the color of a light.
    iii. Activate another IoT device.
  c. Send a notification to a user 616
    i. Send the notification via a mobile application (e.g., display on the GUI 55 of the mobile device 50), for example, an app, a built-in OS notification, or any combination thereof
    ii. Send the notification by a phone call (e.g., to the mobile device 50).
    iii. Send the notification by sound from the speaker system (e.g., the speakers 16).
  F. Collect data from multiple sensors 612 such as for example, an optical subsystem, a microphone, an acoustic/audio detector, a breathing detector, a temperature detector, a heart rate detector, a user interface, a temperature controller, a lidar, or any combination thereof
  G. Based on the sensor data from step E, using AI, automatically modify the soothing method 617. H. Based on the modified parameters of step (E) and the results of step (F), repeat step D.
  I. Send the modified parameters to the crowdsourcing soothing method server 611 for modification of the generic soothing method decision-making component (AI\machine learning).

In some embodiments, the optical subsystem 482a may include both a visible-spectrum imaging detector (for daytime use) and an infrared imaging detector for night vision. In other embodiments, computer vision motion detection may also be used, either integrally with the optical system, as part of the processing unit, or any combination thereof.

In some embodiments, the two-way audio system 484 may be integral to the monitor, removably connected to the monitor, or a unit separate from the monitor.

In some embodiments, the projector 483 may be integral to the monitor, removably connected to the monitor, or a unit separate from the monitor.

In some embodiments, a removable speaker and a removable projector may be electrically charged (e.g., charging a battery) when connected to the monitor or may be charged separately.

In some embodiments, the user interface 486 may be integral to the monitor, may be a separate unit, or any combination thereof. In other embodiments, at least one user interface may be mobile. User interfaces may be for example a smartphone app, a telephone messaging system, a computer messaging system, the GUI 55, or any combination thereof. Examples of computer messaging systems may include an email messaging system, audible alerts, visible alerts, and/or a computer-based interface. A Smartphone app and a telephone messaging system may use audible alerts, visible alerts, tactile alerts, or any combination thereof, to inform a user of an incoming message, to provide a message, or any combination thereof.

In some embodiments, the temperature controller 485 (e.g., foodstuff temperature controller 35 from FIG. 1) may be configured to store feeding consumables and to keep the feeding consumables at a predefined temperature. The feeding consumables may be milk, either breast milk or a prepared manufactured infant milk (formula) or milk substitute, water for preparing formula or milk substitute, and/or a foodstuff. The feeding consumable may be kept cold until time of use and may be heated to an appropriate temperature at the time of use.

In some embodiments, either the temperature controller 485 or the processing unit 481 may determine from the behavior of the monitored person (e.g., the baby), that a feeding time is imminent, and may provide a mechanism for warming the milk to an appropriate temperature for use. In other embodiments, the system may include mechanism for alerting the user 45 (e.g, parent or other caregiver) that a feeding time is imminent such as via the GUI 55 on the mobile device 50. In yet other embodiments, the system may include a mechanism for determining that the parent or other caregiver may be approaching the monitored person (e.g., the baby) to feed the monitored person. Stated differently, the system 5 may monitor the distance D as shown in FIG. 1 that the user 45 may be approaching the baby 15.

In some embodiments, the temperature controller 485 may include both a heating and a cooling mechanism, such as for example a Peltier device for both heating and cooling, although separate heating and cooling devices may be used. Heating devices may include for example a Peltier system, an infrared heater, a heating mantle, a heating tape, a microwave, hot air, or any combination thereof. Cooling devices may include for example a Peltier system, a cooling mantle, cold air, a circulating cold liquid, evaporative cooling, or any combination thereof.

In some embodiments, the processing unit 481 may be integral to the monitor, may be a component separate from the unit, may be part of the cloud, or any combination thereof. The processing unit may collect, process data and may provide feedback from the collected data to subsystems, such as the temperature controller (e.g., the IoT activation 308 from FIG. 5A) and to a user (e.g., the user 310 from FIG. 5A).

In some embodiments, by collecting various data from the baby and its environment, the system 480 may provide personalized feedback on the baby to the user. The data collection performed by the monitor 482 and/or by other sources (for example, a speaker 484, a microphone 484a, a thermometer 482b and user input) may include, for example, monitoring breathing, acoustic and visual monitoring, heart rate and temperature monitoring, feeding schedule, sleep routine, signals of crying, and more. From these, the processor may determine, for example, breathing patterns and changes in breathing patterns, acoustic patterns and changes in acoustic patterns, movement patterns and patterns and changes in movement patterns, body temperature and changes therein, heart rate and changes therein, or any combination thereof.

In some embodiments, the processing unit 481 may continuously collect and process data for feedback in order to generate an automated personalized solution. Information gathered from the user may be used to activate various system functions to provide a custom-made solution for a variety purposes implementing the feeding, soothing, inducing sleep, and/or education use cases. The system 480 may be connected to a user-friendly user interface 486.

In some embodiments, information gathered from the user via the monitor may processed via the machine learning models/algorithms (e.g., the MLM/Algorithms 65 of FIG. 1). The processed information may be used to activate various system functions that may provide custom-made solutions for feeding, soothing, encouraging sleep, and/or education use-cases for example.

Figure 7E:
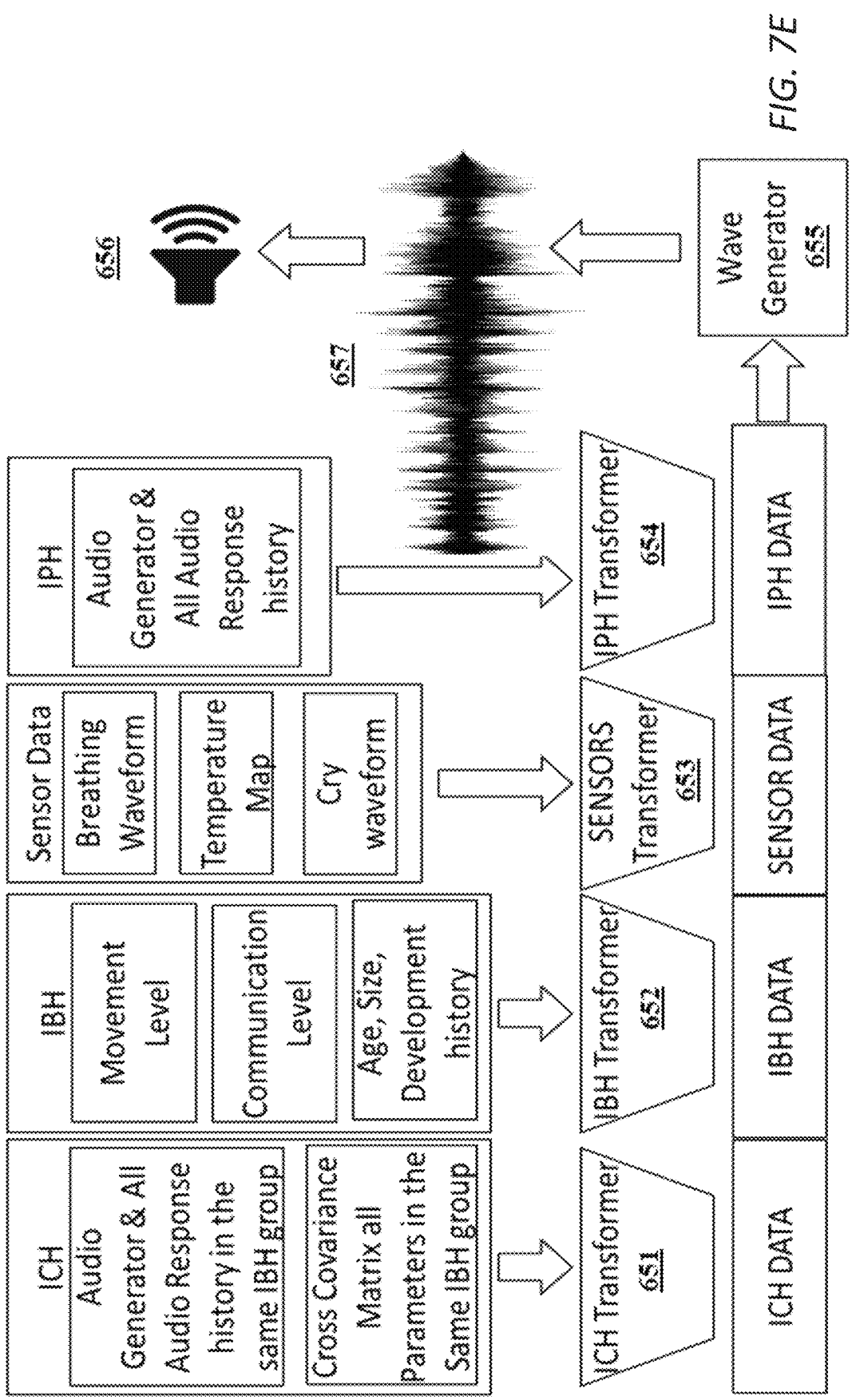
FIG. 7E schematically illustrates an embodiment of an audio generator response agent for a reaction soothing loop in accordance with one or more embodiments of the present disclosure.

FIG. 7E schematically illustrates an embodiment of an audio generator response agent for a reaction soothing loop in accordance with one or more embodiments of the present disclosure.

In some embodiments, the audio generator response agent may generate sounds to be played to the baby. The system may perform the following steps:

A. Receive data from the ICDV.
B. Build a representation of the ICDV from the data from transformers 651, 652, 653, 654, and based at least in part on:
  1. The baby's response history and appropriate waveforms found in the baby's response history.
  2. Response histories for other babies in the plurality of babies with approximately the same IBH and having similar audio waveforms found in the other babies' response histories.
  3. The baby's current response history, starting from the beginning of this soothing session.
  4. Responses from a predetermined number of soothing session histories. The predetermined number may be in a range from 0 to 100, in a range from 5 to 20, or the last 10 soothing sessions.
  5. Sensor data over a predetermined time previous to the current time. The predetermined time may be in a range from 0 to 2 hours, from 1 minute to 20 minutes, or the previous 5 minutes data. Typically, baby-specific parameters derived from the output sensor data may include any combination of the following:
    1. Breathing rate
    2. Heart rate
    3. Temperature
    4. Movement map
    5. Audio waveform, or
    6. Crying status
C. Generate a sound waveform from the ICDV representation 655 by steps of:
  a. Based on the sensor data and the IPH data, select the base waveform that will have the best soothing effect.
  b. Compare the base waveform to soothing waveforms from the ICH data and, if needed, to perform small changes to the waveform according to waveform history in the ICH.
D. Send the waveform generated in Step C to the speaker 656 which may play it to the baby, for example, if the baby has not fallen asleep after a predetermined time (in which case an alert may be sent to a user), or if a manual "stop" command is issued.
E. Measure the response of the baby (repeat steps A and B).
F. If the baby is in a steady sleep state, stop the process.
G. If the baby is approaching a steady sleep state but has not yet reached it, make small changes to the waveform 657 based on changes in the sensor data and how the changes in the sensor data have affected this baby (IPH) and other babies (ICH) from the plurality of babies.
H. Iteratively perform steps D-G until the process is stopped.

Note that the process above is exemplary and not by way of limitation such that steps may be carried out in a different order and/or more or fewer steps may be used.

Feeding/Bottle Preparation

In some embodiments, behavioral patterns and parameters of the baby's feeding routine may be determined from the baby's breathing and sleeping pattern, heart rate and other factors. These may be determined from monitor data transferred to the processing unit and from data provided by a user via the user interface 486. In the processing unit, the system (implementing machine learning) may learn how to detect feeding time, detect feeding time and alert the user that it is feeding time, or activate a heating feature of the temperature controller 485 independently to prepare a bottle to feed the baby.

Soothing/Sleep Support

In some embodiments, once the system detects that the baby is about to awaken by detecting increased breathing rate 482*d*, changed vital signs 482*b* and 482*c*, or pre-learned signals, or crying via sound detection analysis, the system may mimic the sounds that the baby heard in the womb to soothe and calm the baby, and/or to return the baby to sleep, reducing the need for parents to wake up during the night. The soothing system may be personalized to increase the effectiveness of the soothing sound for the baby. The soothing sound may include, for example, tones, rhythms, audio effects, and the like. The speaker system may be attached to the monitor or may be a separate personalized soother. The speaker system may be locally in the vicinity to the monitor, or may be remote from the monitor, but close to the baby for daytime use. In addition to the speaker, a projector may add a visual dimension to the soothing system in which the personalized data collected may display the image most soothing to the baby. This may be manually or automatically provided. Both the speaker and projector may be charged when connected to the monitor or separately (e.g., the speaker and/or projector may include a battery).

In some embodiments, the vital signs may include an average heart rate, a maximum heart rate, a minimum heart rate, an inconsistency in the heart rate, an indication that the heart has stopped, an average breathing rate, a maximum breathing rate, a minimum breathing rate, an inconsistency in the breathing rate, an indication that breathing has stopped, a rate of change of the heart rate greater than a predetermined amount, a rate of change of the breathing rate greater than a predetermined amount, or any combination thereof. An inconsistent heart rate may be for example where the heart periodically misses a beat, or the heart beats at one rate for a time, then switches to a second rate. An inconsistent breathing rate may be for example where there are short periods of breathing apnea, or the baby breathes at one rate for a time, then switches to a second breathing rate.

In some embodiments, reaction signs may include data from the vital signs, movement of the eyes, movement of a body part, sounds emitted by the baby, a reaction to a scheduled occurrence, a reaction to a soothing method, a change in behavior over time, or any combination thereof. A sound emitted by the baby may include crying, mumbling, chattering, talking, breathing, screaming, or any combination thereof. A reaction to a soothing method may include lying down, closing eyes, blinking, ceasing to cry, moving into a predetermined sleeping posture, or any combination thereof. The predetermined sleeping posture may be determined from machine learning algorithms trained from previous event data when the baby was asleep.

Education/Communication

In some embodiments, utilizing a projector 483, either 2D or 3D (for example, a hologram) and based on machine learning models trained to assess the baby's attention and interest determined from any of the baby's eye movements, body movements and body positions, the type of eye movement (voluntary or involuntary), vital signs (such as, but not limited to, heart rate, change in heart rate, breathing rate, change in breathing rate, and temperature), reactions (such as, but not limited to, a startle reaction, a reaction to discomfort or pain, looking towards someone or something, looking away from someone or something, a reaction of pleasure and any combination thereof), and developmental stages, the system may allow the baby to communicate with remote family and build educational skills such as for example for understanding shapes, animals, objects, and the like.

In some embodiments, a type of eye movement may be for example, saccades, smooth pursuit movements, vergence movements, and/or vestibulo-ocular movements.

In some embodiments, the projector 483, monitor 482 and speaker (acoustic audio detector/microphone 484*a*) may also be configured to function as a proactive training system. Based on vital signs, reactions, video (movement and eye movement detection), and audio information received, data may be collected and analyzed using machine learning models and algorithms to personalize different training programs and to provide feedback to the user (parent or caregiver) on the baby's ongoing development.

Contactless Heart Rate and Blood Oxygen Measurement

In some embodiments, the blood oxygen level and the heart rate may be determined by photoplethysmography (PPG), which uses light and optics to measure properties of the blood. As blood enters and leaves the capillaries of the skin, varying amounts of light may be absorbed by the hemoglobin. The processor may use the amount of change in reflected light from the baby's skin to determine the blood oxygen level, and the period of the change in hemoglobin level to measure the rate at which the heart is pumping. Reflectance-mode PPG may be measured over large distances. The basic optical detection device for this type of measurement may be a simple webcam or an imaging device such as a camera on a mobile device. The light source may be ambient light in a room.

In some embodiments, the heart rate may be determined from skin pixels of image data of the baby's face. In other embodiments, PPG measurements from other parts of the body may used. In yet other embodiments, a gradient-descent algorithm with machine learning may be used to find the heart rate.

In some embodiments, the heart rate determining algorithm may first distinguish the skin pixels from non-skin pixels, which may be for example, hair, eyes, clothing and ornaments, or background objects such as for example, bedding, floors, walls, doors, or furniture. The output from the tracker may be analyzed and a background signal may be estimated.

In some embodiments, in the next stage of processing, the signal may be passed through a zero-phase Butterworth bandpass filter with a pass band of 40 to 180 beats per minute. A Fourier transform may be applied to the filtered signal to determine the heart rate. Typically, this process may be repeated about once a second. The frequency of determination may be in a range of once every 0.1 s to once every 20 s. In other embodiments, a state machine may pause the operation of the algorithm when movement occurs that may not be adequately compensated for by the tracker or by background signal removal, and then the state machine may re-start operation when the undesired movement has ceased.

In some embodiments, when the system 480 may detect dangerous conditions such as a breathing anomaly, for example, the system may determine a severity of the condition and may alert the user 45 accordingly via GUI 55, for example, upon the system assessing to transmit an alert triggered by a severity level decision. Image processing techniques may enable accurate and timely detection of heart rate and breathing from images. These detections may enable powerful monitoring and alerting in the infant sleep context. False negatives may be kept as low as possible, while avoiding false positives (false alarms).

In some embodiments, the system may detect posture of the baby.

In some embodiments, the system may alert a user if breathing or heartbeat rates are outside a predetermined range.

In some embodiments, the camera may include additional features, such as night vision, storage for videos and photos, as well as digital zoom. The night vision feature may allow the user such as a caregiver to obtain a clear view of the baby even in the dark that may be seen in region 57 in the GUI 55 of the mobile device 50. Digital zoom may allow a close-view of the baby and the vicinity of the baby in the region 57 in the GUI 55.

In some embodiments, the system may further include a thermal camera, able to detect if the head of the baby is covered, and to send an alarm to the user's mobile device 50 (e.g., a caregiver mobile device).

In some embodiments, the system may further include sensors, for monitoring the baby and the baby's environment. These sensors may include heat sensors, motion and sound sensors. Data obtained from these sensors may be communicated to the user's mobile device 50 (e.g., a caregiver mobile device).

Figure 8A:
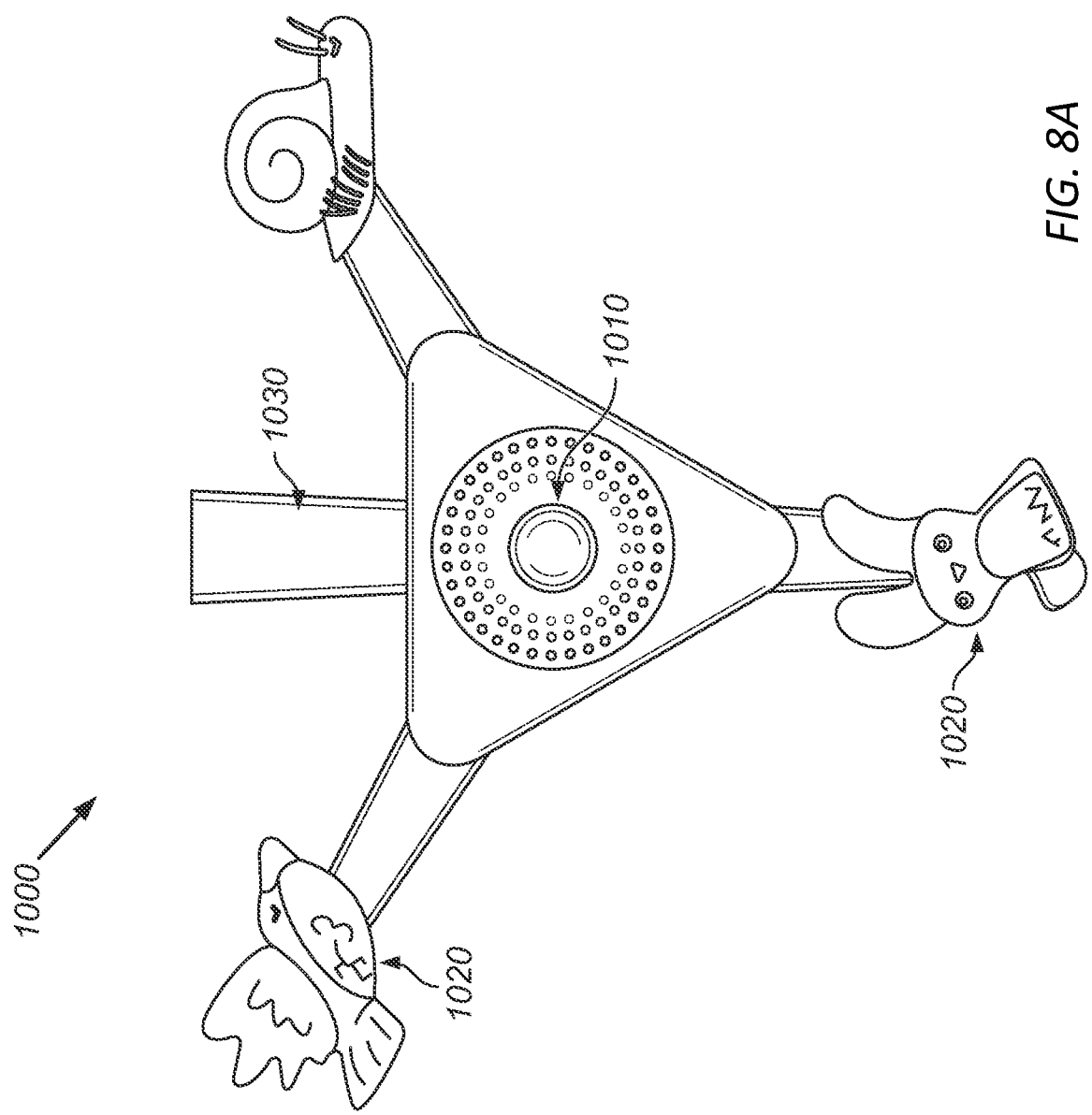
FIG. 8A illustrates a second embodiment of a baby monitor and interaction (BMID) device in accordance with one or more embodiments of the present disclosure.

FIG. 8A illustrates a second embodiment of a baby monitor and interaction (BMID) device 1000 in accordance with one or more embodiments of the present disclosure. The BMID 1000 may include a monitor 1010, smart objects 1020, and a mount 1030 for mounting the device. The monitor may include an optical subsystem, a two-way speaker or a two-way audio system (which may include a microphone and acoustic/audio detector, or any other two-way audio communication system), a projector, a microphone, an acoustic/audio detector, a breathing detector, a temperature detector, a heart rate detector, a user interface, a processing unit, an electromagnetic detector, or any combination thereof.

Figure 8B:
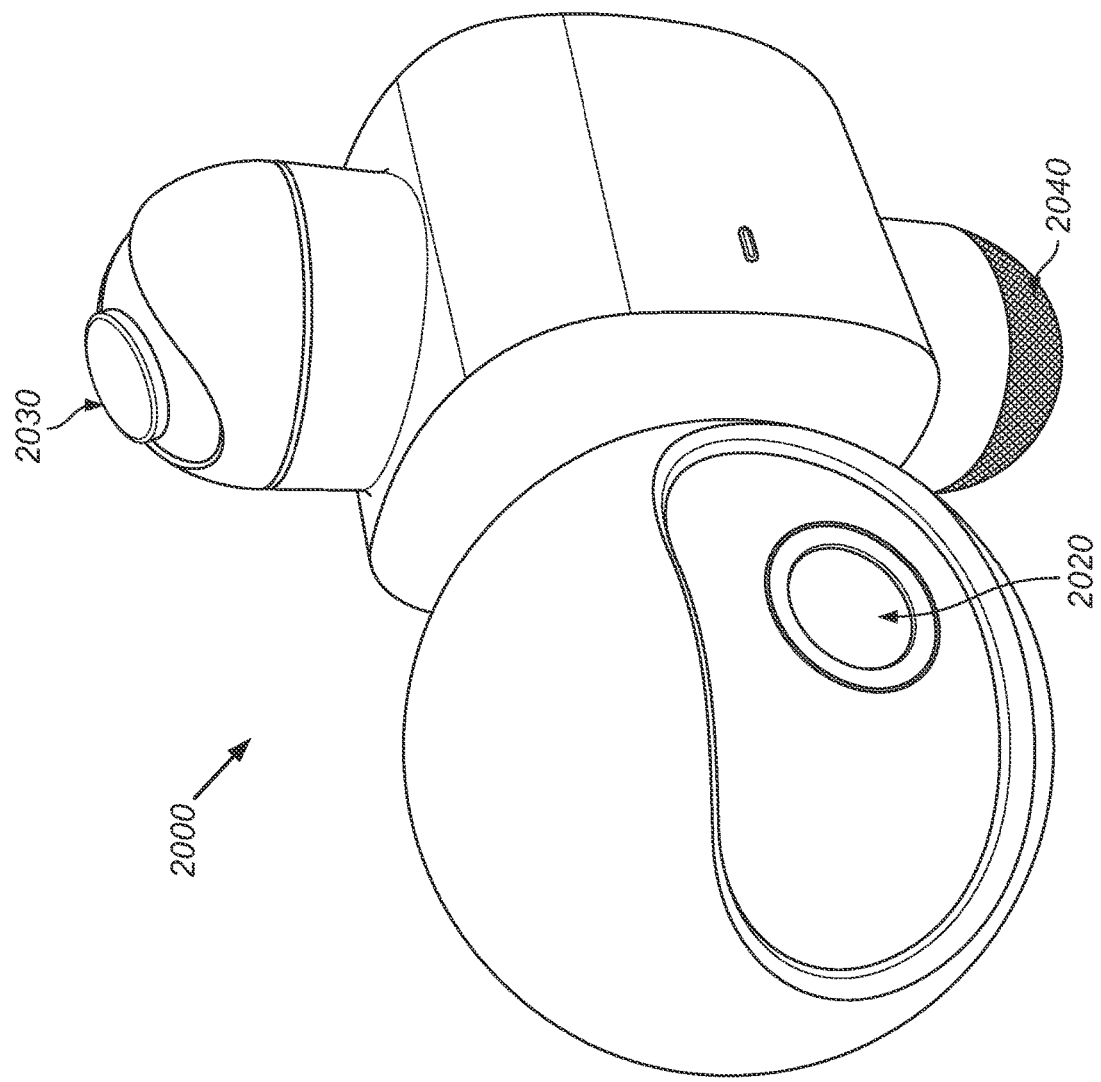
FIG. 8B illustrates a third embodiment of a baby monitor and interaction (BMID) device in accordance with one or more embodiments of the present disclosure.

FIG. 8B illustrates a third embodiment of a baby monitor and interaction device (BMID) 2000 in accordance with one or more embodiments of the present disclosure. The BMID 2000 may include a camera/projector 2020, at least one sensor 2030, and a microphone/loudspeaker 2040. A mount for the device is not shown.

Figure 9A:
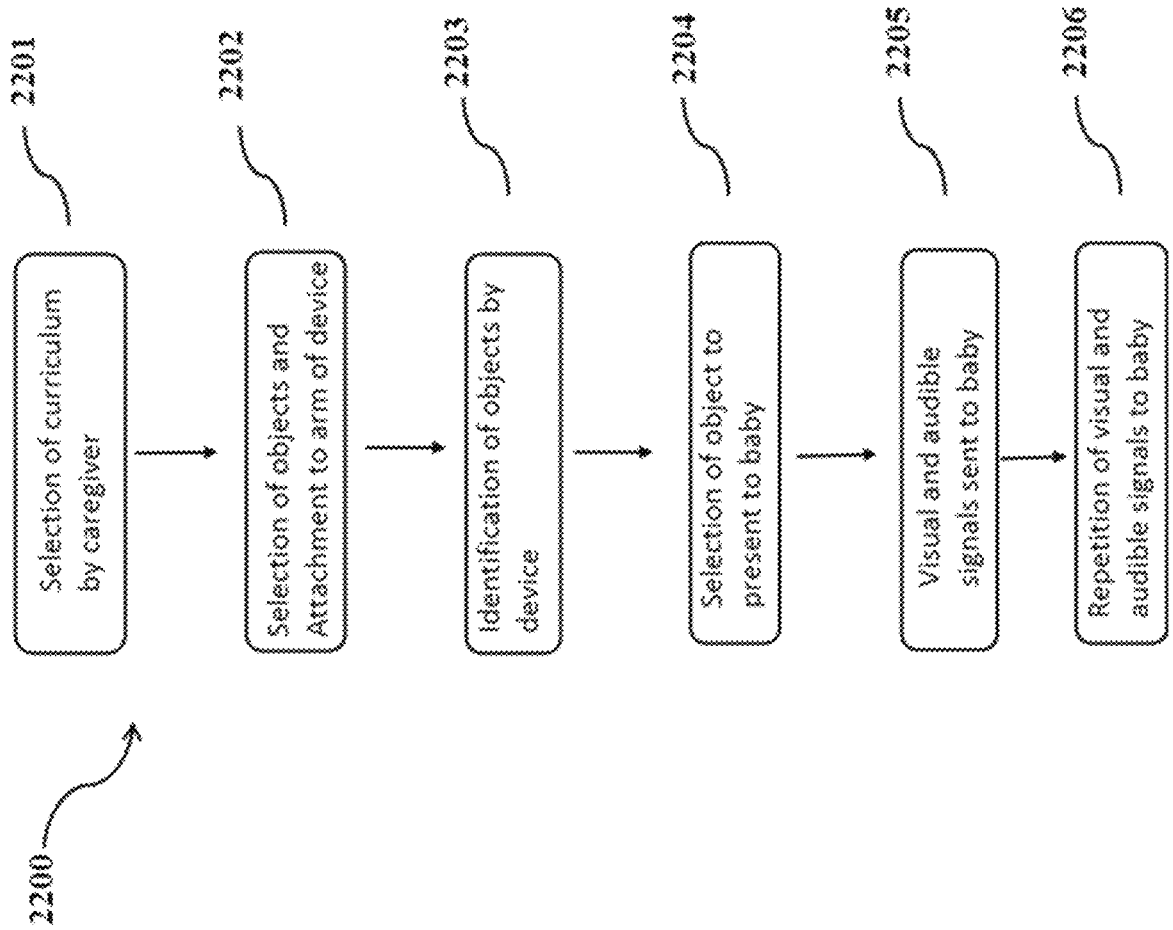
FIG. 9A is a flowchart of a method for educating a baby in accordance with one or more embodiments of the present disclosure.

FIG. 9A is a flowchart 2200 of a method for educating a baby in accordance with one or more embodiments of the present disclosure. The user may select a curriculum from suggested curriculums 2201. The curriculum may also be referred to herein as a baby-specific education plan. An appropriate curriculum may be selected from possible curriculums provided by the system via the GUI 55 of the mobile device 50 associated with the user. Choice of curriculum may be based on the age of baby, and cognitive abilities, as estimated by the user (e.g., caregiver). Based on the selected curriculum, the user may attach the related smart objects (e.g., the smart objects 1020) to the arms of the BMID device 2202. The curriculum may be selected based on the age of the baby. Thus, for example, black and white objects may be selected for a newborn, and colored objects may be selected for an older baby.

In some embodiments, an example of a baby-specific education plan or curriculum may include projecting a particular visual image to the baby in different categories such as different animals (dog, cat, the rabbit 25), different people (picture of mother, father, siblings, friends, etc), different objects (car, microwave oven, cake mixer, etc), natural events (wind, water and fire, for example) and to project the visual image with while an playing an sound associated with the projected visual object. The baby may then be subject to looking at two projected visual images, a first visual image and a second visual image while a sound associated with the first image is played from the speaker. The system 5 may assess that the baby understood the correlation between the sound and the first visual image by the image data assessing that the baby made eye movements and/or a head movement toward the first visual image. Similarly, the sound associated with the second image may be played.

In some embodiments, after the baby has been subjected to each visual image and associated sound, the system 5 may project a visual image of the car and determine if the baby made a sound of a car to determine if the baby understood.

In some embodiments, the AI-model (e.g., the baby-specific educational machine learning model) may output an indication or notification on GUI 55 that the baby understood the sound associated with the projected visual image by tracking the eye and/or head movements of the baby. The system 5 may issue a recommendation to the user 45 on the GUI 55 to continue with the current curriculum or modify the curriculum to a more advanced stage. If system assesses that the baby did not understand, the baby-specific educational machine learning model may output a recommendation to the user 45 on the GUI 55 continue with the current curriculum.

In some embodiments, the baby-specific educational machine learning model may automatically modify the baby-specific education plan or curriculum. For example, the modification may include the AI-model (e.g., the baby-specific educational machine learning model) outputting that the baby understood the image-sound pairs presented to the baby and may change the category of images (e.g., animals to household objects), and/or the modification may be inserting a video in place of static visual image, the modification may be saying the word associated with the projected image to see if the baby understand the word "cat" when the system 5 projects an image of a cat and a dog.

In some embodiments, the smart objects 1020 to be attached to the device may include different colored objects, shapes, animals and other suitably shaped objects. In other embodiments, the smart objects 1020 may include a processor used for processing data, storing data and communication. The attached smart objects may then be identified 2203 by the BMID device 1000 or by an application on the mobile device 50 of the user (e.g., a caretaker's mobile device). The user, via an application on a mobile device, may select 2204 one of the attached objects to introduce to the baby. Based on the selection, the device may send 2205 both visual and audible signals, clearly identifying the object to the baby. The visual signals may include movement of the object and/or lighting up the object. The audio signals may include both sounds associated with the object, (e.g. animal sounds for an animal), and voice signals, identifying the object to the baby. The system may repeat 2206 the visual and/or audible signals to the baby at least once. Following the learning session, the baby is tested in order to evaluate baby learning.

Figure 9B:
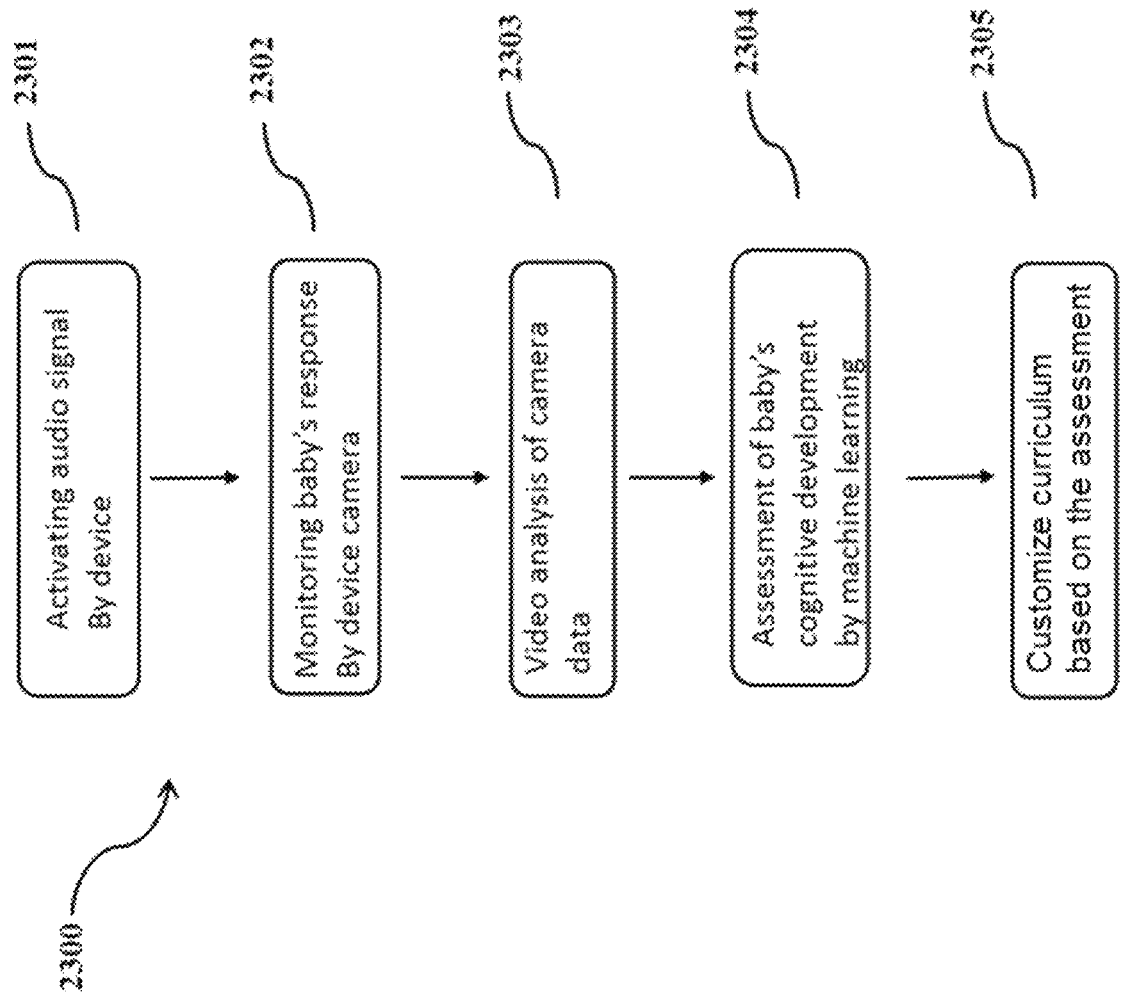
FIG. 9B is a flowchart of a method for testing a baby to evaluate baby learning in accordance with one or more embodiments of the present disclosure.

FIG. 9B is a flowchart 2300 of a method for testing a baby to evaluate baby learning in accordance with one or more embodiments of the present disclosure. The first step may include activation of the sound signal by the device 2301. No visual signals may be provided. Baby movements in response to the audio signal may be captured by the camera of the device 2302. The data obtained may then be analyzed by video analysis using monitoring software 2303. The monitoring software may use machine learning in order to assess the baby's mental and cognitive development 2304. Comparison data for the analysis may be obtained from a remote platform. Based on the analysis, a customized curriculum 2305 based on the assessment may be tailored to fit the baby's capabilities that may be sent to the user's mobile device 50.

In some embodiments, the system may include a projector, for projecting images onto a surface further away from the baby. The projector may include a 2-way video system with a microphone and a speaker for enabling audio communication with the baby. Utilizing the camera, and video analysis software described hereinabove, the ability of the baby to identify the images may be assessed, in order to provide a curriculum tailored to fit the baby's developmental abilities (e.g., to modify the baby-specific educational plan based on the machine learning assessment of the baby's cognitive development).

In some embodiments, the system may include breathing monitoring functionality. The breathing monitor may include computer vision technology, a motion sensor, a sound sensor, or any combination thereof for detecting movement or sound made by the baby. If no motion by the baby is detected during a predetermined time period, an alert will be sent to a user. The breathing monitor may include a radar or sonar component for detecting movement of the baby. The radar or sonar system may record heart and breathing rates and may send an alert to a user if breathing or heartbeat rates are outside a predetermined range. The radar system may be Continuous Wave (CW) radar, roi radar, Monopulse radar, or passive radar. The radar or sonar detection system may be provided in order to provide a second alarm upon detection of cessation of movement or a reduction in breathing rate. The purpose of the second alarm is to avoid false alarms, since computerized visual systems and baby breathing monitors generally may be prone to false alarms.

Heart Rate

Figure 10A:
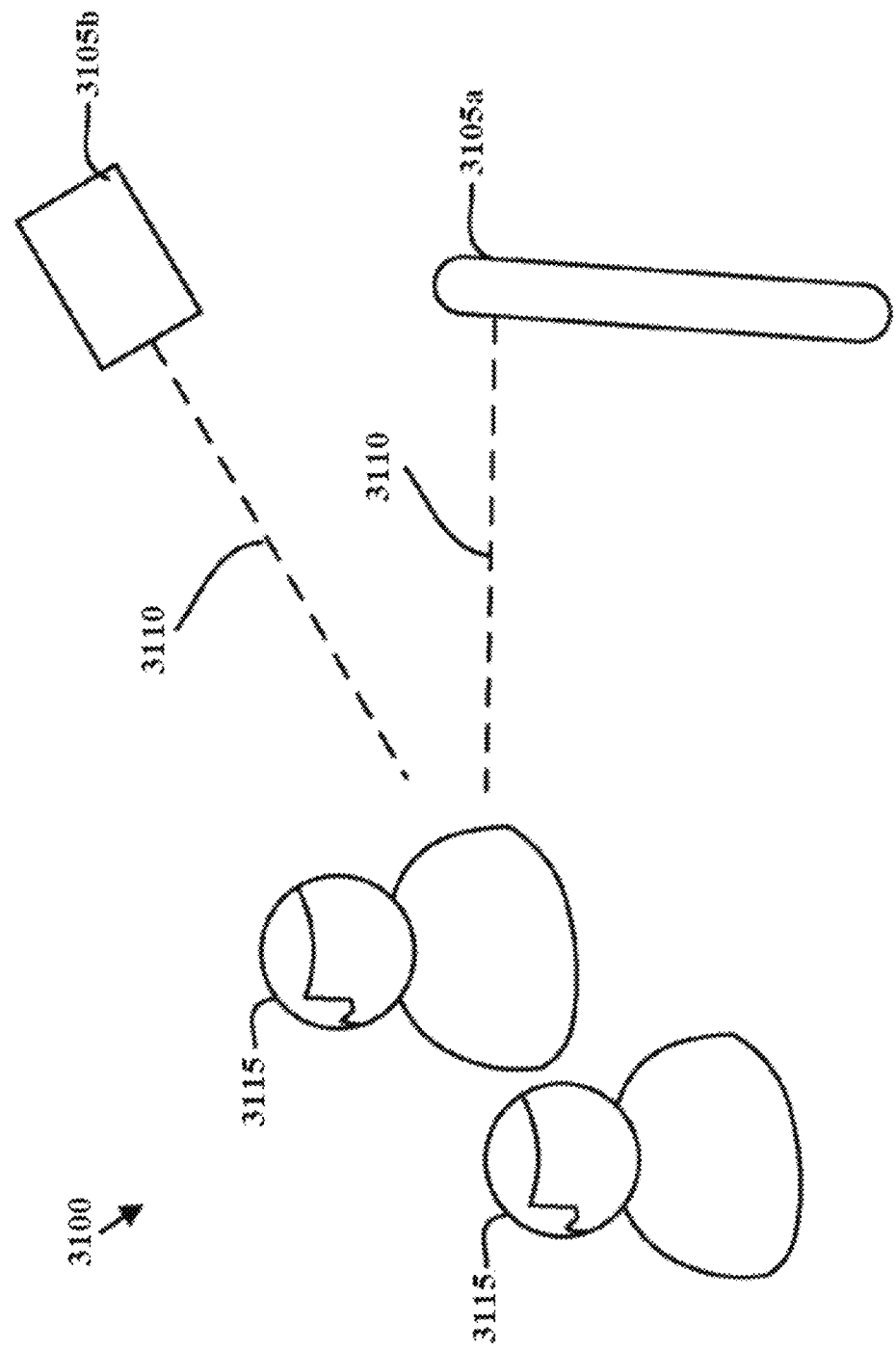
FIG. 10A is a drawing illustrating a heart rate estimation system in accordance with one or more embodiments of the present disclosure.

FIG. 10A is a drawing illustrating a heart rate estimation system 3100 in accordance with one or more embodiments of the present disclosure. The heart rate estimation system 3100 shown herein may be used, for example, to determine the heart rate of the baby-specific features 225 as used in algorithmic flow diagram 200 of the computer-based system for monitoring and interacting with a baby or to determine the heart rate needed by any other baby monitoring and interacting processes as disclosed herein. The system 3100 may include one or more electronic devices 3105A,B and one or more subjects 3115. The electronic devices 3105A,B may be a mobile telephone, a tablet computer, a laptop computer, a computer workstation, a video camera, or the like. The electronic devices 3105A,B may capture 3110 a video clip of video data of the subject(s) 3115 using a camera.

In some embodiments, the video data may be captured by one or more of a plurality of cameras, for example, a 3-color channel camera, a multispectral n-channel camera, an infrared camera, a depth camera, a 1-pixel sensor, a servo-controlled camera, or any combination thereof. The 3-color channel camera may be a red/green/blue (RGB) 3-color channel camera. For simplicity, the electronic devices 3105A,B and cameras may be referred to hereinafter in the singular or as an imaging device or imaging camera, although any number of electronic devices 3105 and cameras may be employed.

In the past, it has been impractical to calculate a heart rate from a video data of the subject 3115 because of motion of the electronic device 3105, the motion of the subject 3115, and/or changes in illumination. The embodiments described herein may generate a super pixel model from the video data and may calculate a heartbeat signal and heart characteristics as will be described hereinafter. As a result, the electronic device 3105A,B may accurately estimate the heart rate of the subjects 3115.

In some embodiments, the subjects 3115 may be people or animals. A heart rate may be estimated for the one or more subjects 3115 from the video data. The video data may be captured 3110 from a face or other body part of the subjects 3115. The video data may be captured 3110 from one or more of reflected natural light, reflected electrical lighting in the environment, reflected illumination provided by the system by, for example, lasers or infrared light emitting diodes (LEDs), and/or long-wave thermal infrared emission.

In some embodiments, the video data may be of a motion stabilized region of interest (ROI). The ROI may be any exposed portion of skin, such as for example, at least a portion of the forehead of a subject 3115, at least a portion of a neck of a subject 3115, at least a portion of an arm of a subject 3115, at least a portion of a back of a subject 3115, at least a portion of a chest of a subject 3115, at least a portion of an abdomen of a subject 3115, at least a portion of a posterior of a subject 3115, at least a portion of a leg of a subject 3115, at least a portion of a hand of a subject 3115, at least a portion of a foot of a subject 3115, or any combination thereof. In other embodiments, the pixels may include the ROI to form a continuous portion of the subject 3115.

Figure 10B:
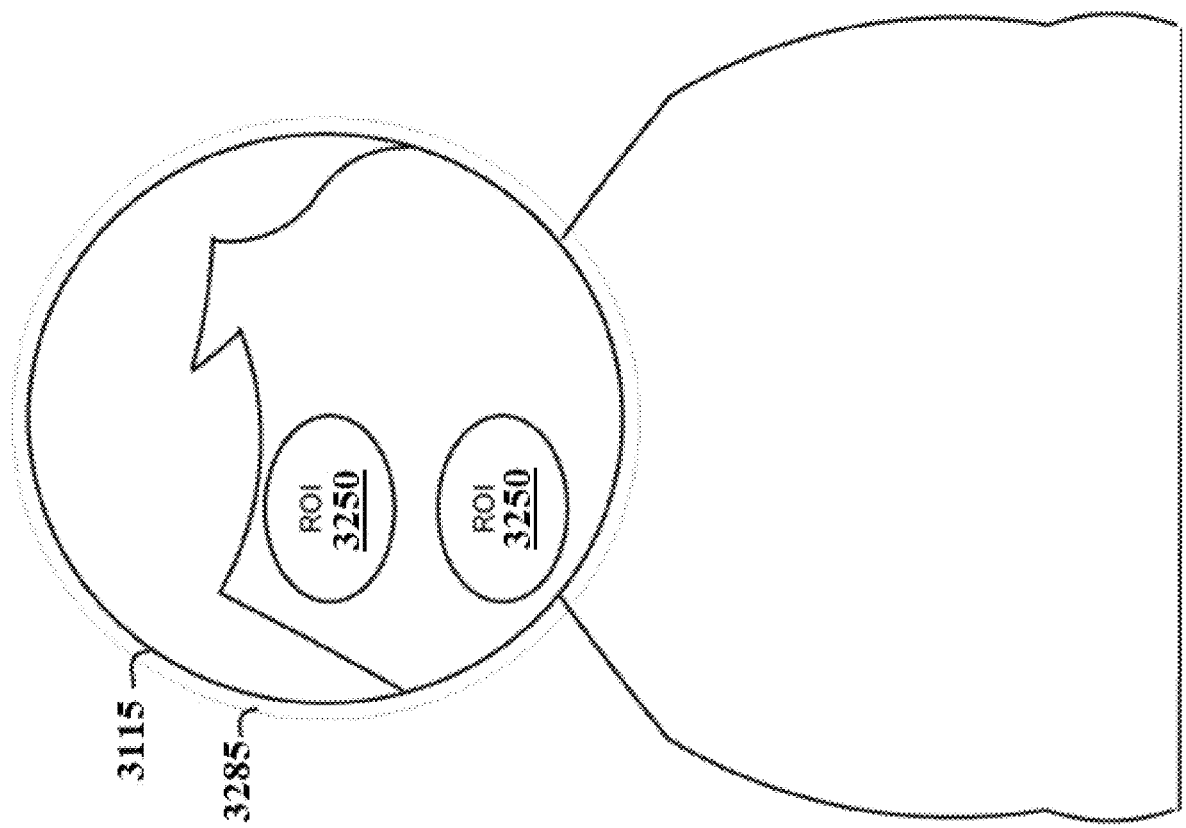
FIG. 10B is a drawing illustrating an object of interest (OOI) and a region of interest (ROI) on a subject in accordance with one or more embodiments of the present disclosure.

FIG. 10B is a drawing illustrating an object of interest (OOI) 3285 and a region of interest (ROI) 3250 on a subject 3115 in accordance with one or more embodiments of the present disclosure. In some embodiments, the electronic device 3105 may receive video data and detect the OOI 3285 from the video data. The electronic device 3105 may detect a face, a portion of the face such as a forehead, a neck, an arm, and/or other body part as the OOI 3285.

In some embodiments, the electronic device 3105 may further detect and/or track the OOI 3285. In other embodiments, the OOI 3285 may be detected using cascaded object detection on RGB pixels of the video data. The OOI 3285 may further be tracked with sub-pixel resolution using spatial correlation-based methods. Alternatively, the OOI 3285 may be detected and tracked using infrared band information. For example, a forehead OOI 3285 of the subject 3115 may be identified from an infrared hotspot. The OOI 3285 may also be detected and tracked using multi-spectral information.

In some embodiments, the OOI 3285 may be tracked from RGB pixels of the video data using facial landmarks. For example, typically via AI, although other optical analysis methods may be used, the electronic device 3105 may identify, typically via AI, the eyes and mouth of a subject

3115 from the RGB pixels and may detect the OOI 3285 relative to the eyes and mouth. Alternatively, the OOI 3285 may be tracked from RGB pixels of the video data using spatial correlation filters.

In some embodiments, the OOI 3285 may be detected and tracked using information from a depth camera. For example, the depth camera electronic device 3105 may identify contours of the subject 3115, and a facial OOI 3285 may be detected from the contours.

In some embodiments, the ROI 3250 may be identified within the OOI 3285. The ROI 3250 may be a specified region within the OOI 3285. For example, the ROI 3250 may be a forehead or cheek of a head OOI 3285. In some embodiments, the OOI 3285 and/or ROI 3250 may be identified from image segmentation. For example, the electronic device 3105 may segment the video data into multiple image segments and may identify the OOI 3285 and/or ROI 3250 from the image segments.

In some embodiments, the OOI 3285 and/or ROI 3250 may be detected using a bounding box. The bounding box may include a luma component, blue-difference chroma, red-difference chroma (YCbCr) color space. For example, the OOI 3285 and/or ROI 3250 may be identified as a region bounded by the YCbCr bounding box. In some embodiments, the electronic device 3115 may detect and track one or more OOI 3285 and may detect and track one or more ROI 3250 within each OOI 3285.

Figure 10C:
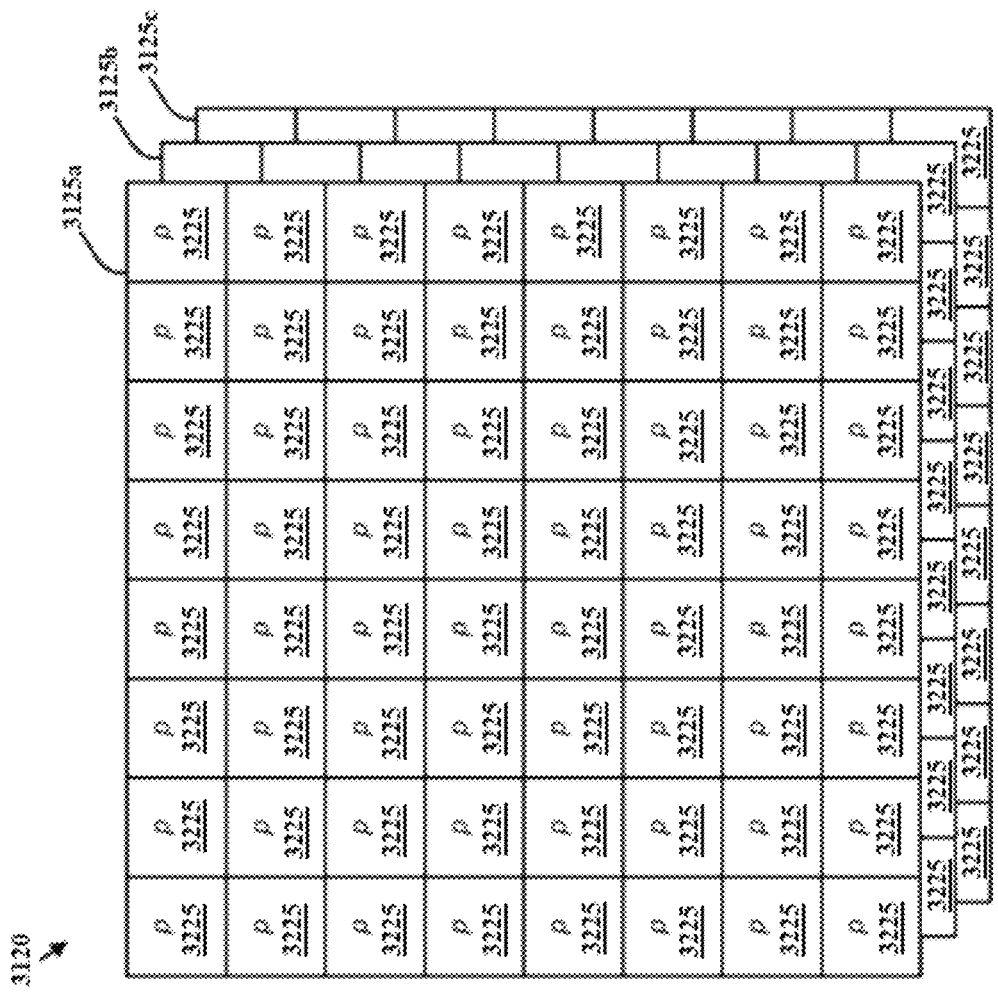
FIG. 10C is a schematic block diagram illustrating video data in accordance with one or more embodiments of the present disclosure.

FIG. 10C is a schematic block diagram illustrating video data 3120 in accordance with one or more embodiments of the present disclosure. The video data 3120 may include pixels 3225 for a plurality of time series 3125. The pixels 3225 of a time series 3125 may form an image. The video data 3120 may organize a data structure in a memory. The time series 3125 may be sequential. The time series 3125 may be randomly sampled from the video data. The data structure may be a random sample of the image, or any combination thereof. The pixels 3225 may be RGB, YCbCr, any other means of determining color, thermal pixels, UV pixels, or any combination thereof.

Figure 10D:
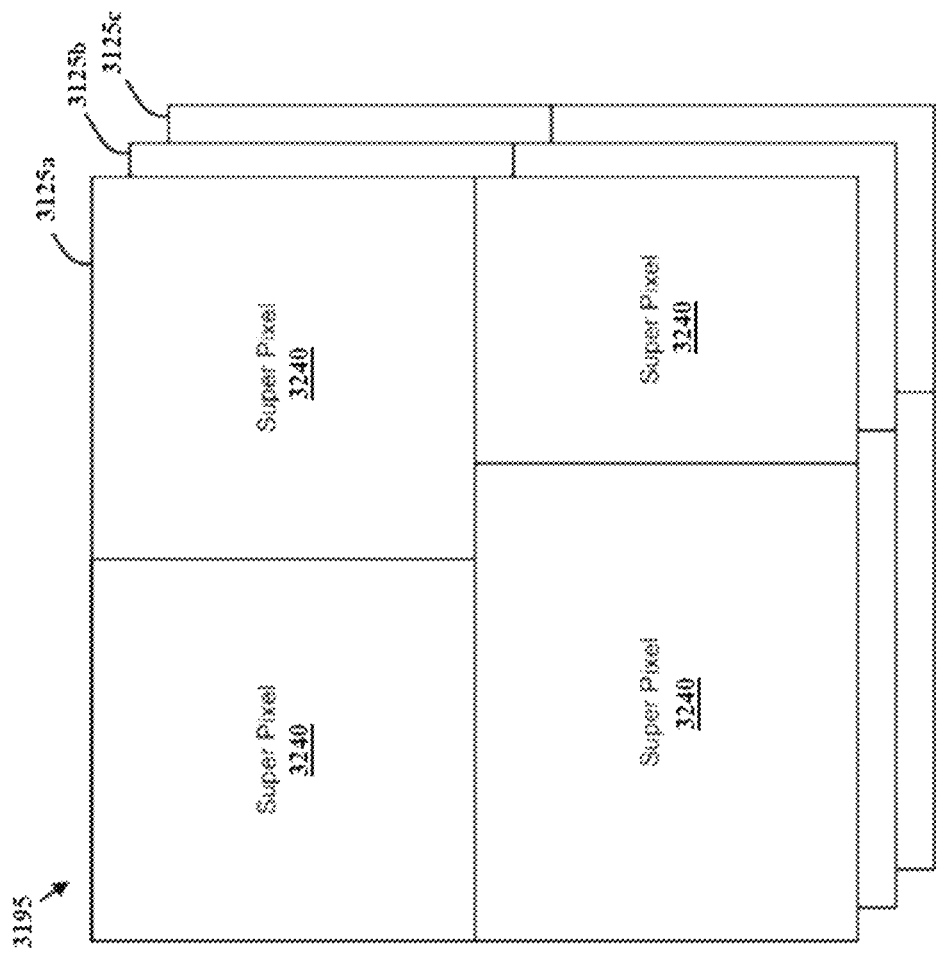
FIG. 10D is a schematic block diagram illustrating a super-pixel time series in accordance with one or more embodiments of the present disclosure.

FIG. 10D is a schematic block diagram illustrating a super-pixel time series 3195 in accordance with one or more embodiments of the present disclosure. The super-pixel time series 3195 may be organized as a data structure in a memory. In the depicted embodiment, groups of pixels 3225 as illustrated in FIG. 10C may be organized into super pixels 3240. The generation of the super pixels 3240 is described hereafter in FIG. 14. A plurality of time-series 3125 may be generated from each super pixel 3240 of the video data 3120.

Figure 11A:
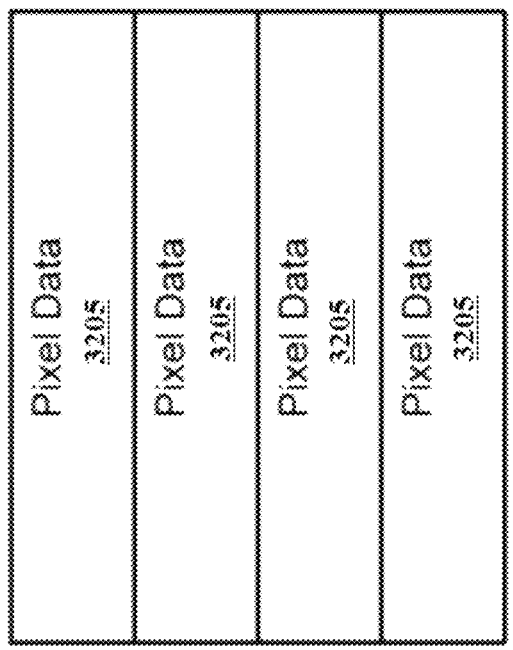
FIG. 11A is a schematic block diagram illustrating video data in accordance with one or more embodiments of the present disclosure.

FIG. 11A is a schematic block diagram illustrating video data 3120 in accordance with one or more embodiments of the present disclosure. The video data 3120 may be organized as a data structure in a memory. In the depicted embodiment, the video data 3120 may include a plurality of pixel data 3205. The pixel data 3205 may be organized in an array and may store brightness data, contrast data, color data, and the like. In addition, each instance of pixel data 3205 may include a pixel identifier. The pixel identifier may be a memory address, matrix indices, and the like.

Figure 11B:
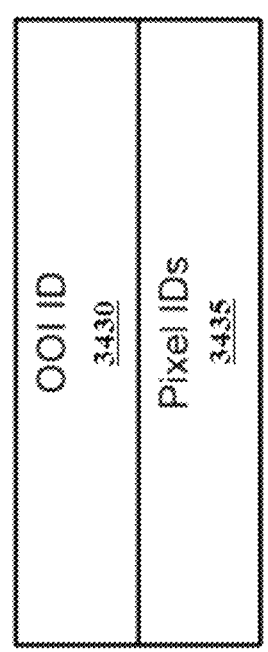
FIG. 11B is a schematic block diagram illustrating data in accordance with one or more embodiments of the present disclosure.

FIG. 11B is a schematic block diagram illustrating data 3440 in accordance with one or more embodiments of the present disclosure. The OOI data 3440 may be organized as a data structure in a memory. The OOI data 3440 may describe an OOI 285. In the depicted embodiment, the OOI data 3440 may include an OOI identifier 3430 and/or a plurality of pixel identifiers 3435. The OOI identifier 3430 may uniquely identify an OOI 3285. The pixel identifiers 3435 may reference the pixel data 3205 for the pixels 3225 that may include the OOI 3285.

FIG. 11C is a schematic block diagram illustrating ROI data 3425 in accordance with one or more embodiments of the present disclosure. The ROI data 3425 may be organized as a data structure in a memory. The ROI data 3425 may describe an ROI 3250. In the depicted embodiment, the ROI data 3425 may include an ROI identifier 3445 and a plurality of pixel identifiers 3435. The ROI identifier 3445 may uniquely identify an ROI 3250. The pixel identifiers 3435 may reference the pixel data 3205 for the pixels 3225 that may include the ROI 3250.

FIG. 11D is a schematic block diagram illustrating super pixel data 3255 in accordance with one or more embodiments of the present disclosure. The super pixel data 3255 may describe a super pixel 3240. In the depicted embodiment, the super pixel data 3255 may include a super pixel identifier 3215, a time series identifier 3220, measured pixel values 3265, and a plurality of pixel identifiers 3435.

In some embodiments, the super pixel data 3255 may be organized as a data structure in a memory, and may include pixels from any sensor data, as described herein.

In some embodiments, the super pixel identifier 3215 may uniquely identify the super pixel 3240. The time series identifier 3220 may identify a time series 3125 for the super pixel 3240. In some embodiments, the time series identifier 3220 indicates a position in a sequence. Alternatively, the time series identifier 3220 may indicate an absolute and/or relative time. The pixel identifiers 3435 may reference the pixel data 3205 for the pixels 3225 that may include the super pixel 3240.

In some embodiments, the measured pixel values 3265 may include one or more values representing an average value of pixels in the ROI 3250. The values may be one or more color values such as RGB values. In addition, the values may include brightness values, contrast values, and the like.

Figure 11E:
FIG. 11E is a schematic block diagram illustrating a super-pixel model in accordance with one or more embodiments of the present disclosure.

FIG. 11E is a schematic block diagram illustrating a super-pixel model 3270 in accordance with one or more embodiments of the present disclosure. The super-pixel model 3270 may be organized as a data structure in a memory. In the depicted embodiment, the model 3270 may include a super pixel identifier 3215, a time series identifier 3220, measured pixel values 3265, a background signal 3460, a heartbeat signal 3465, a breathing rate signal 3467, and a sensor noise signal 3470. Sensor signals that may be included are signals that are the result of machine learning such as, but not limited to, a class probability map, a feature map, or any combination thereof. Other sensor signals, as described herein, may also be included in the super-pixel model. The super pixel model may further include signals that are a result of machine learning such as, but not limited to, a class probability map, a feature map, a heat map, or any combination thereof.

In some embodiments, the super pixel identifier 3215 may identify one or more super pixels 3240 that are represented by the model 3270. The time series identifier 3220 may identify one or more time series t 3125 represented by the model 3270. For example, the time series identifier 3220 may identify 48 time series 3125 captured during a two second video clip. The measured pixel values $y_i(t)$ 3265 may include pixel values for each pixel 3225 i in each time series t 3125. The background signal $u_i(t)$ 3460 may estimate a contribution to the measured pixel values 3265 due to movement and lighting variations captured by the electronic device 3105 for each pixel 3225 i in each time series t 3125.

In some embodiments, the heartbeat signal $h_i(t)$ 3465 may estimate a contribution to the measured pixel values 3265 due to a heartbeat for each pixel 3225 i in each time series t 3125. The sensor noise signal $n_i(t)$ 3470 may estimate contributions to the measured pixel value 3265 due to sensor noise in the electronic device 3105 for each pixel i 3225 in each time series t 3125. Thus, the super-pixel model 3270 for a time series t 3125 may be modeled using Equation 1.

$$1.\ y_i(t) = u_i(t) + h_i(t) + n_i(t) \qquad \text{Eq. 1}$$

In some embodiments, the sensor noise signal 3470 may be assumed to be independent, identically distributed Gaussian noise. In addition, the background signal 3460 may be assumed to be smooth. For example, the change in the background signal 3460 between time series 3125 may be assumed to be less than a background threshold. In some embodiments, the background signal 3460 may be modeled as a first-order Markov random process. The background signal 3460 may be modeled using an auto aggressive model of the first order Markov random process. In some embodiments, the heartbeat signal 3465 may be assumed to be the same in each super pixel 3240. For example, $h_i(t) = h(t)$ may be assumed to be true for all i.

Figure 12:
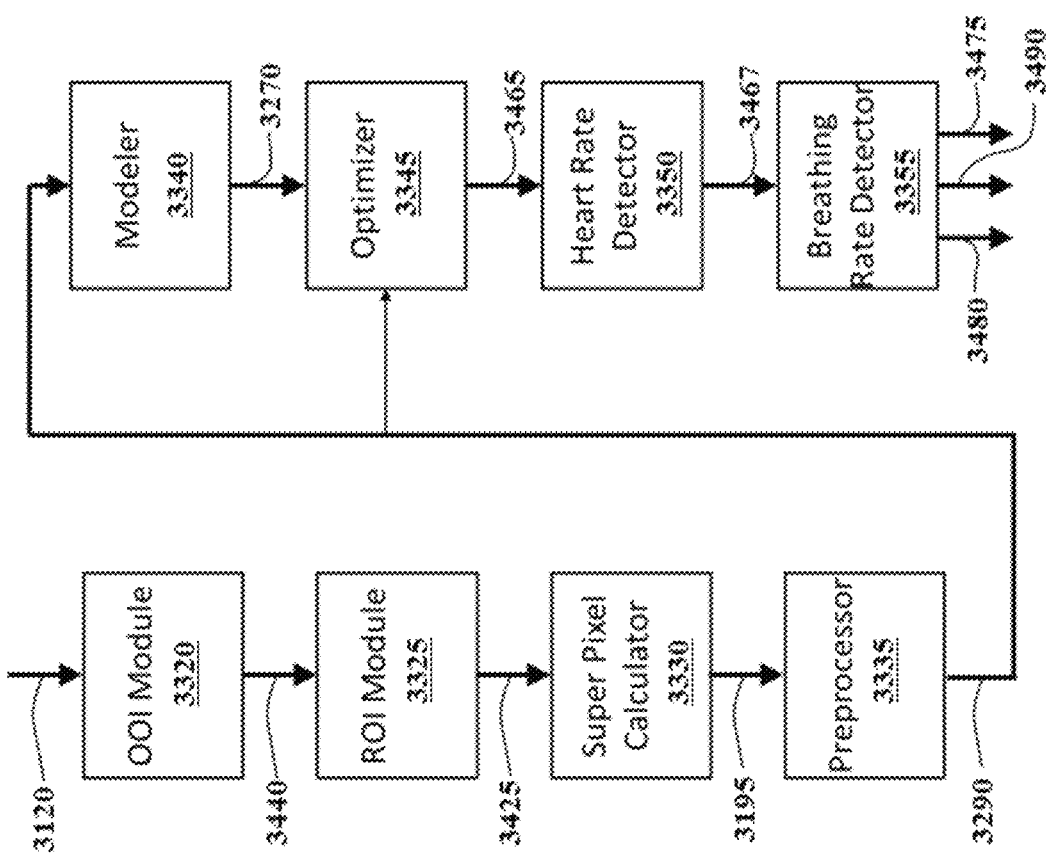
FIG. 12 is a flow diagram illustrating a heart rate estimation process in accordance with one or more embodiments of the present disclosure.

FIG. 12 is a flow diagram illustrating a heart rate estimation process 3101 in accordance with one or more embodiments of the present disclosure. The process 3101 may be performed by the electronic device 3105. The process 3101 is described in more detail in FIG. 14. In the depicted embodiment, an OOI module 3320, an ROI module 3325, a super pixel calculator 3330, a pre-processor 3335, a modeler 3340, an optimizer 3345, and/or a heart rate detector 3350 may perform the process 3101. The OOI module 3320, ROI module 3325, super pixel calculator 3330, pre-processor 3335, modeler 3340, optimizer 3345, heart rate detector 3350, breathing rate detector 3355 and/or any other detector may be implemented in semiconductor hardware and/or code executed by a processor.

In some embodiments, the OOI module 3320 may receive the video data 3120 from a camera of the electronic device 3105 and detect an OOI 3285. The OOI module 3320 may track the OOI 3285 using the camera and generate OOI data 3440 that describes the OOI 3285. The ROI module 3325 may receive the OOI data 3440 and identify an ROI 3250 within the OOI 3285. The ROI module 3325 may generate ROI data 3425 that describes the ROI 3250.

In some embodiments, the super pixel calculator 3330 may receive the ROI data 3425 and generate super pixels 3240 in a super-pixel time series 3195. The preprocessor 3335 may preprocess the super-pixel time series 3195 to remove interfering signals from the super-pixel time series 3195 and generate a preprocessed super-pixel time series 3290.

In some embodiments, the modeler 3340 may generate the super pixel model 3270 from the super-pixel time series 3195 and/or the preprocessed super-pixel time series 3290. The optimizer 3345 may calculate a heartbeat signal 3255 from the super-pixel model 3270. In some embodiments, the optimizer 3345 may calculate a heartbeat signal 3465 from the super-pixel model 3270 and the preprocessed super-pixel time series 3290. The heart rate detector 3350 may calculate heart characteristics such as, but not limited to, a heart rate 3480, an inter-beat interval 3475, and/or a heart rate variability 3490 from the heartbeat signal 3465. The breathing rate detector 3355 may calculate breathing characteristics such as, but not limited to, a breathing rate 3367, a breathing rate variability and any combination thereof from the breathing signal.

Figure 13:
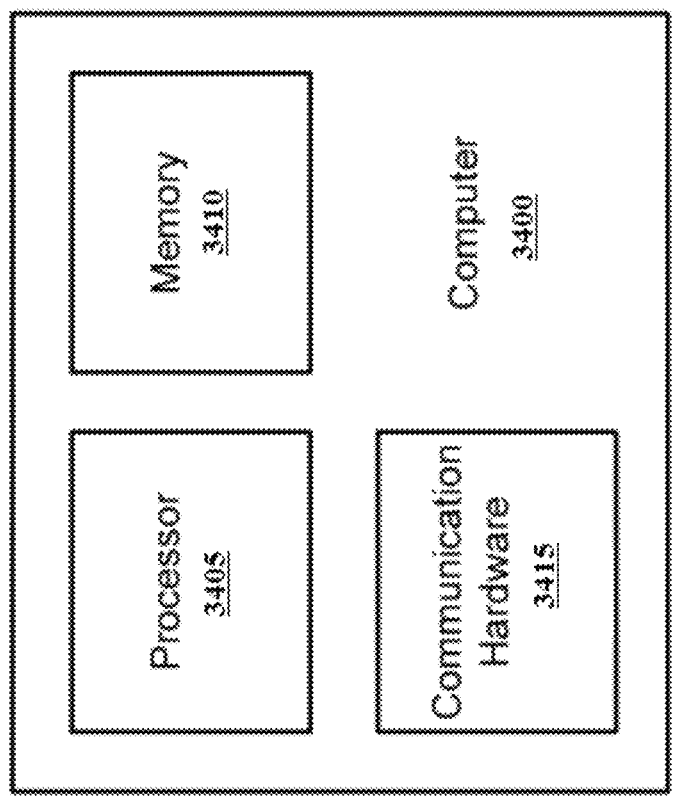
FIG. 13 is a schematic block diagram illustrating a computer in accordance with one or more embodiments of the present disclosure.

FIG. 13 is a schematic block diagram illustrating a computer 3400 in accordance with one or more embodiments of the present disclosure. The computer 3400 may be embodied in the electronic device 3105. The computer 3400 may include a processor 3405, a memory 3410, and communication hardware 3415. The memory 3410 may be a computer readable storage medium such as a semiconductor storage device, a hard disk drive, a holographic storage device, a micromechanical storage device, or combinations thereof. The memory 3410 may store code. The processor 3405 may execute the code. The communication hardware 3415 may communicate with other devices.

Figure 14:
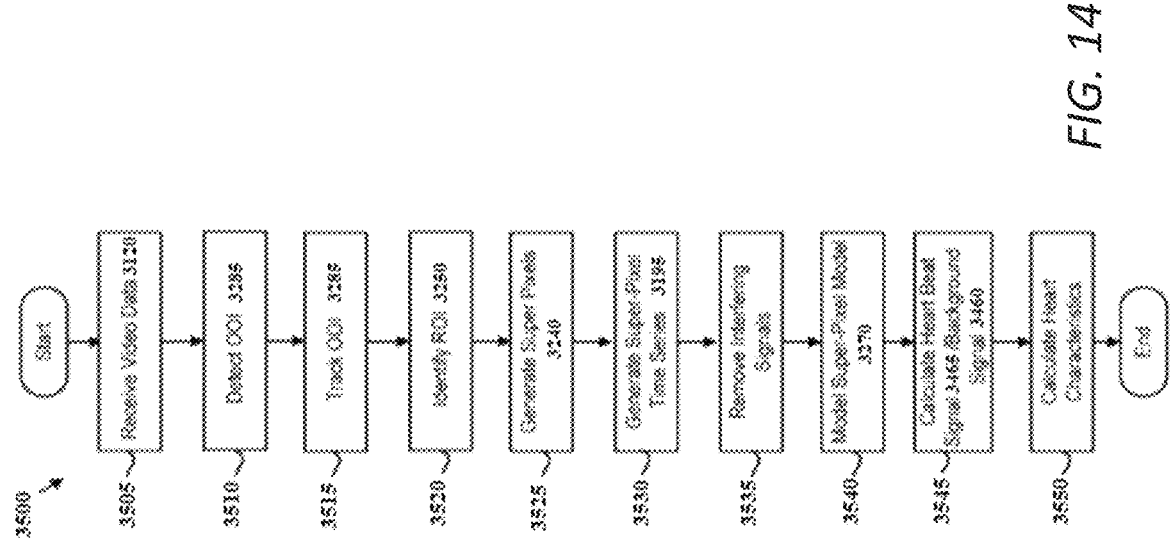
FIG. 14 is a flowchart of a heart characteristic estimation method in accordance with one or more embodiments of the present disclosure.

FIG. 14 is a flowchart of a heart characteristic estimation method 3500 in accordance with one or more embodiments of the present disclosure. The method 3500 may remotely estimate heart characteristics such as, but not limited to, heart rate, heart interbeat interval and heart rate variability. The method 3500 may be performed by the processor 3405 and/or the OOI module 3320, ROI module 3325, super pixel calculator 3330, pre-processor 3335, modeler 3340, optimizer 3345, and heart rate detector 3350 in the electronic device 3105.

In some embodiments, the method 3500 may start, in some embodiments, when the electronic device 3105 receives 3505 the video data 3120 from the camera of the electronic device. In some embodiments, the video data 3120 may be received as one or more time series 3125 of pixels 3225.

In some embodiments, the electronic device 3105 may further detect 3510 the OOI 3285 in each image of the video data 3120. The image may include pixels 3225 for a time series 3125. The OOI 3285 may be a subject and/or a body part of the subject 3115 such as a head, a neck, and arm, leg, and/or the like. In some embodiments, the OOI 3285 may be detected using cascaded object detection on RGB pixels of the video data 3120.

In some embodiments, the electronic device 3105 may further track 3515 the OOI 3285 in each image of the video data 3120. In some embodiments, the OOI 3285 may be tracked using infrared band information from an infrared camera and/or a multi-spectral camera. The electronic device 3105 may generate OOI data 3440 that represents the OOI 3285.

In some embodiments, the electronic device 3105 may identify 3520 one or more ROI 3250 within the OOI 3285. The ROI 3250 may be a region of a body part such as a forehead, a wrist, and the like. In some embodiments, the ROI 3250 is identified using image segmentation. The electronic device 3105 may generate ROI data 3425 that represents the ROI 3250.

In some embodiments, the electronic device 3105 may generate 3525 super pixels 3240 in each ROI 3250 from the video data 3120 and the ROI data 3425. In some embodiments, each super pixel 3240 may include a specified number of pixels 3225. Alternatively, each super pixel 3240 may be formed of adjacent pixels 3225 with measured pixel values 3265 within a value range.

In some embodiments, the electronic device 3105 may further generate 3530 a super-pixel time series 3195 for a plurality of super pixels 3240 in each image of the video data 3120. In some embodiments, one or more sequential super pixels 3240 may be concatenated to form the super-pixel time series 3195. Alternatively, one or more non-sequential super pixels 3240 may be selected and concatenated to form the super-pixel time series 3195.

In some embodiments, the electronic device 3105 may remove 3535 interfering signals from the super-pixel time series 3195. The removal of the interfering signals may be preprocessing. In some embodiments, the interfering signals may be removed 3535 using de-trending. The de-trending may be performed by modeling the background signal 3460 as a Gaussian process. Alternatively, the de-trending may be performed by decorrelating the super-pixel time series 3195 with auxiliary signals derived from the position of a facebox that bounds a face of a subject 3115 and from other regions in the video data 3120. In some embodiments, removing 3535 the interfering signals from the super-pixel time series 3195 may include band pass filtering to remove signals outside a frequency band of normal heart rate. For example, signals with a frequency below 40 beats per minute (bpm) and above 170 bpm may be filtered from the super-pixel time series 3195.

In some embodiments, the electronic device 3105 may model 3540 the super-pixel time series 3195 as the super-pixel model 3270. In some embodiments, the super-pixel time series 3195 is modeled in the form of Equation 1.

In some embodiments, the electronic device 3105 may calculate 3545 the heartbeat signal 3465 using the super-pixel model 3270. In some embodiments, the heartbeat signal 3465 and the background signal 3460 may be calculated 3545 by optimizing Equation 2 subject to Equations 3 and 4. In some embodiments, the sum on i may be over the plurality of super pixels 3240, and the sum on t may be over the plurality of super pixels 3240 in the time series 3125, $\lambda_1$ and $\lambda_2$ may be user parameters, H may be an (M+1)×(2L+1) Toeplitz matrix having $(i,j)^{th}$ element h(2L+i−j) for l=1, 2, ..., M+1 and j=1, 2, ..., 2L+1, h is an (M+1)×1 vector having $i^{th}$ element h(L+T+i−1) for i=1, 2, ..., M+1, and $\|\cdot\|_*$ may be a nuclear norm.

$$\min_{u_i(t),h(t)} \sum_i \sum_t |y_i(t) - u_i(t) - h(t)|^2 + \quad \text{Eq. 2}$$
$$\lambda_1 \|[H \mid h]\|_* + \lambda_2 \sum_i \sum_t |u_i(t+1) - u_i(t)|^2$$

$$[H]_{(i,j)} = h(2L + i - j) \quad \text{Eq. 3}$$

$$[h]_i = h(L + T + i - 1) \quad \text{Eq. 4}$$

In some embodiments, alternatively, the heartbeat signal 3465 and the background signal 3460 may be calculated 3545 by optimizing Equation 5, where D is given by Equation 6 and P is given by Equation 7, and α and β are user selectable constants that may generate the smoothness of the background signal 3460 and/or the predictability of the heartbeat signal 3465. The vector u may include samples of the background signal and the vector h may include samples of the heartbeat signal. The prediction coefficients $p_L, \ldots, p_{-L}$ may be interpolation coefficients derived from a hypothesized period of the heartbeat signal 3465 and the placement of the −1 in the P matrix may also be dependent on the hypothesized period of the heartbeat signal 3465. This optimization may be repeated for a series of different heartbeat periods and a first heartbeat period giving the smallest objective value that may be chosen as the period of the heartbeat signal 3465.

$$\min_{u,h} \left\| \begin{bmatrix} y \\ 0 \\ 0 \end{bmatrix} - \begin{bmatrix} I & I \\ \alpha D & 0 \\ 0 & \beta P \end{bmatrix} \begin{bmatrix} u \\ h \end{bmatrix} \right\| \quad \text{Eq. 5}$$

$$D = \begin{bmatrix} -1 & 1 & & \\ & -1 & 1 & \\ & & \ddots & \ddots \\ & & & -1 & 1 \end{bmatrix} \quad \text{Eq. 6}$$

$$P = \begin{bmatrix} p_L & \cdots & p_{-L} & 0 & 0 & -1 & 0 & 0 & 0 \\ & \ddots & & \ddots & & & \ddots & & \\ 0 & 0 & 0 & p_L & \cdots & p_{-L} & 0 & 0 & -1 \end{bmatrix} \quad \text{Eq. 7}$$

In some embodiments, the electronic device 3105 may calculate 3550 the heartbeat characteristics from the heartbeat signal 3465 and the method 3500 ends. The heartbeat characteristics may include the heart rate 3480, the inter-beat interval 3475, and/or the heart rate variability 3490. The electronic device 3105 may calculate 3550 the heart rate 3480 using one or more of a machine learning analysis of the heartbeat signal 3465, a peak of a Fourier transform of the heartbeat signal 3465, a power spectral density of the heartbeat signal 3465, a zero crossing rate of the heartbeat signal 3465, and/or a sliding correlation analysis of the heartbeat signal 3465.

The embodiments disclosed herein may detect the OOI 3285 from video data, may track the OOI 3285, and may identify the ROI 3250 within the OOI 3285. The embodiments disclosed herein may further generate super pixels 3240 from pixels 3225 within the ROI 3250. In addition, the embodiments herein may be used to generate a super-pixel time series 3195 and to model the super-pixel time series 3195 as a super-pixel model 3270. The super pixel model 3270 may be used to calculate the heartbeat signal 3265 and other heart characteristics. As a result, the embodiments may remotely estimate a heart rate 3480 of one or more subjects 3115. The embodiments may allow, for example, the heart rates 3480 of animals to be remotely estimated, the heart rates 3480 of human subjects 3115 to be estimated in situations where the subjects 3115 may be active, and for the rapid determination of the heart rate 3480. As a result, the embodiments described herein may provide a practical and effective way for remote estimation of heart rates 3480.

Breathing Rate

Figure 15A:
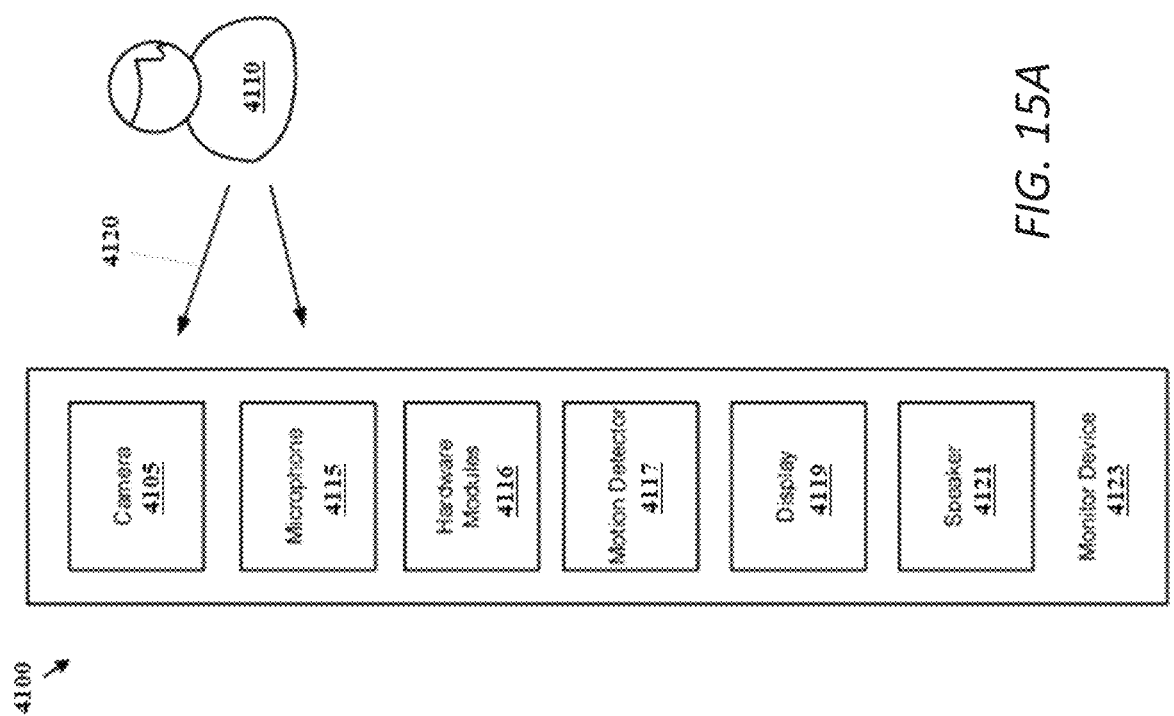
FIG. 15A is a schematic block diagram of a breathing event identification system in accordance with one or more embodiments of the present disclosure.

FIG. 15A is a schematic block diagram of a breathing event identification system 4100 in accordance with one or more embodiments of the present disclosure. The breathing event identification system 3100 shown herein may be used, for example, to determine the breathing detection for the baby-specific features 225 as used in algorithmic flow diagram 200 of the computer-based system for monitoring and interacting with a baby or to detect the baby's breathing rate as needed by any of the other baby monitoring and interaction processes as disclosed herein. The system 4100 may identify a breathing event and/or large-scale motion of a subject 4110 from a video stream of the subject 4110 captured by a camera 4105. In addition, the system 4100 may generate an alert if no breathing event is identified and no large-scale motion is identified. In some embodiments, the system 4100 may also include a monitor device 4123. The monitor device 4123 may include the camera 4105, microphone 4115, hardware modules 4116, and/or a motion detector 4117. In addition, the monitor device 4123 may include a display 4119 and/or a speaker 4121. In some embodiments, the hardware modules 4116 may include dedicated semiconductor circuits. The dedicated semiconductor circuits may include a memory. In addition, the hardware modules 4116 may include a computer.

In some embodiments, the camera 4105 may capture a video stream 4120 of the subject 4110. The camera 4105 may employ a bandpass filter in the range of 0.8-2.5 micrometers. In addition, the camera 4105 may employ a Charge Coupled Device (CCD) that is tuned to 1.5 micrometers. The camera 4105 may capture the video stream as infrared image frames.

In some embodiments, when a subject 4110 may be at risk for ceasing to breathe, the subject 4110 may be monitored to identify the breathing rate and/or detect the cessation of breathing so that timely aid may be given. Furthermore, noninvasive monitoring may be used to identify breathing events so the subject 4110 is not disturbed.

In some embodiments, breathing events may be detected optically and audibly. For example, baby monitors may be used to monitor a baby's breathing through a video (sequence of images) of the baby captured by a camera 4105 and/or a sound of the baby's breathing captured by the microphone 4115. Unfortunately, when identifying breathing events, the consequences of both false positives and false negatives may be high that monitoring may need to detect breathing events with extreme accuracy.

The embodiments described herein identify breathing events and/or large-scale motions based on a video stream as will be described hereinbelow. The embodiments further generate alerts, present displays, and present statistics based on the breathing events.

FIG. 15B is a schematic block diagram of a breathing report 4165 in accordance with one or more embodiments of the present disclosure. The breathing report 4165 may be organized as a data structure in a memory. In the depicted embodiment, the breathing report 4165 may include a breath rate 4231, a maximum inter-breath interval 4233, a minimum inter-breath interval 4235, inter-breath interval statistics 4237, an inter-breath interval histogram 4239, and/or apnea event data 4241.

In some embodiments, the breath rate 4231 may represent a frequency of breathing. The maximum inter-breath interval 4233 may specify a longest interval between breathing events. The minimum inter-breath interval 4235 may specify a shortest interval between breathing events. The inter-breath interval statistics 4237 may specify one or more of a mean, average, and mode of intervals between breathing events. The inter-breath interval histogram 4239 may describe the relative frequencies of breath intervals between breathing events. The breath intervals may be organized into one or more ranges.

In some embodiments, the apnea event data 4241 may be calculated from the breath rate 4231, maximum inter-breath interval 4233, minimum inter-breath interval 4235, inter-breath interval statistics 4237, and inter-breath interval histogram 4239. The apnea event data 4241 may be used to identify sleep apnea events.

FIG. 15C is a schematic block diagram of a motion report 4160 in accordance with one or more embodiments of the present disclosure. The motion report 4160 may be organized as a data structure in a memory. In the depicted embodiment, the motion report 4160 may include a motion frequency 4243, a motion magnitude 4245, a motion duration 4247, a sleep length 4249, a sleep quality 4251, and sleep intervals 4253.

In some embodiments, the motion frequency 4243 may describe the frequency of large-scale motions by the subject 4110. The motion magnitude 4245 may describe a number of pixels affected by each motion. The motion duration 4247 may describe the duration from start to end of each large-scale motion by the subject 4110.

In some embodiments, the sleep length 4249 may describe a length of a time interval during which the subject 4110 is asleep. The sleep quality 4251 may estimate the restfulness of the sleep for the subject 4110. The sleep intervals 4253 may describe each interval during which the subject 4110 is asleep.

FIG. 15D is a schematic block diagram of breathing data in accordance with one or more embodiments of the present disclosure. The breathing data may be organized as a data structure in a memory. In the depicted embodiment, the breathing data may include a field of view policy 4261, an event time interval 4263, a breathing event 4265, and a large-scale motion 4267.

In some embodiments, the field of view policy 4261 may specify when the subject 4110 may be satisfactorily viewed by the camera 4105. The event time interval 4263 may specify a time interval during which a breathing event 4265 and/or a large-scale motion 4267 of the subject 4110 may be identified in order to not generate an alert. The breathing event 4265 may be an identified breath by the subject 4110. The large-scale motion 4267 may indicate motion by the subject 4110. The motion may make determining a breathing event 4265 impossible.

FIG. 16A is a schematic diagram illustrating regions 4003 in an image frame 4005 in accordance with one or more embodiments of the present disclosure. In the depicted embodiment, an image frame 4005 is divided into a rectangular grid of one or more regions 4003. In some embodiments, all regions 4003 may have rectangular shapes and may be equal in size.

FIG. 16B is a schematic diagram illustrating regions 4003 in an image frame 4005 in accordance with one or more embodiments of the present disclosure. In the depicted embodiment, an image frame 4005 may be divided into circular shaped regions 4003. The regions 4003 do not overlap and some pixels of the image frame 4005 are not included in any region 4003.

FIG. 16C is a schematic diagram illustrating regions 4003 in an image frame 4005 in accordance with one or more embodiments of the present disclosure. In the depicted embodiment, the image frame 4005 may be divided into circular shaped regions 4003. The regions 4003 may overlap so that some pixels of the image frame 4005 are included in two or more regions 4003 while other pixels are not included in any region 4003.

Figure 16D:
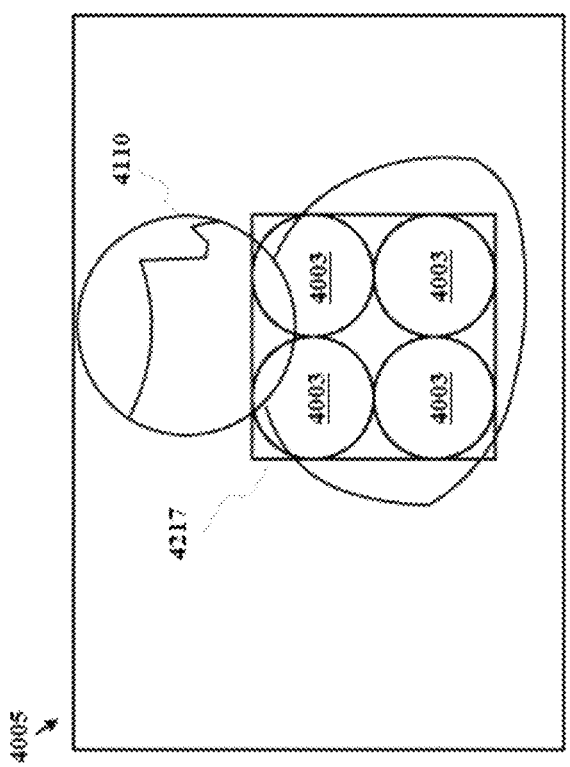
FIG. 16D is a schematic diagram illustrating user selected regions in an image frame in accordance with one or more embodiments of the present disclosure.

FIG. 16D is a schematic diagram illustrating user selected regions 4003 in an image frame 4005 in accordance with one or more embodiments of the present disclosure. Using an interface, a user may identify the pixels in the image frame 4005 that may be occupied by the subject 4110 with user input defining a user selected area 4217. When user input is provided, the regions 4003 may be obtained by dividing the user selected area 4217.

Figure 16E:
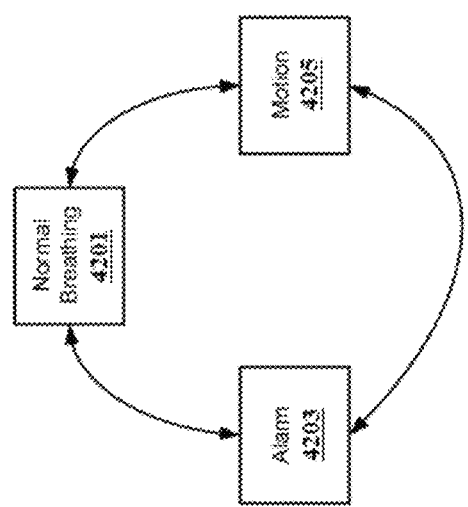
FIG. 16E is a schematic block diagram of breathing event identification states in accordance with one or more embodiments of the present disclosure.

FIG. 16E is a schematic block diagram of breathing event identification states in accordance with one or more embodiments of the present disclosure. The depicted embodiment may include a normal breathing state 4201, an alarm state 4203, and a motion state 4205 of a state machine. When normal breathing is detected by the monitor device 4123 while in the alarm state 4203 or in the motion state 4205, the state machine transitions to the normal breathing state 4201. Normal breathing may be indicated by a breath event 4265 within the event time interval 4263. When large-scale motion 4267 is detected by the monitor device 4123 in either the alarm state 4203 or the normal breathing state 4201, the state machine transitions to the motion state 4205. In some embodiments, the large-scale motion 4267 is detected within the event time interval 4263. If normal breathing and motion are not detected by the monitor device 4123 in either the normal breathing state 4201 or the motion state 4205, the state machine transitions to the alarm state 4203. In some embodiments, the normal breathing and/or large-scale motion 4267 needs to be detected within the event time interval 4263 or the state machine transitions to the alarm state 4203. The use of breathing event identification states is described in more detail in FIG. 17A.

Figure 17A:
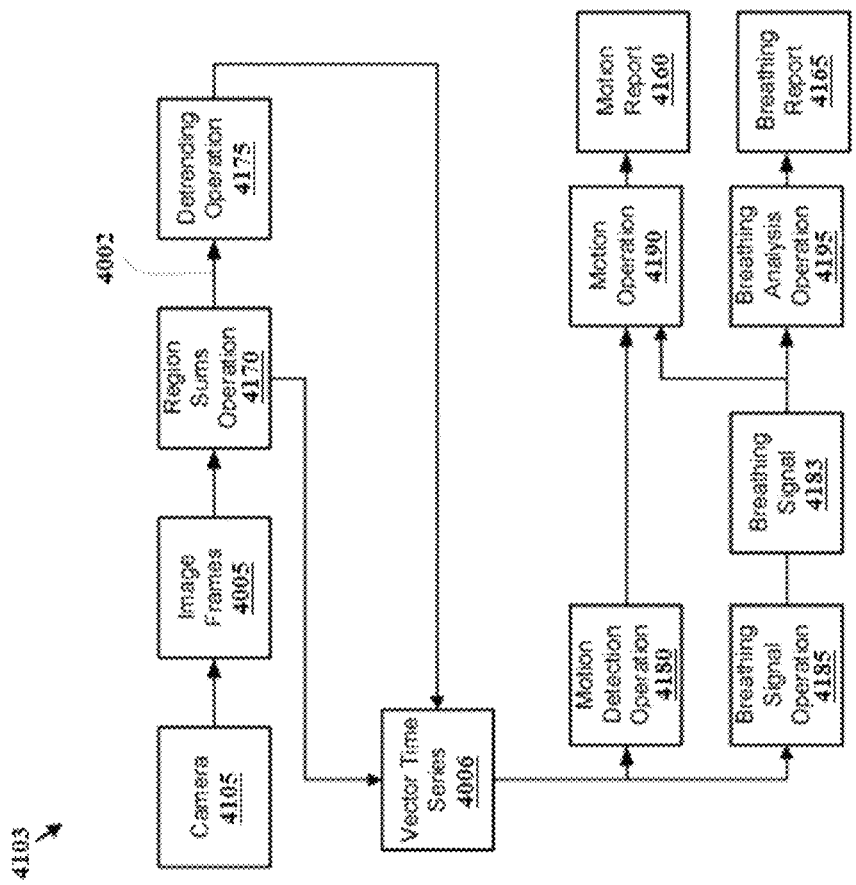
FIG. 17A is a schematic block diagram of a breathing event identification process in accordance with one or more embodiments of the present disclosure.

FIG. 17A is a schematic block diagram of a breathing event identification process 4103 in accordance with one or more embodiments of the present disclosure. The video stream 4120 of a subject may include image frames 4005 that may be captured by a camera 4105. The camera 4105 may output image frames 4005. Image frames 4005 may be produced in many different formats including color images with red, green, and blue color channels, grayscale images, infrared images, depth images. Some formats may be derived from others. For example, grayscale image frames 4005 may be computed from red, green, and/or blue images.

In some embodiments, a sequence of operations may be applied to extract a breathing signal 4183. The order in which the operations may be performed may vary. A region sums operation 4170 may compute region sums 4002. The region sums operation 4170 may add together all the pixels intensities lying in a region 4003 of the image frame 4005. The regions 4003 may have different shapes. For example, the image frame 4005 may be divided into a rectangular grid of regions as shown in FIG. 16A. The regions may be circularly shaped as illustrated in FIG. 16B-D. The regions may be vertical or horizontal lines across the image. Other contours besides straight lines may also be used. The regions may be overlapping as illustrated in FIG. 16C or non-overlapping as illustrated in FIG. 16B. Not every pixel in the image frame 4005 may need to be included in a region as illustrated in FIGS. 16B-C.

In some embodiments, the selection of regions 4003 may be guided by an input from a user through a graphical user interface as illustrated in FIG. 16D. Once region selection with the user input is performed, the regions 4003 may be held fixed during the remainder of the processing. In some embodiments, computing the region sums 4002 may not be needed. In some embodiments, subsequent operations may be performed directly on the pixel intensities.

In some embodiments, the output of the region sums operation 4170 may be a vector time series 4006 in which there is one element in the vector for each region. When region sums 4002 are not computed, the vector may include one element for each pixel in the image frame.

Figure 17B:
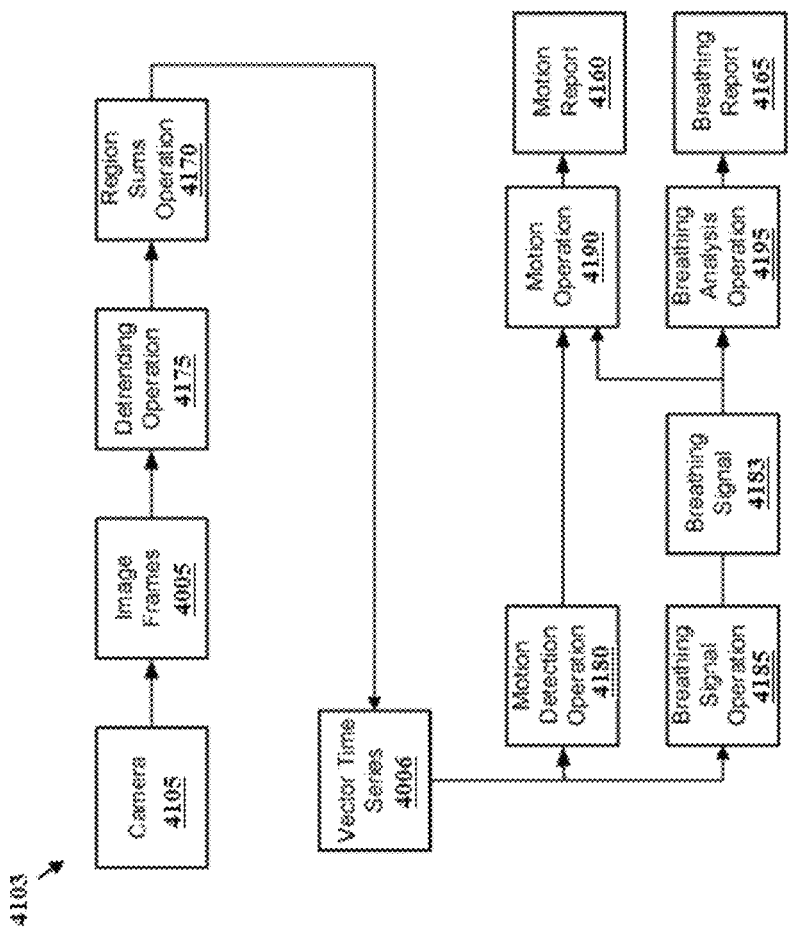
FIG. 17B is a schematic block diagram of a breathing event identification process in accordance with one or more embodiments of the present disclosure.

In the depicted embodiments, the detrending operation 4175 may be applied after computing the region sums 4002. However, the region sums operation 4170 and the detrending operation 4175 may be performed in the opposite order as shown in FIG. 17B. The detrending operation 4175 may remove a signal mean in a region 4003. The detrending operation 4175 may also normalize an amplitude of the signal for the region 4003. In that the region sums operation 4170 may combine pixels spatially across one image frame 4005, the detrending operation 4175 may operate on a signal in the temporal dimension. The detrending operation 4175 may not be needed. In some embodiments, the detrending operation 4175 may not be performed. The dimension of the vector time series 4006 output by the detrending operation 4175 may be the same as its input to the detrending operation 4175.

In some embodiments, the breathing signal operation 4185 may estimate the breathing signal 4183. In some embodiments, a sparse plus low-rank decomposition may be used as illustrated hereinbelow in FIG. 17C. In some embodiments, the breathing signal operation 4185 may use subspace tracking. Breathing may lead to small variations in pixel intensities that may be concentrated in areas of the image frame 4005 that are unknown a priori. Breathing manifests itself as quasiperiodic variations in certain region sums 4002. Not all region sums 4002 may be affected by breathing. In regions where it is present, the phase of the breathing signal 4183 may be opposite to the phase of the breathing signal 4183 in other regions. The breathing signal operation 4185 may automatically combine the region sums 4002 that exhibit breathing and neglect those regions sums 4002 that do not exhibit breathing. This automatic breathing signal operation 4185 may also account for the phase of the breathing signal 4183 in regions 4003 where breathing is present.

In some embodiments, one process for combining the region sums 4002 may be to use a linear combination. The coefficients in the linear combination may be set to include regions 4003 where breathing is present and exclude regions 4003 where breathing is absent. When a coefficient is set to zero, the corresponding region sum 4002 may not be included in the final estimate of the breathing signal. When a coefficient is nonzero, the corresponding region sum 4002 may be included in the linear combination. The algebraic sign of the coefficient (positive or negative) may be used to coherently combine region sums 4002 and to account for the phase of the breathing signal 4183 in each region sum 4002. The weights and/or coefficients in a linear combination of the region sums 4002 may be automatically selected to include regions 4003 where breathing is present and may exclude regions 4003 where breathing is absent. The resulting linear combination may be a scalar-valued time series which is the final breathing signal 4183. Subspace tracking may be used to automatically adjust the coefficients in the linear combination. In some embodiments, singular value decomposition may be used for the subspace tracking.

In some embodiments, an adaptive subspace algorithm such as a Projection Approximation Subspace Tracking (PAST) that is adapted to image processing may be used. The adaptive subspace algorithm may adaptively update estimates of an orthonormal basis for pixel vector space spanned by the incoming pixel vectors. The dominant basis vector learned by the adaptive subspace algorithm may be used as the coefficients in the linear combination. In addition, one of the steps in the adaptive subspace algorithm may be to compute the linear combination. Thus, the adaptive subspace algorithm may compute an estimate of the breathing signal 4183.

In some embodiments, the adaptive subspace algorithm may be applied to the vector of region sums 4002. It may also be applied to the raw pixels in the original image frame 4005. The adaptive subspace algorithm may also be applied to the video stream of moving objects obtained from a sparse plus low-rank decomposition. Alternative algorithms for subspace tracking and subspace updating may also be used.

In some embodiments, after the breathing signal 4183 is estimated, a breathing analysis operation 4195 may be performed and a breathing report 4165 may be produced. The breathing report 4165 may include a variety of information, including a current breath rate 4231. The breath rate 4231 may be saved over a period of time in the breathing report 4165 so that breathing history may be analyzed and reported. Breathing variability may also be reported. Irregular breathing and breathing anomalies may be of interest. Breathing analysis may include the minimum inter-breath interval 4233, maximum inter-breath interval 4235, and/or the inter-breath interval statistics 4237 such as mean, median, mode, standard deviation, etc. The inter-breath interval histogram 4239 may be computed. Apnea events may be counted and time-stamped as the Apnea event data 4241.

In some embodiments, the motion operation 4190 may generate the motion report 4160. The motion operation 4190 may employ the breathing event identification states of FIG. 16E. Breathing may only be accurately measured when the subject is relatively still. When, for example, a sleeping infant rolls over in the crib, the large-scale motion 4267 causes large intensity changes in image pixels that lead to large region sum values. This masks the breathing signal 4183. Therefore, large-scale motion 4267 may be detected. If the subject's breathing stops, a caregiver would want to be alerted in order to respond and resuscitate the child. Information about motion may be included in the region sums 4002. Motion may be detected using a classic hypothesis test. The null hypothesis is where no motion is present. The alternative is that motion is present. Motion may cause a significant rise in the variance of region sums, detecting the motion. Classic detection methods may be applied. Machine learning techniques may also be applied.

In some embodiments, absence of both large-scale motion 4267 and breathing events 265 may indicate that an alert should be generated. The region sums 4002 may be analyzed to detect when all motion and breathing stop. The estimated breathing signal 4183 may provide additional information. The region sums 4002 and breathing signal 4183 may be fed into a motion operation 4190. The motion operation 4190 may employ the breathing event identification states of FIG. 16E. Transitions between the normal breathing state 4201 and the motion state 4205 may be detected by the hardware modules 4116. The alarm state 4203 may be entered when all large-scale motion 4267 goes to zero and when the breathing signal 4183 drops below a prescribed level and/or no breathing events 4265 are detected.

In some embodiments, a motion report 4160 may be generated and provide information to a user. Motion and breathing information may be used to evaluate the sleep length 4249 and the sleep quality 4251. The onset and ending of sleep intervals 4253 may be time-stamped.

FIG. 17B is a schematic block diagram of a breathing event identification process 4103 in accordance with one or more embodiments of the present disclosure. The process 4103 of FIG. 17A is shown with the detrending operation 4175 performed before the region sums operation 4170.

Figure 17C:
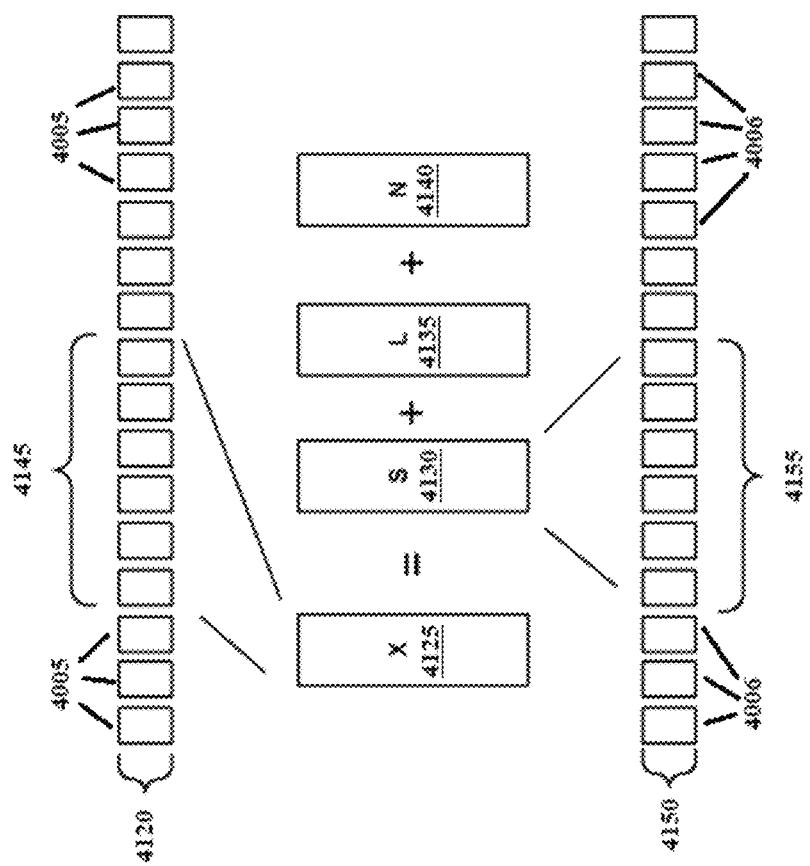
FIG. 17C is a schematic diagram of a video stream of a moving objects generation process in accordance with one or more embodiments of the present disclosure.

FIG. 17C is a schematic diagram of a video stream of moving objects generation process 4101 in accordance with one or more embodiments of the present disclosure. The process 4101 may generate a video stream of moving objects 4150 from a video stream 4120 that may include image frames 4005 of the subject 4110. The process 4101 may receive the video stream 4120 from the camera 4105. The video stream 4120 may include a sequence of image frames I(t) 4005 that are indexed by a cursor t. In addition, the video stream 4120 may include one or more channels that may include but are not limited to an optical color image channel such as a Red Green Blue (RGB) channel, a grayscale image channel, and an infrared image channel.

In some embodiments, the process 4101 may define a window length N. The process may further extract a windowed video subsequence 4145 from the video stream 4120 as the sequence I(t−N+1), I(t−N+2), I(t−N+3), . . . , I(t−2), I(t−1), I(t). The process 4101 may organize the windowed video sequence into a matrix X 4125. In some embodiments, X 4125 may be an M by N matrix, and may include M rows and N columns.

In some embodiments, M may be calculated as a product of a height of an image frame 4005 of the video stream 4120 in pixels, a width of the image frame 4005 of the video stream 4120 in pixels, and a number of channels in the image frames of the video stream 4120. As a result, the matrix X 4125 may be organized as a plurality of vectors with a vector for each image frame I in the windowed video sequence 4145. The organization of the matrix X 4125 may simplify and enhances the calculation of the breathing event 4265.

In some embodiments, the process 4101 may decompose the matrix X 4125 into a sparse matrix S 4130 representing moving objects, and a low rank matrix L 4135 representing non-moving objects as will be described hereinbelow. In some embodiments, the decomposition of matrix X 4125 may include an additive noise matrix N 4140.

In some embodiments, the process 4101 may reconstruct the video stream of moving objects 4150 from the sparse matrix S 130. In some embodiments, each pixel of the reconstructed video stream of moving objects 4150 may include a scaler time series. Alternatively, each pixel of the reconstructed video stream of moving objects 4150 may include a vector time series. In some embodiments, a sliding sparse subsequence 4155 that corresponds to the windowed video sequence 4145 may be extracted from the video stream of moving objects 4150.

Figure 18A:
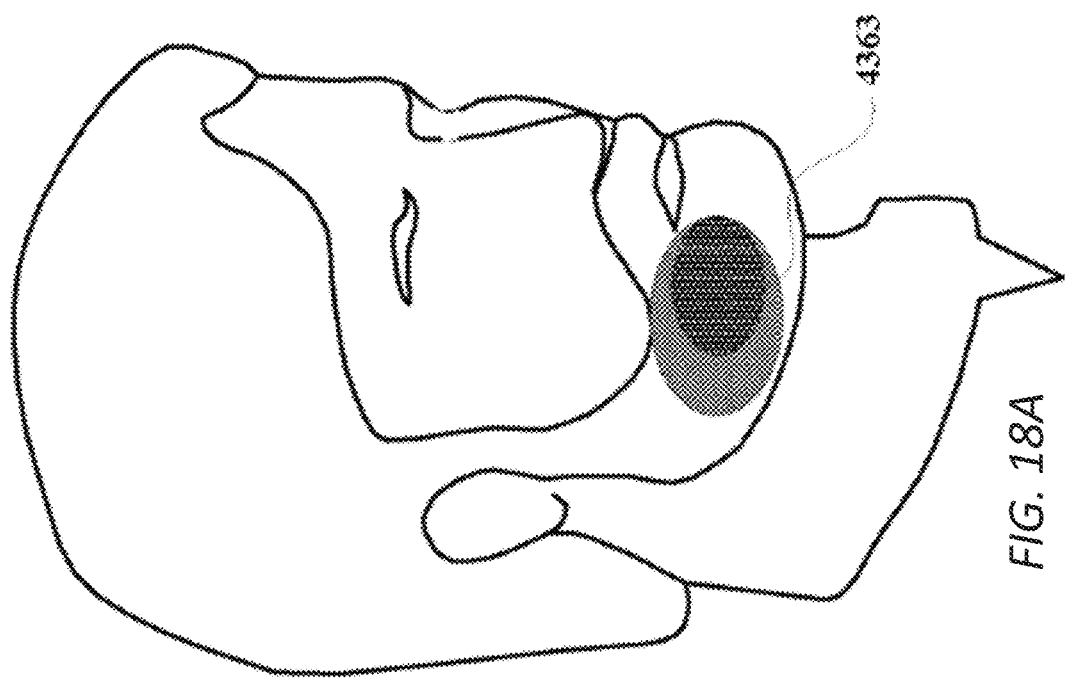
FIG. 18A is a drawing illustrating a heat map in accordance with one or more embodiments of the present disclosure.

FIG. 18A is a drawing illustrating a heat map 4363 in accordance with one or more embodiments of the present disclosure. In the depicted embodiment, a video stream 4120 of the subject 4110 is shown with the heat map 4363 superimposed on the video stream 4120. In some embodiments, the breath rate 4231 from a plurality of breathing events 4265 may be encoded as the heat map 4363. The heat map 4363 may be overlaid on the video stream 4120 for display to a user.

Figure 18B:
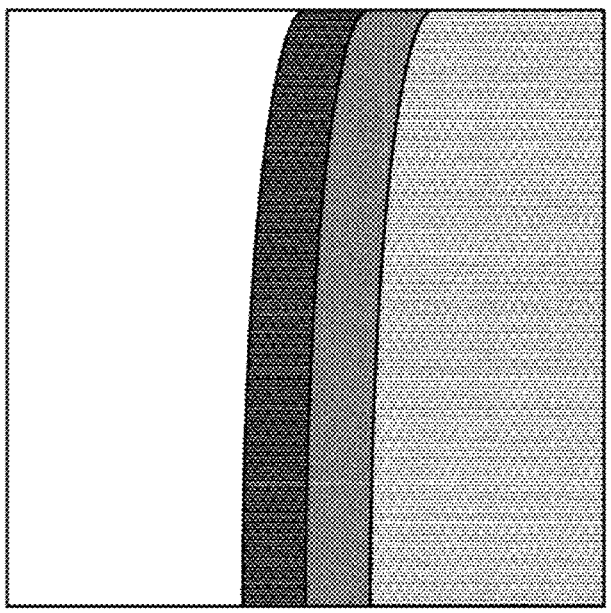
FIG. 18B is a drawing illustrating a heat map in accordance with one or more embodiments of the present disclosure.

FIG. 18B is a drawing illustrating a heat map 4363 in accordance with one or more embodiments of the present disclosure. In the depicted embodiment, a video stream 4120 of the subject 4110 such as the chest region of the subject 4110 is shown with a heat map 4363 superimposed on the video stream 4120. The heat map 4363 may be encoded with the large-scale motion 4267 of the subject 4110. In some embodiments, the heat map 4363 may encode the motion magnitude 4245 of the subject 4110.

Figure 18C:
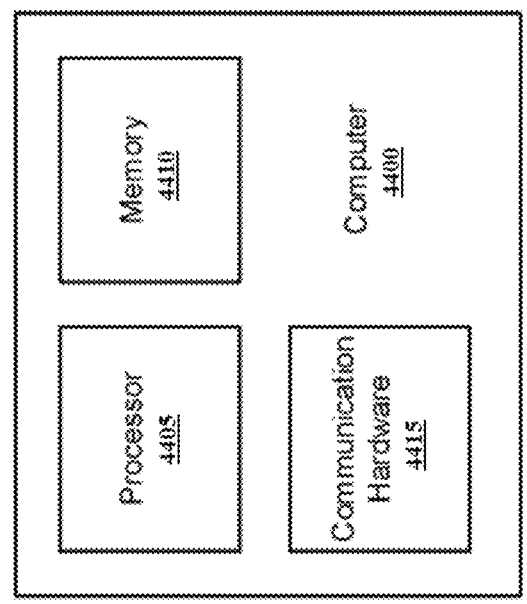
FIG. 18C is a schematic block diagram of the computer in accordance with one or more embodiments of the present disclosure.

FIG. 18C is a schematic block diagram of the computer 4400 in accordance with one or more embodiments of the present disclosure. The computer 4400 may be embodied in the hardware modules 4116. In the depicted embodiment, the computer may include a processor 4405, a memory 4410, and communication hardware 4415. The memory 4410 may include a semiconductor storage device. The memory 4410 may store code. The processor 4405 may execute the code. The communication hardware 4415 may communicate with other elements of the monitor device 4123 and/or other devices such as a mobile telephone network or a Wi-Fi network.

Figure 18D:
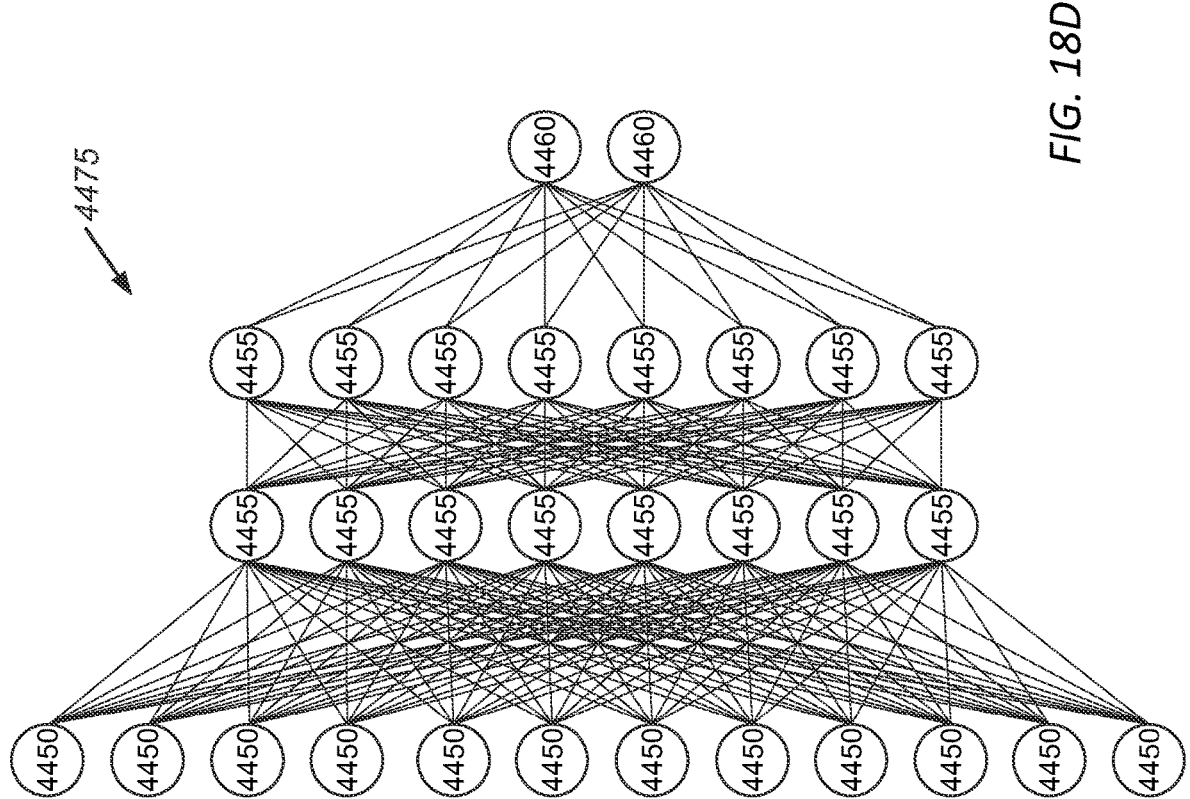
FIG. 18D is a schematic block diagram of a neural network in accordance with one or more embodiments of the present disclosure.

FIG. 18D is a schematic block diagram of a neural network 4475 in accordance with one or more embodiments of the present disclosure. In the depicted embodiment, the neural network 4475 may include one or more hidden neurons 4455. The hidden neurons 4455 may receive inputs from one or more input neurons 4450 and may communicate with one or more output neurons 4460. The output neurons 4460 may indicate predictions such as breathing normally and/or moving. The neural network 4475 may be trained with one or more video streams 4120 and one or more motion reports 4160 and/or breathing reports 4165 corresponding to the one or more video streams 4120. In addition, a live video stream 4120 may be presented to the input neurons 4450 of the trained neural network 4475 and the output neurons 4460 may generate a current motion report 4160 and/or a current breathing report 4165.

Figure 19A:
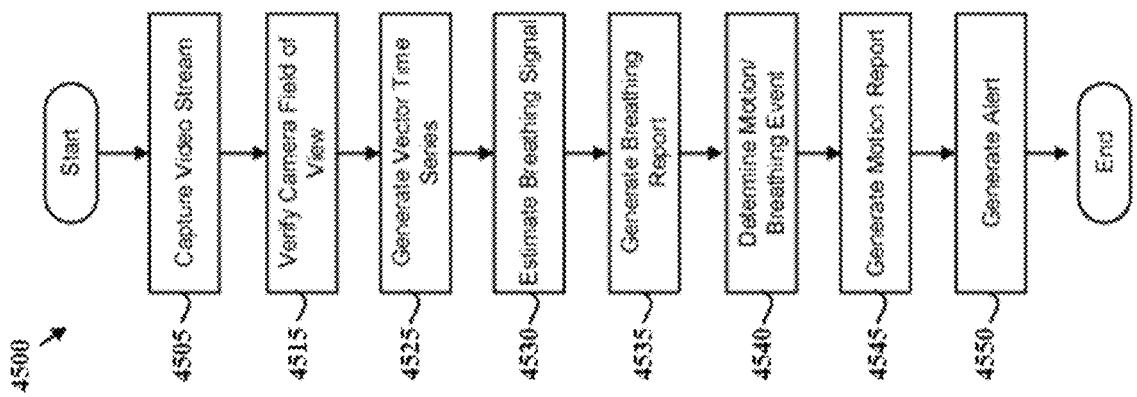
FIG. 19A is a flowchart of a breathing signal estimation method in accordance with one or more embodiments of the present disclosure.

FIG. 19A is a flowchart of a breathing signal estimation method 4500 in accordance with one or more embodiments of the present disclosure. The method 4500 may generate the breathing report 4165, the motion report 4160, and/or generate an alert. The method 4500 may be performed by the monitor device 4123.

In some embodiments, the method 4500 starts where the camera 4105 may capture 4505 the video stream 4120 of the subject 4110. The video stream 4120 may be captured 4505 without disturbing the subject 4110. In some embodiments, the video stream 4120 may be captured 4505 in an infrared spectrum.

In some embodiments, the hardware modules 4116 may verify 4515 that the field-of-view of the camera 4105 satisfies the field-of-view policy 4261. In some embodiments, the field-of-view policy 4261 may be satisfied if the subject 4110 fills at least 10% of the field of view of the camera 4105. The hardware modules 4515 may adjust the field-of-view of the camera 4105 until the field-of-view policy 4261 may be satisfied.

In some embodiments, the hardware modules 4116 may generate 4525 the vector time series 4006 for the video stream 4120. The time vector series 4006 may include a vector for each image frame 4005 of the video stream 4120. The hardware modules 4116 may divide each image frame 4005 into regions 4003. In addition, the hardware modules 4116 may sum the pixel values in each region 4003 as a pixel sum as described for FIGS. 17A-B.

In some embodiments, the hardware modules 4116 may generate 4525 the vector time series 4006 by dividing each image frame 4005 into regions 4003 and removing a signal mean in each region 4003 as described for FIGS. 17A-B. In some embodiments, the signal mean may be removed from the pixel sums.

In some embodiments, the hardware modules 4116 may estimate 4530 the breathing signal 4183 from the vector time series 4006. The breathing signal 4183 may be estimated 4530 from the reconstructed video stream as described hereinbelow in FIG. 19B. In addition, the breathing signal 4183 may be estimated 4530 by applying the adaptive subspace algorithm to each vector of the vector time series 4006. The hardware modules 4116 may further estimate a breathing event 4265 from the breathing signal 4183.

In some embodiments, the hardware modules 4116 may generate 4535 the breathing report 4165. The breathing report 4165 may be generated 4535 based on the breathing signal 4183 and/or the breathing event 4265.

In some embodiments, the hardware modules 4116 may determine 4540 one of a large-scale motion 4267 and a breathing event 4265 of the subject 4110 based on the vector time series 4006 and/or the breathing signal 4183. The hardware modules 4116 may further generate 4545 the motion report 4160 based on the large-scale motion 4267.

In some embodiments, the hardware modules 4116 may generate 4550 an alert and the method 4500 ends. The alert may be communicated through the speaker 4121. In addition, the alert may be communicated through the display 4119. Alternatively, the alert may be communicated through another device such as a mobile telephone.

In some embodiments, the alert may be generated 4550 if both no breathing event 4265 is identified and no large-scale motion 4267 of the subject 4110 is identified within the event time interval 4263. For example, if no breathing event 4265 is identified from the breathing signal 4183 during the event time interval 4263 and no large-scale motion 4267 of the subject 4110 is identified within the event time interval 4263, the breathing event identification states may transition to the alarm state 4203, generating the alert.

Figure 19B:
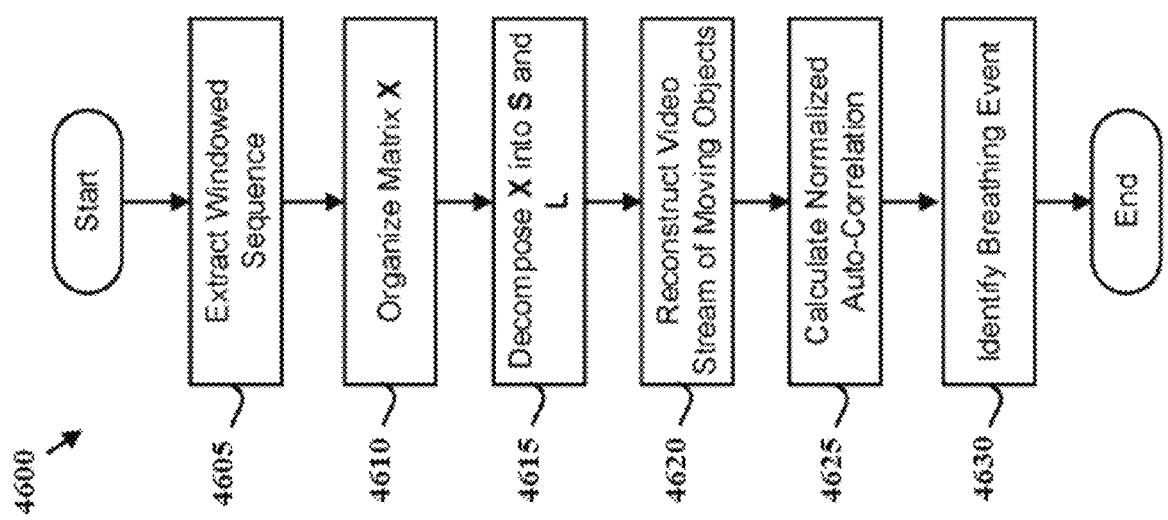
FIG. 19B is a flowchart of a breathing event identification method in accordance with one or more embodiments of the present disclosure.

FIG. 19B is a flowchart of a breathing event identification method 4600 in accordance with one or more embodiments of the present disclosure. The method 4600 may identify a breathing event 4265 from the video stream 4120. The method 4600 may be performed by one or more of the camera 4105, the hardware modules 4116, and/or the memory 4420 storing code.

In some embodiments, the method 4600 starts and the hardware modules 4116 may extract 4605 the windowed video subsequence 4145 from the video stream 4120. In addition, the hardware modules 4116 may organize 4610 the windowed video subsequence 4145 into the matrix X 4125 as described in FIG. 16A-C.

In some embodiments, the hardware modules 4116 may decompose 4615 the matrix X 4125 into the sparse matrix S 4130 and the low rank matrix L 4135. In some embodiments, the matrix X 4125 may be decomposed 4615 using Equation 1.

$$X=S+L+N \qquad \text{Eq. 8}$$

In some embodiments, the hardware modules 4116 may further initialize matrix S 4130 to S=0. In addition, the hardware modules 4116 may calculate the low rank matrix L 4135 using Equation 2.

$$L=\text{mean}(X-S) \qquad \text{Eq. 9}$$

In some embodiments, the "mean" operator may return a matrix L having the same dimensions as the input X−S in which each element on the $i^{th}$ row of L is the mean value (average value) of the corresponding row of the input X−S.

In some embodiments, the hardware modules 4116 may calculate each pixel of matrix S 4130 using Equation 3, where $S_{(i,j)}$ denotes the element on the $i^{th}$ row of the matrix S and the $j^{th}$ column of the matrix S, and T is a sparsity threshold. The sparsity threshold may be set such that a specified percentage of elements in a specified matrix is populated.

$$S_{(i,j)} = \begin{cases} X_{(i,j)} - L_{(i,j)}, & \text{if } |X_{(i,j)} - L_{(i,j)}| < T \\ 0, & \text{otherwise} \end{cases} \qquad \text{Eq. 10}$$

The hardware modules 4116 may iteratively repeat the calculations of Equation 2 and Equation 3 until a stopping condition is satisfied, yielding the sparse matrix S 4130.

In some embodiments, the hardware modules 4116 may further reconstruct 4620 the video stream of moving objects 4150 from the sparse matrix S 4130. In some embodiments, each column vector of the sparse matrix S 4130 may be reconstructed 4620 as a video frame of the video stream of moving objects 4150.

In some embodiments, the hardware modules 4116 may reconstruct 4620 the video stream of moving objects 4150 from a plurality of sparse matrices S 4130 for a plurality of windowed video sequences 4145 and the method 4600 ends. The hardware modules 4116 may combine corresponding vectors of each sparse matrix S 4130 to reconstruct 4620 the video stream of moving objects 4150.

In some embodiments, the hardware modules 4116 may calculate 625 a normalized auto-correlation for each pixel time series of the reconstructed video stream of moving objects 4150. The hardware modules 4116 may identify 4630 a breathing event 4265 in response to an auto-correlation peak for a given pixel of the reconstructed video stream of moving objects 4150 persisting over a specified number of consecutive time periods, and the method 4600 ends. The time lag of the auto-correlation peak may indicate the period of breathing. The reciprocal of the time lag may indicate the breath rate.

In some embodiments, the use of the reconstructed video stream of moving objects 4150 reduces the computational overhead of calculating the breathing signal 4183. As a result, the breathing signal 4183 may be calculated using limited processing power. As a result, the monitor device 4123 may be fabricated at significantly reduced cost. In addition, the monitor device 4123 may consume much less power, and may be powered by a battery. As a result, the utility of the monitor device 4123 may be significantly increased.

Figure 19C:
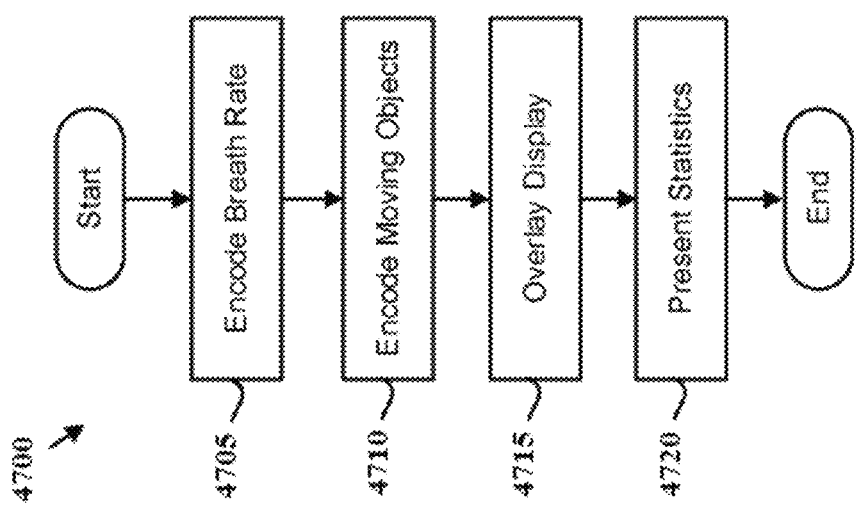
FIG. 19C is a flowchart of a breathing event communication method in accordance with one or more embodiments of the present disclosure.

FIG. 19C is a flowchart of a breathing event communication method 4700 in accordance with one or more embodiments of the present disclosure. The method 4700 may encode and communicate information based on the breathing event. The method 4700 may be performed by the monitor device 4123.

In some embodiments, the method 4700 starts, and the hardware modules 4116 may encode 4705 a breath rate 4231 from a plurality of breathing events. In other embodiments, the breath rate 4231 may be calculated as a function of an average time interval between each of the plurality of breathing events 4265. The hardware modules 4116 may further encode 4705 the breath rate 4231 as a heat map 4363. In some embodiments, a breath rate 4231 within a normal range may be assigned a first heat map value and a breath rate outside of the normal range may be assigned a second heat map value. Alternatively, the heat map value may be equal to a function of the breath rate 4231.

In some embodiments, the hardware modules 4116 may further encode 4710 the moving objects of the video stream of moving objects 4150 as a heat map 4363. A moving object value for each pixel may be calculated as a function of a number of corresponding pixels in a sliding sparse subsequence 4155 that include moving objects. The heat map value for each pixel may be the moving object value.

In some embodiments, the hardware modules 4116 may overlay 4715 the heat map 4363 on the video stream 4120 for display to a user. The heat map may be overlaid in a channel of the video stream 4120 such as the alpha channel. For example, the alpha channel of an image frame and/or a pixel may be modified as a function of the heat map value for the image frame and/or for the pixel.

In some embodiments, the hardware modules 4116 may present 4720 statistics to the user using the display 4119 and the method 4700 ends. The statistics may be presented 4620 through the r:4 video stream 4120. The statistics may include the information of the motion report 4160 and/or the breathing report 4165.

In some embodiments, a system for monitoring a baby may include:
an optical subsystem;
a two-way audio system;
a sensor selected from a group consisting of a breathing detector, a heart rate detector and any combination thereof;
a user interface configured to provide a member of a group consisting of an alert to at least one user, one-way communication with a user, two-way communication with at least one user;
a temperature control subsystem for maintaining at least one foodstuff at at least one predetermined temperature; and
a processing unit in communication with the imaging device, the two-way audio system, the user interface and the temperature control subsystem, the processing unit configured to determine, from images of the baby generated by the imaging device, at least one behavioral state of the baby and to generate, from the behavioral state, at least one response;
where the at least one response is selected from a group consisting of providing audio to the baby, providing video to the baby, providing an alert to a user, providing two-way communication between the baby and a user, altering a temperature of the at least one foodstuff, or any combination thereof.

In some embodiments, the system may include at least one projector for generating visual signals.

In some embodiments, the system may be configured to receive at least one of audio and visual signals via the user interface and to display the at least one of audio and visual signals to the baby.

In some embodiments, the system may be configured to display to the baby at least one of audio and visual signals that are prerecorded.

In some embodiments, the system may be configured to display to the baby at least one of audio and visual signals that are interactive.

In some embodiments, at least one of a breathing rate of the baby and at least one heartbeat rate of the baby may be determinable without contact between the system and the baby.

In some embodiments, the system may be configured to determine, from the images of the baby, at least one of a breathing rate of the baby and a heartbeat rate of the baby.

In some embodiments, at least one of a breathing rate of the baby and a heartbeat rate of the baby is measurable via photoplethysmography (PPG).

In some embodiments, the system may be configured to generate an alert when the heartbeat rate is outside a range of 40 to 180 beats per minute.

In some embodiments, the system may be configured to generate an alert when a frequency of determination of at least one of a breathing rate of the baby and a heartbeat rate of the baby is in a range between once every 0.1 s and once every 20 s.

In some embodiments, the system may be configured to determine the heartbeat rate from skin pixels of exposed skin of a portion of a body such as a face, a neck, a torso, an arm, a hand, a leg, and/or a foot.

In some embodiments, the behavioral state of the baby may include an asleep state, an awake state, an awakening state, a tired state, an alert state, a bored state, a distressed state, a state of falling asleep, and/or a hungry state.

In some embodiments, the system may be configured to enable two-way communication between the baby and the user.

In some embodiments, the system may be configured for a plurality of users.

In some embodiments, the temperature controller may include a Peltier device, an infrared heater, a heating mantle, a heating tape, a microwave source, a hot air source, a cooling mantle, a cold air source, a circulating cold liquid source, and/or an evaporative cooling source.

In some embodiments, the temperature controller may control a temperature via a single device the provides both heating and cooling.

In some embodiments, the temperature controller may control a temperature via different devices for heating and cooling.

In some embodiments, the system may further include a temperature detector for detecting a temperature of the baby.

In some embodiments, the temperature detector may be a non-contact temperature detector.

In some embodiments, the temperature detector may be selected from a group consisting of an infrared thermometer, an infrared temperature sensor, a thermal imaging system, an infrared thermographic system, a thermal imaging camera, and a bolometer.

In some embodiments, the system may be configured to measure a blood oxygen level.

In some embodiments, the blood oxygen level may be measurable via photoplethysmography (PPG).

In some embodiments, the system may be configured to determine the heartbeat rate via steps including:
  detecting an object of interest (OOI) from video data;
  tracking, the OOI;
  identifying a region of interest (ROI) within the OOI;
  generating super pixels from pixels within the ROI;
  generating a super-pixel time series;
  modeling the super-pixel time series as a super-pixel model;
  using the super pixel model to calculate at least one of a heartbeat signal, and another heart characteristic; and
  remotely estimating the heartbeat rate from the heartbeat signal.

In some embodiments, the processor may be configured to determine the breathing rate via steps including:
  detecting an object of interest (OOI) from video data;
  tracking, the OOI;
  identifying a region of interest (ROI) within the OOI;
  generating super pixels from pixels within the ROI;
  generating a super-pixel time series;
  modeling the super-pixel time series as a super-pixel model;
  using the super pixel model to calculate at least one of a breathing signal, and another breathing characteristic; and
  remotely estimating the breathing rate from the breathing signal.

In some embodiments, at least one behavioral state of the baby may be determined automatically via artificial intelligence (AI) (e.g., machine learning models).

In some embodiments, a response to the at least one behavioral state may be generated automatically via AI.

In some embodiments, a detection reaction loop for soothing a baby may be configured to:
  (1) provide a soothing method decision-making component;
  (2) collect data from multiple sensors;
  (3) transfer data to a computation unit to create an action list for each response system;
  (4) using the action list, activate a soothing method selected from a group consisting of soothing by sound, a projector to display a soothing video; and activating a vibration unit; activating a functional IoT device; activating a temperature control device to alter a temperature of a foodstuff; controlling an ambient light; activating an IoT device; sending a notification to a user;
  (5) repeat collection of data from the multiple sensors;
  (6) automatically modify the soothing method; and
  (7) repeat the second through sixth steps until baby is soothed.

In some embodiments, the detection reaction loop for soothing a baby additionally may include a step of sending the modified soothing method to a crowdsourcing soothing method server for modification of a generic soothing method decision-making component.

In some embodiments, the detection reaction loop for soothing a baby additionally may include a step of storing the modified soothing method;

In some embodiments, the soothing method decision-making component may be preloaded into the system.

In some embodiments, the soothing method decision-making component may be used only locally.

In some embodiments, the soothing method decision-making component may include at least one parameter from a crowdsourcing soothing method server In some embodiments, the sensors are selected from a group consisting of an optical subsystem, a microphone, an acoustic/audio detector, and a lidar.

In some embodiments, the sensor output data from the sensors may be used to implement a breathing detector, a temperature detector, and a heart rate detector.

In some embodiments, the computation unit may be located in a component that is a camera computation processor and/or a separate processor.

In some embodiments, the computation unit may be configured to carry out the following steps:
  get historic data from a Prior-Data Gate;
  get the sensor data from a Sensor Data Gate;
  analyze the sensor data;
  in the ICDV Calculator, generate, from the analyzed data, inputs for all response systems;
  send the inputs for all response systems to an ICDV-Response Agent Pool, the ICDV Response Agent Pool generates ICVD values for each computation agent;
  send the ICVD values to the Response Recipe Calculator and create an action list for each response system;
  broadcast the action list for each response system through the Response API Pool; and
  update the actions, the IPH and the ICH through the Prior-Data Gate.

In some embodiments, the response systems may include audio, video, and alerts.

In some embodiments, the ICDV-Response Agent Pool is a computation agent.

In some embodiments, the computation agent may include a member of a group consisting of one agent per response system, one agent for many response systems, and/or many agents for at least one system.

In some embodiments, the ICDV-Response Agent Pool may generate, from the analyzed sensor data, at least one ICDV value.

In some embodiments, a plurality of the at least one ICDV value may be weighted to determine a relative importance of the ICDV values.

In some embodiments, the weighting may be predefined and/or AI-generated.

In some embodiments, a sound for soothing may include music, white/pink noise, and/or a user's voice.

In some embodiments, the user's voice may be recorded or live.

In some embodiments, the soothing sound may be characterized by a sound volume, a type of sound, and/or a length of time the sound is emitted.

In some embodiments, an ambient light level variation may be implemented by turning a light on, turning a light off, adjusting a lighting level, and/or changing the color of a light.

In some embodiments, an alert notification may be sent to the user via a mobile application, via an app, via a built-in OS notification, via a telephone, via a phone call, via sound from a speaker system, and/or via a light signal.

In some embodiments, a method of monitoring a baby may include steps of:
    providing a system for monitoring a baby including:
        i. an optical subsystem;
        ii. a two-way audio system;
        iii. a plurality of sensors outputting sensor data configured to implement a breathing detection and/or a heart rate detection;
        iv. a user interface configured to provide a member of a group consisting of an alert to at least one user, one-way communication with a user, two-way communication with at least one user;
        v. a temperature control subsystem for maintaining at least one foodstuff at at least one predetermined temperature; and
        vi. a processing unit in communication with the imaging device, the two-way audio system, the sensor, the user interface and the temperature control subsystem, the processing unit configured to determine, from a baby signal selected from a group consisting of an image of the baby generated by the imaging device, a signal from the sensor and any combination thereof, at least one behavioral state of the baby and to generate, from the behavioral state, at least one response;
    emplacing the optical subsystem within viewing range of the baby;
    emplacing the two-way speaker within hearing range of the baby;
    emplacing the two-way audio system within hearing range of the baby;
    emplacing the sensor within sensing range of the baby;
    activating the system for monitoring a baby, thereby generating the baby signal;
    determining, from the baby signal, the behavioral state of the baby;
    generating, from the behavioral state, the at least one response; and
    selecting the at least one response from a group consisting of providing the audio to the baby, providing the video to the baby, providing the alert to the user, providing the two-way communication between the baby and the user, and altering the temperature of the at least one foodstuff.

In some embodiments, the method may include providing at least one projector for generating visual signals.

In some embodiments, the method may include receiving at least one of audio and visual signals via the user interface and to displaying the at least one of audio and visual signals to the baby.

In some embodiments, the method may include displaying to the baby at least one of audio and visual signals that are prerecorded.

In some embodiments, the method may include displaying to the baby at least one of audio and visual signals that are interactive.

In some embodiments, the method may include determining the at least one of a breathing rate of the baby and a heartbeat rate of the baby without contact between the system and the baby.

In some embodiments, the method may include determining, from the from images of the baby, at least one of a breathing rate of the baby and a heartbeat rate of the baby.

In some embodiments, the method may include measuring at least one of a breathing rate of the baby and a heartbeat rate of the baby via photoplethysmography (PPG).

In some embodiments, the method may include sending an alert when the heartbeat rate is outside a range of 40 to 180 beats per minute.

In some embodiments, the method may include at least one of the following steps:
    determining at least one of a breathing rate of the baby and a heartbeat rate of the baby at a frequency in a range between once every 0.1 s and once every 20 s;
    determining the heartbeat rate from skin pixels of exposed skin of a portion of a body selected from a group consisting of a face, a neck, a torso, an arm, a hand, a leg, and a foot;
    selecting the behavioral state of the baby from a group consisting of an asleep state, an awake state, an awakening state, a tired state, an alert state, a bored state, a distressed state, a state of falling asleep, and a hungry state.

In some embodiments, the method may include providing two-way communication between the baby and the user.

In some embodiments, the method may include configuring the system for a plurality of users.

In some embodiments, the method may include providing a temperature controller that the temperature controller may include a Peltier device, an infrared heater, a heating mantle, a heating tape, a microwave source, a hot air source, a cooling mantle, a cold air source, a circulating cold liquid source, and/or an evaporative cooling source.

In some embodiments, the temperature controller may control the temperature via a single device that provides both heat and cooling.

In some embodiments, the temperature controller may control the temperature via different devices for heating and cooling.

In some embodiments, the method may include providing a temperature detector for detecting a temperature of the baby.

In some embodiments, the method may include providing the temperature detector as a non-contact temperature detector.

In some embodiments, the method may include selecting the temperature detector from a group consisting of an infrared thermometer, an infrared temperature sensor, a thermal imaging system, an infrared thermographic system, a thermal imaging camera, and a bolometer.

In some embodiments, the method may include measuring a blood oxygen level.

In some embodiments, the method may include measuring a blood oxygen level via photoplethysmography (PPG).

In some embodiments, the method may include determining the heartbeat rate via steps of:
    detecting an object of interest (OOI) from video data;
    tracking, the OOI;
    identifying a region of interest (ROI) within the OOI;
    generating super pixels from pixels within the ROI;
    generating a super-pixel time series;
    modeling the super-pixel time series as a super-pixel model;

using the super pixel model to calculate at least one of a heartbeat signal, and another heart characteristic; and
remotely estimating the heartbeat rate from the heartbeat signal.

In some embodiments, the method may include determining the breathing rate via steps of:
detecting an object of interest (OOI) from video data;
tracking, the OOI;
identifying a region of interest (ROI) within the OOI;
generating super pixels from pixels within the ROI;
generating a super-pixel time series;
modeling the super-pixel time series as a super-pixel model;
using the super pixel model to calculate at least one of a breathing signal, and another breathing characteristic; and
remotely estimating the breathing rate from the breathing signal.

In some embodiments, the method may include automatically determining the at least one behavioral state of the baby via AI.

In some embodiments, the method may include automatically generating the response to the behavioral state via AI.

In some embodiments, the method may include providing a detection reaction loop for soothing a baby including steps of:
(1) providing a soothing method decision-making component;
(2) collecting data from multiple sensors;
(3) transferring data to a computation unit to create an action list for each response system;
(4) using the action list, activating a soothing method selected from a group consisting of soothing by sound, a projector to display a soothing video; and activating a vibration unit; activating a functional IoT device; activating a temperature control device to alter a temperature of a foodstuff; controlling an ambient light; activating an IoT device; sending a notification to a user;
(5) repeating collection of data from the multiple sensors;
(6) automatically modifying the soothing method; and
(7) repeating the second through sixth steps until baby is soothed.

In some embodiments, the method may include sending the modified soothing method to a crowdsourcing soothing method server for modification of a generic soothing method decision-making component.

In some embodiments, the method may include the following steps:
storing the modified soothing method;
preloading the soothing method decision-making component into the system;
using the soothing method decision-making component only locally;
where the soothing method decision-making component may include at least one parameter from a crowdsourcing soothing method server;
selecting the sensors from a group consisting of an optical subsystem, a microphone, an acoustic/audio detector, a temperature detector, and a lidar;
using sensor output data to implement breathing detection and heart rate detection;
locating for the computation unit in a component selected from a camera computation processor or a separate processor.

In some embodiments, the method may include the computation unit additionally carrying out steps of:
getting historic data from a Prior-Data Gate;
getting the sensor data from a Sensor Data Gate;
analyzing the sensor data;
in the ICDV Calculator, generating, from the analyzed data, inputs for all response systems;
sending the inputs for all response systems to an ICDV-Response Agent Pool, the ICDV Response Agent Pool generates ICVD values for each computation agent;
sending the ICVD values to the Response Recipe Calculator and create an action list for each response system;
broadcasting the action list for each response system through the Response API Pool; and
updating the actions, the IPH and the ICH through the Prior-Data Gate.

In some embodiments, the method may include selecting the response systems with audio, video, and/or alert.

In some embodiments, the ICDV-Response Agent Pool may include a computation agent.

In some embodiments, the computation agent may include one agent per response system, one agent for many response systems, and/or many agents for at least one method.

In some embodiments, the method may include the ICDV-Response Agent Pool producing, from the analyzed sensor data, at least one ICDV value.

In some embodiments, the method may include weighting a plurality of the at least one ICDV value to determine a relative importance of the ICDV values.

In some embodiments, the method may include selecting the weighting from a group consisting of a predefined weight and an AI-generated weight.

In some embodiments, the method may include selecting the soothing sound from a group consisting of music, white/pink noise, and a user's voice.

In some embodiments, the method may include providing at least one of a recorded voice, and a live voice.

In some embodiments, the method may include varying soothing sound characteristics, where the soothing sound characteristic may include a sound volume, a type of sound, and/or a length of time the sound is emitted.

In some embodiments, the method may include selecting an ambient light level variation from a group consisting of turning a light on, turning a light off, adjusting a lighting level, and changing the color of a light.

In some embodiments, the method may include sending the alert notification via a mobile application, an app, a built-in OS notification, a telephone, a phone call, a sound from a speaker system, and/or a light signal.

In some embodiments, a system may include:
a non-volatile memory;
at least one electronic resource including a database;
where the database includes:
(i) baby-specific stimuli data for a plurality of baby-specific stimuli provided to a plurality of babies,
(ii) baby-specific response data for a plurality of baby-specific responses acquired in response to the plurality of baby-specific stimuli provided to the plurality of babies, and
(iii) baby-specific personal data for each baby in the plurality of babies;
an optical subsystem including an imaging device, a projection device, or both.
where the optical subsystem is configured to perform at least one of:
(i) acquire image data from the imaging device of an image of at least one baby from the plurality of babies, or (ii) project by the projection device, at least one visual image to be viewed by the at least one baby;
an audio system including a microphone, a speaker, or both;
  where the audio system is configured to perform at least one of:
  (i) receive by the microphone, audio signal data from the at least one baby, or
  (ii) generate by the speaker, at least one sound for the at least one baby;
a plurality of sensors outputting sensor data;
a communication circuitry configured to communicate over a communication network with at least one communication device of at least one user associated with the at least one baby; and
at least one processor configured to execute code stored in the non-volatile memory that causes the at least one processor to:
  receive the image data, the audio signal data, and the sensor data associated with the at least one baby;
  determine baby-specific physiological data of the at least one baby based on the image data, the sensor data, and the audio signal data;
  where the baby-specific physiological data includes:
  (i) breathing rate signal data of the at least one baby,
  (ii) spatial body temperature distribution data of the at least one baby,
  (iii) heartbeat signal data of the at least one baby,
  (iv) baby motion data of the at least one baby, and
  (v) baby voice classification data of the at least one baby;
  input to at least one baby-specific behavioral state detection machine learning model, the image data, the audio signal data, the sensor data, the baby-specific physiological data, and the baby-specific personal data indicative of a current behavioral state of the at least one baby;
    where the at least one baby-specific behavioral state detection machine learning model is trained using a dataset based at least in part on the baby-specific stimuli data, the baby-specific response data, and the baby-specific personal data associated with the plurality of babies;
  receive an output with at least one environmental action from the at least one baby-specific behavioral state detection machine learning model;
  where the output includes at least one environmental action, at least one behavioral recommendation, or both to change the current behavioral state of the at least one baby to a predefined behavioral state; and
  perform, based on the output, at least one of:
  (i) transmit instructions to the projection device, the speaker, at least one peripheral device, at least one internet of things (IoT) device, or any combination thereof to implement the at least one environmental action, and
  (ii) display on a graphic user interface of at least one communication device of at least one user associated with the at least one baby, the at least one behavioral recommendation.

In some embodiments, a method may include:
receiving, by a processor, from at least one electronic resource including a database;
  where the database includes:
  (i) baby-specific stimuli data for a plurality of baby-specific stimuli provided to a plurality of babies,
  (ii) baby-specific response data for a plurality of baby-specific responses acquired in response to the plurality of baby-specific stimuli provided to the plurality of babies, and
  (iii) baby-specific personal data for each baby in the plurality of babies;
receiving, by the processor, from an imaging device, image data of an image of at least one baby from the plurality of images;
receiving, by the processor, from a microphone, the audio signal data of the at least one baby;
receiving, by the processor, from a plurality of sensors, sensor data associated with the at least one baby;
determining, by the processor, baby-specific physiological data of the at least one baby based on the image data, the sensor data, and the audio signal data;
  where the baby-specific physiological data includes:
  (i) breathing rate signal data of the at least one baby,
  (ii) spatial body temperature distribution data of the at least one baby,
  (iii) heartbeat signal data of the at least one baby,
  (iv) baby motion data of the at least one baby, and
  (v) baby voice classification data of the at least one baby;
inputting, by the processor, to at least one baby-specific behavioral state detection machine learning model, the image data, the audio signal data, the sensor data, the baby-specific physiological data, and the baby-specific personal data associated with the at least one baby;
  where the at least one baby-specific behavioral state detection machine learning model is trained using a dataset based at least in part on the baby-specific stimuli data, the baby-specific response data, and the baby-specific personal data associated with the plurality of babies; receiving, by the processor, an output with at least one environmental action from the at least one baby-specific behavioral state detection machine learning model;
  where the output includes at least one environmental action, at least one behavioral recommendation, or both to change the current behavioral state of the at least one baby to a predefined behavioral state; and
  performing, by the processor, based on the output, at least one of:
  (i) transmitting, by the processor, instructions to the projection device, the speaker, at least one peripheral device, at least one internet of things (IoT) device, or any combination thereof to implement the at least one environmental action, and
  (ii) displaying, by the processor, on a graphic user interface of at least one communication device of at least one user associated with the at least one baby, the at least one behavioral recommendation.

In some embodiments, a system may include:
a non-volatile memory;
at least one electronic resource may include a database;
  where the database includes:
  (i) baby-specific stimuli data for a plurality of baby-specific stimuli provided to a plurality of babies,
  (ii) baby-specific response data for a plurality of baby-specific responses acquired in response to the plurality of baby-specific stimuli provided to the plurality of babies, and
  (iii) baby-specific personal data for each baby in the plurality of babies;
an optical subsystem may include an imaging device, a projection device, or both;

where the optical subsystem is configured to perform at least one of:
(i) acquire image data from the imaging device of an image of at least one baby from the plurality of babies, or
(ii) project by the projection device, at least one visual image to be viewed by the at least one baby;
an audio system may include a microphone, a speaker, or both;
where the audio system is configured to perform at least one of:
(i) receive by the microphone, audio signal data from the at least one baby, or
(ii) generate by the speaker, at least one sound for the at least one baby;
a plurality of sensors outputting sensor data;
a communication circuitry configured to communicate over a communication network with at least one communication device of at least one user associated with the at least one baby; and
at least one processor configured to execute code stored in the non-volatile memory that causes the at least one processor to:
receive the image data, the audio signal data, and the sensor data associated with the at least one baby;
determine baby-specific physiological data of the at least one baby based on the image data, the sensor data, and the audio signal data;
where the baby-specific physiological data includes:
(i) breathing rate signal data of the at least one baby,
(ii) spatial body temperature distribution data of the at least one baby,
(iii) heartbeat signal data of the at least one baby,
(iv) baby motion data of the at least one baby, and
(v) baby voice classification data of the at least one baby;
input to at least one baby-specific behavioral state detection machine learning model, the image data, the audio signal data, the sensor data, the baby-specific physiological data, and the baby-specific personal data associated with the at least one baby;
where the at least one baby-specific behavioral state detection machine learning model may be trained using a dataset based at least in part on the baby-specific stimuli data, the baby-specific response data, and the baby-specific personal data associated with the plurality of babies;
receive an output from the at least one baby-specific behavioral state detection machine learning model that the at least one baby is agitated, about to wake up, or both;
transmit over the communication network, to the at least one communication device of the at least one user, the sensor data, an alert that the at least one baby is agitated, an alert that the at least one baby is about to wake up, or any combination thereof;
transmit instructions based on the output that cause the audio system, the optical subsystem, or both, to perform at least one of:
(i) generate by the speaker, a soothing sound when the at least one baby is agitated,
(ii) generate by the speaker, a sleep-enhancing sound when the at least one baby is about to wake up, or
(iii) project by the projection device, a relaxing image to by viewed by the at least one baby when the at least one baby is agitated.

In some embodiments, the at least one processor may be further configured to iteratively transmit the instruction until the baby is soothed or falls back asleep.

In some embodiments, the at least one processor may be further configured to receive user-instructions from the at least one user through a graphic user interface on the at least one communication device associated with the at least one user.

In some embodiments, the at least one processor may be further configured to transmit the instructions based on the output and the user-instructions from the graphic user interface.

In some embodiments, sensors from the plurality of sensors may be selected from the group consisting of a thermal imager, an infrared (IR) camera, a lidar device, and a radio frequency (RF) device.

In some embodiments, the system may further include a vibration unit operatively coupled to the at least one baby, and where the at least one processor may be further configured to transmit instructions to the vibration unit that causes the vibration unit to apply a vibration to the at least one baby when the baby is agitated.

In some embodiments, the at least one processor may be further configured to transmit the instructions based on the output and the user-instructions from the graphic user interface.

In some embodiments, sensors from the plurality of sensors may be selected from the group consisting of a thermal imaging device, an infrared (IR) camera, a lidar device, and a radio frequency (RF) device.

In some embodiments, a method may include:
receiving, by a processor, from at least one electronic resource including a database;
where the database includes:
(i) baby-specific stimuli data for a plurality of baby-specific stimuli provided to a plurality of babies,
(ii) baby-specific response data for a plurality of baby-specific responses acquired in response to the plurality of baby-specific stimuli provided to the plurality of babies, and
(iii) baby-specific personal data for each baby in the plurality of babies;
receiving, by the processor, from an imaging device, image data of an image of at least one baby from the plurality of images;
receiving, by the processor, from a microphone, the audio signal data of the at least one baby;
receiving, by the processor, from a plurality of sensors, sensor data associated with the at least one baby;
determining, by the processor, baby-specific physiological data of the at least one baby based on the image data, the sensor data, and the audio signal data;
where the baby-specific physiological data may include:
(i) breathing rate signal data of the at least one baby,
(ii) spatial body temperature distribution data of the at least one baby,
(iii) heartbeat signal data of the at least one baby,
(iv) baby motion data of the at least one baby, and
(v) baby voice classification data of the at least one baby;
inputting, by the processor, to at least one baby-specific behavioral state detection machine learning model, the image data, the audio signal data, the sensor data, the baby-specific physiological data, and the baby-specific personal data associated with the at least one baby;

where the at least one baby-specific behavioral state detection machine learning model is trained using a dataset based at least in part on the baby-specific stimuli data, the baby-specific response data, and the baby-specific personal data associated with the plurality of babies;

receiving, by the processor, an output from the at least one baby-specific behavioral state detection machine learning model that the at least one baby is agitated, about to wake up, or both;

transmitting, by the processor, over a communication network, to at least one communication device of at least one user associated with the at least one baby, the sensor data, an alert that the at least one baby is agitated, an alert that the at least one baby is about to wake up, or any combination thereof; and transmitting, by the processor, instructions based on the output that cause a speaker, a projection device, or both, to perform at least one of:
(i) generating by the speaker, a soothing sound when the at least one baby is agitated,
(ii) generating by the speaker, a sleep-enhancing sound when the at least one baby is about to wake up, or
(iii) projecting by the projection device, a relaxing image to by viewed by the at least one baby when the at least one baby is agitated.

In some embodiments, the method includes iteratively transmitting, by the processor, the instruction until the baby is soothed or falls back asleep.

In some embodiments, the method includes receiving, by the processor, user-instructions from the at least one user through a graphic user interface on the at least one communication device associated with the at least one user.

In some embodiments, the method includes transmitting, by the processor, the instructions based on the output and the user-instructions from the graphic user interface.

In some embodiments, a sensor from the plurality of sensors is selected from the group consisting of a video camera, a thermal imager, an infrared (IR) camera, a lidar device, and a radio frequency (RF) device.

In some embodiments, the method includes transmitting, by the processor, instructions to the vibration unit that causes the vibration unit to apply a vibration to the at least one baby when the baby is agitated, where the vibration unit is operatively coupled to the at least one baby.

In some embodiments, a method includes:
receiving, by a processor, from at least one electronic resource including a database;
where the database includes:
(i) baby-specific stimuli data for a plurality of baby-specific stimuli provided to each baby in a plurality of babies,
(ii) baby-specific response data for a plurality of baby-specific responses for each baby acquired in response to the baby-specific stimuli data provided to each baby, and
(iii) baby-specific personal data for each baby in the plurality of babies;

determining, by the processor, from the baby-specific stimuli data and the baby-specific response data for each baby, sensor data from a plurality of sensors, image data from an image device, and audio data from a microphone acquired while monitoring each baby in the plurality of babies;

determining, by the processor, baby-specific physiological data for each baby based on the image data, the sensor data, and the audio signal data;

where the baby-specific physiological data includes:
(i) breathing rate signal data for each baby,
(ii) spatial body temperature distribution data for each baby,
(iii) heartbeat signal data for each baby,
(iv) baby motion data for each baby, and
(v) baby voice classification data for each baby;

executing, by the processor, a physics algorithm module that generates baby-specific features and environmental-specific features for each baby in the plurality of babies unique to a baby soothing use case from the baby-specific physiological data, the image data, the audio signal data, the sensor data, and the baby-specific personal data for each baby;

executing, by the processor, a time driven pipeline software module configured to calculate from the baby-specific features and the environmental-specific features for each baby unique to the baby soothing use case, time-dependent baby-specific features and time dependent environmental-specific features for each baby based at least in part on a time series generated from the baby-specific features and the environmental-specific features that characterize feature progression over time;

executing, by the processor, a behavioral model configured to generate a digital twin model for each baby in the plurality of babies based at least in part on:
(1) a correlation between baby-specific behavioral features from the baby-specific features and the environmental-specific features for each baby, and
(2) the baby-specific stimuli data, the baby-specific response data, and the baby-specific personal data for each baby, executing, by the processor, a feedback environmental generator using the digital twin model of each baby to output at least one recommendation, at least one action, or both to change a behavioral state of each baby in accordance with the baby soothing use case for each baby; and generating, by the processor, a training dataset for the baby soothing use case based at least in part on:
(1) input features for each baby from the plurality of babies including:
(A) the baby-specific features for each baby,
(B) the environmental-specific features for each baby,
(C) the time-dependent baby-specific features for each baby, and
(D) the time dependent environmental-specific features for each baby, and
(2) output features for each baby from the plurality of babies including:
(A) the at least one recommendation for each baby,
(B) the at least one action for each baby, or
(C) both.

In some embodiments, the method includes training, by the processor, at least one baby-specific behavioral state detection machine learning model with the training dataset unique to the baby soothing use case.

In some embodiments, the at least one action to soothe each baby is selected from the group consisting of playing a soothing music, applying vibrations via a vibration unit, projecting soothing images, and playing a sleep-enhancing music.

In some embodiments, a system may include:
a non-volatile memory;
at least one electronic resource including at least one database;
  where the at least one database includes:
  (i) baby-specific stimuli data for a plurality of baby-specific stimuli provided to a plurality of babies,
  (ii) baby-specific response data for a plurality of baby-specific responses acquired in response to the plurality of baby-specific stimuli provided to the plurality of babies, and
  (iii) baby-specific personal data for each baby in the plurality of babies;
an imaging device configured to acquire image data of an image of at least one baby from the plurality of babies;
a microphone configured to receive audio signal data from the at least one baby;
a plurality of sensors outputting sensor data;
a communication circuitry configured to communicate over a communication network with at least one communication device of at least one user associated with the at least one baby;
a temperature controller; and
at least one processor configured to execute code stored in the non-volatile memory that causes the at least one processor to:
  receive the image data, the audio signal data, and the sensor data associated with the at least one baby;
  determine baby-specific physiological data of the at least one baby based on the image data, the sensor data, and the audio signal data;
  where the baby-specific physiological data includes:
  (i) breathing rate signal data of the at least one baby,
  (ii) spatial body temperature distribution data of the at least one baby,
  (iii) heartbeat signal data of the at least one baby,
  (iv) baby motion data of the at least one baby, and
  (v) baby voice classification data of the at least one baby;
  input to at least one baby-specific behavioral state detection machine learning model, the image data, the audio signal data, the sensor data, the baby-specific physiological data, and the baby-specific personal data associated with the at least one baby;
  where the at least one baby-specific behavioral state detection machine learning model is trained using datasets based at least in part on the baby-specific stimuli data, the baby-specific response data, and the baby-specific personal data associated with the plurality of babies;
  receive at least one indication from the at least one baby-specific behavioral state detection machine learning model that the at least one baby is hungry;
  transmit over the communication network, to the at least one communication device of the at least one user, an alert to feed the at least one baby, the sensor data, or both; and
  transmit instructions that causes the temperature controller to change the predefined temperature of the at least one foodstuff in preparation to feed the at least one baby.
In some embodiments, the at least one processor is further configured to receive user-instructions from the at least one user through a graphic user interface on the at least one communication device associated with the at least one user.

In some embodiments, the at least one processor is further configured to transmit the instructions based on the at least one indication and the user-instructions from the graphic user interface.

In some embodiments, a sensor from the plurality of sensors is selected from the group consisting of a thermal imager, an infrared (IR) camera, a lidar device, and a radio frequency (RF) device.

In some embodiments, a vibration unit operatively coupled to the at least one baby, and where the at least one processor is further configured to transmit instructions to the vibration unit that causes the vibration unit to apply a vibration to the at least one baby when the baby is hungry.

A method may include:
receiving, by a processor, from at least one electronic resource including a database;
  where the database includes:
  (i) baby-specific stimuli data for a plurality of baby-specific stimuli provided to a plurality of babies,
  (ii) baby-specific response data for a plurality of baby-specific responses acquired in response to the plurality of baby-specific stimuli provided to the plurality of babies, and
  (iii) baby-specific personal data for each baby in the plurality of babies;
receiving, by the processor, from an imaging device, image data of an image of at least one baby from the plurality of images;
receiving, by the processor, from a microphone, the audio signal data of the at least one baby;
receiving, by the processor, from a plurality of sensors, sensor data associated with the at least one baby;
determining, by the processor, baby-specific physiological data of the at least one baby based on the image data, the sensor data, and the audio signal data;
  where the baby-specific physiological data includes:
  (i) breathing rate signal data of the at least one baby,
  (ii) spatial body temperature distribution data of the at least one baby,
  (iii) heartbeat signal data of the at least one baby,
  (iv) baby motion data of the at least one baby, and
  (v) baby voice classification data of the at least one baby;
inputting, by the processor, to at least one baby-specific behavioral state detection machine learning model, the image data, the audio signal data, the sensor data, the baby-specific physiological data, and the baby-specific personal data associated with the at least one baby;
  where the at least one baby-specific behavioral state detection machine learning model is trained using a dataset based at least in part on the baby-specific stimuli data, the baby-specific response data, and the baby-specific personal data associated with the plurality of babies;
receiving, by the processor, an output from the at least one baby-specific behavioral state detection machine learning model that at least one indication from the at least one baby-specific behavioral state detection machine learning model that the at least one baby is hungry;
transmitting, by the processor, over a communication network, to at least one communication device of at least one user associated with the at least one baby, the sensor data, an alert that the at least one baby is agitated, an alert to feed the at least one baby, the sensor data, or both; and transmitting, by the processor, instructions that causes the temperature controller to change the predefined temperature of the at least one foodstuff in preparation to feed the at least one baby.

In some embodiments, the method includes receiving, by the processor, user-instructions from the at least one user through a graphic user interface on the at least one communication device associated with the at least one user.

In some embodiments, the method includes transmitting, by the processor, the instructions based on the at least one indication and the user-instructions from the graphic user interface.

In some embodiments, a sensor from the plurality of sensors is selected from the group consisting of a thermal imager, an infrared (IR) camera, a lidar device, and a radio frequency (RF) device.

In some embodiments, a method may include:
receiving, by a processor, from at least one electronic resource including a database;
  where the database includes:
    (i) baby-specific stimuli data for a plurality of baby-specific stimuli provided to each baby in a plurality of babies,
    (ii) baby-specific response data for a plurality of baby-specific responses for each baby acquired in response to the baby-specific stimuli data provided to each baby, and
    (iii) baby-specific personal data for each baby in the plurality of babies;
determining, by the processor, from the baby-specific stimuli data and the baby-specific response data for each baby, sensor data from a plurality of sensors, image data from an image device, and audio data from a microphone acquired while monitoring each baby in the plurality of babies;
determining, by the processor, baby-specific physiological data for each baby based on the image data, the sensor data, and the audio signal data;
  where the baby-specific physiological data includes:
    (i) breathing rate signal data for each baby,
    (ii) spatial body temperature distribution data for each baby,
    (iii) heartbeat signal data for each baby,
    (iv) baby motion data for each baby, and
    (v) baby voice classification data for each baby;
executing, by the processor, a physics algorithm module that generates baby-specific features and environmental-specific features for each baby in the plurality of babies unique to a baby feeding use case from the baby-specific physiological data, the image data, the audio signal data, the sensor data, and the baby-specific personal data for each baby;
executing, by the processor, a time driven pipeline software module configured to calculate from the baby-specific features and the environmental-specific features for each baby unique to the baby feeding use case, time-dependent baby-specific features and time dependent environmental-specific features for each baby based at least in part on a time series generated from the baby-specific features and the environmental-specific features that characterize feature progression over time;
executing, by the processor, a behavioral model configured to generate a digital twin model for each baby in the plurality of babies based at least in part on:
  (1) a correlation between baby-specific behavioral features from the baby-specific features and the environmental-specific features for each baby, and
  (2) the baby-specific stimuli data, the baby-specific response data, and the baby-specific personal data for each baby,
executing, by the processor, a feedback environmental generator using the digital twin model of each baby to output at least one recommendation, at least one action, or both to change a behavioral state of each baby in accordance with the baby feeding use case for each baby; and
generating, by the processor, a training dataset for the baby feeding use case based at least in part on:
  (1) input features for each baby from the plurality of babies including:
    (A) the baby-specific features for each baby,
    (B) the environmental-specific features for each baby,
    (C) the time-dependent baby-specific features for each baby, and
    (D) the time dependent environmental-specific features for each baby, and
  (2) output features for each baby from the plurality of babies including:
    (A) the at least one recommendation for each baby,
    (B) the at least one action for each baby, or
    (C) both.

In some embodiments, the method includes training, by the processor, the at least one baby-specific behavioral state detection machine learning model with the training dataset unique to the baby feeding use case.

In some embodiments, the at least one action for the at least one baby may include warming the at least one foodstuff.

In some embodiments, a system includes:
a non-volatile memory;
at least one electronic resource including at least one database;
  where the at least one database includes:
    (i) a plurality of baby-specific educational plans for a plurality of babies,
    (ii) baby-specific stimuli data for a plurality of baby-specific stimuli provided to the plurality of babies based on the plurality of baby-specific educational plans,
    (iii) baby-specific response data for a plurality of baby-specific responses acquired in response to the plurality of baby-specific stimuli provided to the plurality of babies, and
    (iv) baby-specific personal data for each baby in the plurality of babies;
an optical subsystem may include an imaging device, a projection device, or both;
  where the optical subsystem is configured to perform at least one of:
    (i) acquire image data from the imaging device of an image of at least one baby from the plurality of babies, or
    (ii) project by the projection device, at least one visual image to be viewed by the at least one baby;
an audio system may include a microphone, a speaker, or both;
  where the audio system is configured to perform at least one of:
    (i) receive by the microphone, audio signal data from the at least one baby, or
    (ii) generate by the speaker, at least one sound for the at least one baby;
a plurality of sensors outputting sensor data;

a communication circuitry configured to communicate over a communication network with at least one communication device of at least one user associated with the at least one baby; and at least one processor configured to execute code stored in the non-volatile memory that causes the at least one processor to:
- project by the projection device, the at least one visual image to the at least one baby based on a baby-specific educational plan from the plurality of baby-specific educational plans for the at least one baby;
- generate by the audio system, the at least one sound associated with the at least one visual image;
- receive the image data, the audio signal data, the sensor data, or any combination thereof associated with the at least one baby;
- determine baby-specific physiological data of the at least one baby based on the image data, the sensor data, and the audio signal data;
- where the baby-specific physiological data includes:
  - (i) breathing rate signal data of the at least one baby,
  - (ii) spatial body temperature distribution data of the at least one baby,
  - (iii) heartbeat signal data of the at least one baby,
  - (iv) baby motion data of the at least one baby, and
  - (v) baby voice classification data of the at least one baby;
- input to at least one baby-specific educational machine learning model, the image data, the audio signal data, the sensor data, the at least one visual image, the at least one sound, the baby-specific physiological data, the baby-specific personal data associated with the at least one baby;

where the at least one baby-specific educational machine learning model is trained using datasets based at least in part on the baby-specific stimuli data, the baby-specific response data, the baby-specific personal data, the plurality of baby-specific educational plans, or any combination thereof associated with the plurality of babies;
- receive an output from the at least one baby-specific educational machine learning model; where the output includes:
  - (i) at least one indication that the at least one baby understood or did not understand the at least one visual image and the at least one sound associated with the at least one visual image in accordance with the at least one baby-specific educational plan for the at least one baby, and
  - (ii) at least one baby-specific educational recommendation based at least in part on the at least one indication;
- transmit over the communication network, to the at least one communication device of the at least one user, the at least one indication, the at least one baby-specific educational recommendation, the sensor data, or any combination thereof; and
- execute, based on the at least one baby-specific educational recommendation, at least one of:
  - (i) a modification of the at least one baby-specific educational plan when the at least one indication indicates that the at least one baby did not understand, or
  - (ii) a continued execution of the baby-specific educational plan for the at least one baby.

In some embodiments, the at least one processor is further configured to receive user-instructions from the at least one user through a graphic user interface on the at least one communication device associated with the at least one user.

In some embodiments, the at least one processor is further configured to execute, based on the at least one indication, the at least one baby-specific educational recommendation, and the user-instructions, at least one of:
- (i) the modification of the at least one baby-specific educational plan when the at least one indication indicates that the at least one baby did not understand, or
- (ii) the continued execution of the baby-specific educational plan for the at least one baby.

In some embodiments, a sensor from the plurality of sensors is selected from the group consisting of a thermal imager, an infrared (IR) camera, a lidar device, and a radio frequency (RF) device.

In some embodiments, a method may include:
- receiving, by a processor, from at least one electronic resource including a database;
  - where the database includes:
    - (i) baby-specific stimuli data for a plurality of baby-specific stimuli provided to a plurality of babies,
    - (ii) baby-specific response data for a plurality of baby-specific responses acquired in response to the plurality of baby-specific stimuli provided to the plurality of babies, and
    - (iii) baby-specific personal data for each baby in the plurality of babies;
- transmitting, by the processor, instructions to the projection device to project at least one visual image to the at least one baby based on a baby-specific educational plan from the plurality of baby-specific educational plans for the at least one baby;
- transmitting, by the processor, instructions to the audio system to generate, at least one sound associated with the at least one visual image;
- receiving, by the processor, from an imaging device, image data of an image of at least one baby from the plurality of images;
- receiving, by the processor, from a microphone, the audio signal data of the at least one baby;
- receiving, by the processor, from a plurality of sensors, sensor data associated with the at least one baby;
- determining, by the processor, baby-specific physiological data of the at least one baby based on the image data, the sensor data, and the audio signal data;
  - where the baby-specific physiological data may include:
    - (i) breathing rate signal data of the at least one baby,
    - (ii) spatial body temperature distribution data of the at least one baby,
    - (iii) heartbeat signal data of the at least one baby,
    - (iv) baby motion data of the at least one baby, and
    - (v) baby voice classification data of the at least one baby;
- inputting, by the processor, to at least one baby-specific educational machine learning model, the image data, the audio signal data, the sensor data, the at least one visual image, the at least one sound, the baby-specific physiological data, the baby-specific personal data associated with the at least one baby;
  - where the at least one baby-specific educational machine learning model is trained using a dataset based at least in part on the baby-specific stimuli data, the baby-specific response data, and the baby-specific personal data associated with the plurality of babies;

receiving, by the processor, an output from the at least one baby-specific educational machine learning model;
where the output includes:
(i) at least one indication that the at least one baby understood or did not understand the at least one visual image and the at least one sound associated with the at least one visual image in accordance with the at least one baby-specific educational plan for the at least one baby, and
(ii) at least one baby-specific educational recommendation based at least in part on the at least one indication;
transmitting, by the processor, over a communication network, to at least one communication device of at least one user associated with the at least one baby, the at least one indication, the at least one baby-specific educational recommendation, the sensor data, or any combination thereof; and
executing, by the processor, based on the at least one baby-specific educational recommendation, at least one of:
(i) a modification of the at least one baby-specific educational plan when the at least one indication indicates that the at least one baby did not understand, or
(ii) a continued execution of the baby-specific educational plan for the at least one baby.

In some embodiments, the method includes receiving, by the processor, user-instructions from the at least one user through a graphic user interface on the at least one communication device associated with the at least one user.

In some embodiments, the method includes executing, by the processor, based on the at least one indication, the at least one baby-specific educational recommendation and the user-instructions, at least one of:
(i) the modification of the at least one baby-specific educational plan when the at least one indication indicates that the at least one baby did not understand, or
(ii) the continued execution of the baby-specific educational plan for the at least one baby.

In some embodiments, a sensor from the plurality of sensors is selected from the group consisting of a thermal imager, an infrared (IR) camera, a lidar device, and a radio frequency (RF) device.

In some embodiments, a method includes:
receiving, by a processor, from at least one electronic resource including a database;
where the database includes:
(i) a baby-specific educational plan from a plurality of baby-specific educational plans for each baby in a plurality of babies,
(ii) baby-specific stimuli data for a plurality of baby-specific stimuli provided to each baby in the plurality of babies,
(iii) baby-specific response data for a plurality of baby-specific responses for each baby acquired in response to the baby-specific stimuli data provided to each baby, and
(iv) baby-specific personal data for each baby in the plurality of babies;
determining, by the processor, from the baby-specific stimuli data and the baby-specific response data for each baby:
(i) sensor data from a plurality of sensors acquired while monitoring each baby in the plurality of babies,
(ii) image data from an image device acquired while monitoring each baby,
(iii) at least one visual image presented to each baby based on the baby-specific educational plan,
(iv) at least one sound associated with the at least one visual image played to each baby, and
(v) audio data from a microphone acquired while monitoring each baby;
determining, by the processor, baby-specific physiological data for each baby based on the image data, the sensor data, and the audio signal data;
where the baby-specific physiological data includes:
(i) breathing rate signal data for each baby,
(ii) spatial body temperature distribution data for each baby,
(iii) heartbeat signal data for each baby,
(iv) baby motion data for each baby, and
(v) baby voice classification data for each baby;
executing, by the processor, a physics algorithm module that generates baby-specific features and environmental-specific features for each baby in the plurality of babies unique to a baby education use case from the baby-specific physiological data, the image data, the audio data, the sensor data, the at least one visual image, the at least one sound, and the baby-specific personal data for each baby;
executing, by the processor, a time driven pipeline software module configured to calculate from the baby-specific features and the environmental-specific features for each baby unique to the baby education use case, time-dependent baby-specific features and time dependent environmental-specific features for each baby based at least in part on a time series generated from the baby-specific features and the environmental-specific features that characterize feature progression over time;
executing, by the processor, a behavioral model configured to generate a digital twin model for each baby in the plurality of babies based at least in part on:
(1) a correlation between baby-specific behavioral features from the baby-specific features and the environmental-specific features for each baby, and
(2) the baby-specific stimuli data, the baby-specific response data, and the baby-specific personal data for each baby,
executing, by the processor, a feedback environmental generator using the digital twin model of each baby to output at least one recommendation, at least one action, or both to change a behavioral state of each baby in accordance with the baby education use case for each baby; and
generating, by the processor, a training dataset for the baby education use case based at least in part on:
(1) input features for each baby from the plurality of babies including:
(A) the baby-specific features for each baby,
(B) the environmental-specific features for each baby,
(C) the time-dependent baby-specific features for each baby, and
(D) the time dependent environmental-specific features for each baby, and
(2) output features for each baby from the plurality of babies including:
(A) the at least one recommendation for each baby,
(B) the at least one action for each baby, or
(C) both.

In some embodiments, the method includes training, by the processor, the at least one baby-specific behavioral state detection machine learning model with the training dataset unique to the baby educational use case.

In some embodiments, the at least one recommendation for the at least one baby is selected from the group consisting of changing the at least one visual image, changing the at least one sound, modifying the at least one baby-specific educational plan, and continuing execution of the baby-specific educational plan.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of exemplary inventive computer-based systems/platforms, exemplary inventive computer-based devices, and/or exemplary inventive computer-based components of the present disclosure may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In some embodiments, as detailed herein, one or more of exemplary inventive computer-based systems/platforms, exemplary inventive computer-based devices, and/or exemplary inventive computer-based components of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a social media post, a map, an entire application (e.g., a calculator), etc. In some embodiments, as detailed herein, one or more of exemplary inventive computer-based systems/platforms, exemplary inventive computer-based devices, and/or exemplary inventive computer-based components of the present disclosure may be implemented across one or more of various computer platforms such as, but not limited to: (1) FreeBSD, NetBSD, OpenBSD; (2) Linux; (3) Microsoft Windows; (4) OS X (MacOS); (5) MacOS 11; (6) Solaris; (7) Android; (8) iOS; (9) Embedded Linux; (10) Tizen; (11) WebOS; (12) IBM i; (13) IBM AIX; (14) Binary Runtime Environment for Wireless (BREW); (15) Cocoa (API); (16) Cocoa Touch; (17) Java Platforms; (18) JavaFX; (19) JavaFX Mobile; (20) Microsoft DirectX; (21) .NET Framework; (22) Silverlight; (23) Open Web Platform; (24) Oracle Database; (25) Qt; (26) Eclipse Rich Client Platform; (27) SAP NetWeaver; (28) Smartface; and/or (29) Windows Runtime.

In some embodiments, exemplary inventive computer-based systems/platforms, exemplary inventive computer-based devices, and/or exemplary inventive computer-based components of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, exemplary inventive computer-based systems/platforms, exemplary inventive computer-based devices, and/or exemplary inventive computer-based components of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, exemplary inventive computer-based systems/platforms, exemplary inventive computer-based devices, and/or exemplary inventive computer-based components of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, and/or objects. For example, such projections may be a visual overlay for a mobile augmented reality (MAR) application.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, the terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

The aforementioned examples are, of course, illustrative and not restrictive.

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

In some embodiments, the exemplary inventive computer-based systems/platforms, the exemplary inventive computer-based devices, and/or the exemplary inventive computer-based components of the present disclosure may be configured to utilize one or more exemplary AI/machine learning techniques chosen from, but not limited to, decision trees, boosting, support-vector machines, neural networks, nearest neighbor algorithms, Naive Bayes, bagging, random forests, and the like. In some embodiments and, optionally, in combination of any embodiment described above or below, an exemplary neutral network technique may be one of, without limitation, feedforward neural network, radial basis function network, recurrent neural network, convolutional network (e.g., U-net) or other suitable network. In some embodiments and, optionally, in combination of any embodiment described above or below, an exemplary implementation of Neural Network may be executed as follows:
  i) Define Neural Network architecture/model,
  ii) Transfer the input data to the exemplary neural network model,
  iii) Train the exemplary model incrementally,
  iv) determine the accuracy for a specific number of timesteps,
  v) apply the exemplary trained model to process the newly-received input data,
  vi) optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the inventive systems/platforms, and the inventive devices described herein can be utilized in any combination with each other. Further still, the various steps may be carried out in any desired order (and any desired steps may be added and/or any desired steps may be eliminated).

The invention claimed is:

1. A system, comprising:
a non-volatile memory;
at least one electronic resource comprising at least one database;
wherein the at least one database comprises:
(i) a plurality of baby-specific educational plans for a plurality of babies,
(ii) baby-specific stimuli data for a plurality of baby-specific stimuli provided to the plurality of babies based on the plurality of baby-specific educational plans,
(iii) baby-specific response data for a plurality of baby-specific responses acquired in response to the plurality of baby-specific stimuli provided to the plurality of babies, and
(iv) baby personal data for each baby in the plurality of babies;
an optical subsystem comprising an imaging device, a projection device, or both;
wherein the optical subsystem is configured to perform for at least one baby from the plurality of babies at least one of:
(i) acquire image data from the imaging device of an image of the at least one baby, or
(ii) project by the projection device, at least one visual image to be viewed by the at least one baby;
an audio system comprising a microphone, a speaker, or both;
wherein the audio system is configured to perform at least one of:
(i) receive by the microphone, audio signal data from the at least one baby, or
(ii) generate by the speaker, at least one sound for the at least one baby;
a plurality of sensors outputting sensor data;
a communication circuitry configured to communicate over a communication network with at least one communication device of at least one user associated with the at least one baby; and
at least one processor configured to execute code stored in the non-volatile memory that causes the at least one processor to:
project by the projection device, the at least one visual image to the at least one baby based on at least one baby-specific educational plan from the plurality of baby-specific educational plans for the at least one baby;
generate by the audio system, the at least one sound associated with the at least one visual image;
receive the image data, the audio signal data, the sensor data, or any combination thereof associated with the at least one baby;
determine baby-specific physiological data of the at least one baby based on the image data, the sensor data, and the audio signal data;
wherein the baby-specific physiological data comprises:
(i) breathing rate signal data of the at least one baby,
(ii) spatial body temperature distribution data of the at least one baby,
(iii) heartbeat signal data of the at least one baby,
(iv) baby motion data of the at least one baby, and
(v) baby voice classification data of the at least one baby;
input to at least one baby-specific educational machine learning model, the image data, the audio signal data, the sensor data, the at least one visual image, the at least one sound, the baby-specific physiological data, the baby personal data of the at least one baby;
wherein the at least one baby-specific educational machine learning model is trained using datasets based at least in part on the baby-specific stimuli data, the baby-specific response data, the baby personal data, the plurality of baby-specific educational plans, or any combination thereof for each baby in the plurality of babies;
receive an output from the at least one baby-specific educational machine learning model;
wherein the output comprises:
(i) at least one indication providing a determination that the at least one baby understood or did not understand the at least one visual image and the at least one sound associated with the at least one visual image in accordance with the at least one baby-specific educational plan for the at least one baby, and
(ii) at least one baby-specific educational recommendation based at least in part on the at least one indication;
transmit over the communication network, to the at least one communication device of the at least one user, the at least one indication, the at least one baby-specific educational recommendation, the sensor data, or any combination thereof; and
execute, based on the at least one baby-specific educational recommendation, at least one of:
(i) a modification of the at least one baby-specific educational plan based on the determination that the at least one indication indicates that the at least one baby did not understand, or
(ii) a continued execution of the at least one baby-specific educational plan for the at least one baby.

2. The system according to claim 1, wherein the at least one processor is further configured to receive user-instructions from the at least one user through a graphic user interface on the at least one communication device associated with the at least one user.

3. The system according to claim 2, wherein the at least one processor is further configured to execute, based on the at least one indication, the at least one baby-specific educational recommendation, and the user-instructions, at least one of:
(i) the modification of the at least one baby-specific educational plan based on the determination that the at least one indication indicates that the at least one baby did not understand, or (ii) the continued execution of the at least one baby-specific educational plan for the at least one baby.

4. The system according to claim 1, wherein a sensor from the plurality of sensors is selected from the group consisting of a thermal imager, an infrared (IR) camera, a lidar device, and a radio frequency (RF) device.

5. A method, comprising:
receiving, by a processor, from at least one database stored in at least one electronic resource:
   (i) baby-specific stimuli data for a plurality of baby-specific stimuli provided to a plurality of babies,
   (ii) baby-specific response data for a plurality of baby-specific responses acquired in response to the plurality of baby-specific stimuli provided to the plurality of babies, and
   (iii) baby personal data for each baby in the plurality of babies;
transmitting, by the processor, instructions to a projection device to project at least one visual image to at least one baby based on at least one baby-specific educational plan from a plurality of baby-specific educational plans for the at least one baby;
transmitting, by the processor, instructions to an audio system to generate, at least one sound associated with the at least one visual image;
receiving, by the processor, from an imaging device, image data of an image of at least one baby;
receiving, by the processor, from a microphone, audio signal data of the at least one baby;
receiving, by the processor, from a plurality of sensors, sensor data associated with the at least one baby;
determining, by the processor, baby-specific physiological data of the at least one baby based on the image data, the sensor data, and the audio signal data;
   wherein the baby-specific physiological data comprises:
   (i) breathing rate signal data of the at least one baby,
   (ii) spatial body temperature distribution data of the at least one baby,
   (iii) heartbeat signal data of the at least one baby,
   (iv) baby motion data of the at least one baby, and
   (v) baby voice classification data of the at least one baby;
inputting, by the processor, to at least one baby-specific educational machine learning model, the image data, the audio signal data, the sensor data, the at least one visual image, the at least one sound, the baby-specific physiological data, the baby personal data of the at least one baby;
   wherein the at least one baby-specific educational machine learning model is trained using a dataset based at least in part on the baby-specific stimuli data, the baby-specific response data, and the baby personal data for each baby in the plurality of babies;
receiving, by the processor, an output from the at least one baby-specific educational machine learning model;
   wherein the output comprises:
   (i) at least one indication providing a determination that the at least one baby understood or did not understand the at least one visual image and the at least one sound associated with the at least one visual image in accordance with the at least one baby-specific educational plan for the at least one baby, and
   (ii) at least one baby-specific educational recommendation based at least in part on the at least one indication;
transmitting, by the processor, over a communication network, to at least one communication device of at least one user associated with the at least one baby, the at least one indication, the at least one baby-specific educational recommendation, the sensor data, or any combination thereof; and
executing, by the processor, based on the at least one baby-specific educational recommendation, at least one of:
   (i) a modification of the at least one baby-specific educational plan based on the determination that the at least one indication indicates that the at least one baby did not understand, or
   (ii) a continued execution of the at least one baby-specific educational plan for the at least one baby.

6. The method according to claim 5, further comprising receiving, by the processor, user-instructions from the at least one user through a graphic user interface on the at least one communication device associated with the at least one user.

7. The method according to claim 6, further comprising executing, by the processor, based on the at least one indication, the at least one baby-specific educational recommendation and the user-instructions, at least one of:
   (i) the modification of the at least one baby-specific educational plan based on the determination that the at least one indication indicates that the at least one baby did not understand, or
   (ii) the continued execution of the at least one baby-specific educational plan for the at least one baby.

8. The method according to claim 5, wherein a sensor from the plurality of sensors is selected from the group consisting of a thermal imager, an infrared (IR) camera, a lidar device, and a radio frequency (RF) device.

9. A method, comprising:
receiving, by a processor, from at least one database stored in at least one electronic resource:
   (i) a baby-specific educational plan from a plurality of baby-specific educational plans for each baby in a plurality of babies,
   (ii) baby-specific stimuli data for a plurality of baby-specific stimuli provided to each baby in the plurality of babies,
   (iii) baby-specific response data for a plurality of baby-specific responses for each baby acquired in response to the baby-specific stimuli data provided to each baby, and
   (iv) baby personal data for each baby in the plurality of babies;
determining, by the processor, from the baby-specific stimuli data and the baby-specific response data for each baby:
   (i) sensor data from a plurality of sensors acquired while monitoring each baby in the plurality of babies,
   (ii) image data from an image device acquired while monitoring each baby,
   (iii) at least one visual image presented to each baby based on the baby-specific educational plan,
   (iv) at least one sound associated with the at least one visual image played to each baby, and
   (v) audio signal data from a microphone acquired while monitoring each baby;

determining, by the processor, baby-specific physiological data for each baby based on the image data, the sensor data, and the audio signal data;
  wherein the baby-specific physiological data comprises:
    (i) breathing rate signal data for each baby,
    (ii) spatial body temperature distribution data for each baby,
    (iii) heartbeat signal data for each baby,
    (iv) baby motion data for each baby, and
    (v) baby voice classification data for each baby;
executing, by the processor, a physics algorithm module that generates baby-specific features and environmental-specific features for each baby in the plurality of babies unique to a baby education use case from the baby-specific physiological data, the image data, the audio signal data, the sensor data, the at least one visual image, the at least one sound, and the baby personal data for each baby;
executing, by the processor, a time driven pipeline software module configured to calculate from the baby-specific features and the environmental-specific features for each baby unique to the baby education use case, baby-specific time-dependent features and environmental-specific time dependent features for each baby based at least in part on a time series generated from the baby-specific features and the environmental-specific features that characterize feature progression over time;
executing, by the processor, a behavioral model configured to generate a digital twin model for each baby in the plurality of babies based at least in part on:
  (1) a correlation between baby-specific behavioral features from the baby-specific features and the environmental-specific features for each baby, and
  (2) the baby-specific stimuli data, the baby-specific response data, and the baby personal data for each baby;
  wherein the digital twin model comprises a set of parameters representing different responses to different stimuli for each baby in the plurality of babies based on each baby being in different behavioral states during different time intervals;
executing, by the processor, a feedback environmental generator using the digital twin model of each baby to output at least one recommendation, at least one action, or both to change a behavioral state of each baby in accordance with the baby education use case for each baby; and
generating, by the processor, a training dataset for the baby education use case based at least in part on:
  (1) input features for each baby from the plurality of babies comprising:
    (A) the baby-specific features for each baby,
    (B) the environmental-specific features for each baby,
    (C) the baby-specific time-dependent features for each baby, and
    (D) the environmental-specific time dependent features for each baby, and
  (2) output features for each baby from the plurality of babies comprising:
    (A) the at least one recommendation for each baby,
    (B) the at least one action for each baby, or
    (C) both.

10. The method according to claim 9, further comprising training, by the processor, at least one baby-specific behavioral state detection machine learning model with the training dataset unique to a baby educational use case.

11. The method according to claim 9, wherein the at least one recommendation for each baby is selected from the group consisting of changing the at least one visual image, changing the at least one sound, modifying the baby-specific educational plan, and continuing execution of the baby-specific educational plan.

* * * * *